US012193669B2

(12) United States Patent
Beckman et al.

(10) Patent No.: US 12,193,669 B2
(45) Date of Patent: Jan. 14, 2025

(54) MANUAL DRIVE FUNCTIONS FOR SURGICAL TOOL

(71) Applicant: CILAG GMBH INTERNATIONAL, Zug (CH)

(72) Inventors: Andrew T. Beckman, Cincinnati, OH (US); Charles J. Scheib, Loveland, OH (US); Jason A. Hill, Loveland, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/350,382

(22) Filed: Jul. 11, 2023

(65) Prior Publication Data

US 2023/0346376 A1 Nov. 2, 2023

Related U.S. Application Data

(63) Continuation of application No. 17/036,760, filed on Sep. 29, 2020, now Pat. No. 11,701,117.

(51) Int. Cl.
*A61B 17/00* (2006.01)
*A61B 17/072* (2006.01)
(Continued)

(52) U.S. Cl.
CPC ........ *A61B 17/07207* (2013.01); *A61B 34/30* (2016.02); *A61B 34/76* (2016.02);
(Continued)

(58) Field of Classification Search
CPC ... A61B 17/07207; A61B 34/30; A61B 34/76; A61B 1/2676; A61B 1/307; A61B 10/04;
(Continued)

(56) References Cited

U.S. PATENT DOCUMENTS 4,651,591 A * 3/1987 Wurst ........................ B25J 9/08
475/9
4,688,555 A * 8/1987 Wardle ............... A61B 1/00042
600/149
(Continued)

FOREIGN PATENT DOCUMENTS

WO 2019191420 A1 10/2019
WO WO-2022070028 A1 * 4/2022 ............. A61B 17/00

OTHER PUBLICATIONS

Written Opinion and International Search Report from corresponding PCT Application No. PCT/IB2021/058834 mailed Feb. 14, 2022.

*Primary Examiner* — Robert F Long
(74) *Attorney, Agent, or Firm* — Vorys, Sater, Seymour and Pease LLP

(57) ABSTRACT

A surgical tool includes a drive housing having opposing first and second ends and a drive input rotatably mounted to the drive housing at the first end, a carriage mounted entirely within the drive housing and movable between the first and second ends via actuation of the drive input, an instrument driver matable with the drive housing at the first end, a drive output matable with the drive input such that rotation of the drive output rotates the drive input and translates the carriage within the drive housing, a shaft coupled to and extending distally from the carriage and penetrating the first end and the instrument driver, and a fin connected to the carriage and accessible by a user at an exterior of the drive housing, the fin being manually translatable along the exterior of the drive housing between the first and second ends to thereby translate the carriage.

12 Claims, 38 Drawing Sheets

(51) Int. Cl.
A61B 34/00 (2016.01)
A61B 34/30 (2016.01)
*A61B 1/267* (2006.01)
*A61B 1/307* (2006.01)
*A61B 10/04* (2006.01)
*A61B 50/13* (2016.01)
*A61G 13/10* (2006.01)

(52) U.S. Cl.
CPC ............ *A61B 1/2676* (2013.01); *A61B 1/307* (2013.01); *A61B 10/04* (2013.01); *A61B 2010/045* (2013.01); *A61B 2017/00039* (2013.01); *A61B 2017/00075* (2013.01); *A61B 2017/00212* (2013.01); *A61B 2017/00367* (2013.01); *A61B 2017/00398* (2013.01); *A61B 2017/00477* (2013.01); *A61B 2017/07264* (2013.01); *A61B 2034/301* (2016.02); *A61B 2034/305* (2016.02); *A61B 50/13* (2016.02); *A61G 13/101* (2013.01)

(58) Field of Classification Search
CPC ............ A61B 50/13; A61B 2010/045; A61B 2017/00039; A61B 2017/00075; A61B 2017/00212; A61B 2017/00367; A61B 2017/00398; A61B 2017/00477; A61B 2017/07264; A61B 2034/301; A61B 2034/305; A61B 34/37; A61B 90/98; A61B 2017/07285; A61G 13/101; A61G 13/06; A61G 13/04; A61G 13/10
USPC ............................................ 227/175.1–182.1
See application file for complete search history.

(56) References Cited

U.S. PATENT DOCUMENTS

| | | | | |
|---|---|---|---|---|
| 6,389,921 | B1* | 5/2002 | Nada ................... | B25J 19/0029 901/29 |
| 10,368,954 | B2* | 8/2019 | Brisson ................ | A61B 34/30 |
| 10,603,126 | B2* | 3/2020 | Karguth ............... | A61B 46/10 |
| 11,701,116 | B2* | 7/2023 | Beckman .............. | A61G 13/04 227/175.1 |
| 2007/0175957 | A1* | 8/2007 | Shelton ................. | A61B 34/76 227/178.1 |
| 2007/0250113 | A1* | 10/2007 | Hegeman ............. | A61B 1/0055 606/207 |
| 2009/0108048 | A1* | 4/2009 | Zemlok ................ | A61B 17/105 227/176.1 |
| 2011/0290854 | A1* | 12/2011 | Timm ................. | A61B 17/0684 227/178.1 |
| 2011/0290855 | A1* | 12/2011 | Moore .................. | A61B 34/30 227/176.1 |
| 2013/0023868 | A1* | 1/2013 | Worrell ............ | A61B 17/07207 606/205 |
| 2013/0098966 | A1* | 4/2013 | Kostrzewski .... | A61B 17/07207 606/1 |
| 2013/0296886 | A1* | 11/2013 | Green ................... | A61B 34/70 606/130 |
| 2014/0257333 | A1* | 9/2014 | Blumenkranz ........ | A61B 34/71 606/130 |
| 2014/0276723 | A1* | 9/2014 | Parihar ............ | A61B 17/07207 606/33 |
| 2014/0305992 | A1* | 10/2014 | Kimsey ................ | A61B 17/282 227/176.1 |
| 2015/0080924 | A1* | 3/2015 | Stulen ............ | A61B 17/320092 606/169 |
| 2015/0150636 | A1 | 6/2015 | Hagn et al. | |
| 2016/0016320 | A1* | 1/2016 | Rothfuss ................ | A61B 34/30 74/490.06 |
| 2016/0338667 | A1* | 11/2016 | Noonan ................. | A61B 8/467 |
| 2016/0338787 | A1* | 11/2016 | Popovic ............. | A61B 1/00042 |
| 2016/0374672 | A1* | 12/2016 | Bear ........................ | H02J 7/00 606/219 |
| 2017/0319287 | A1* | 11/2017 | Zergiebel ............. | A61B 17/072 |
| 2018/0153545 | A1* | 6/2018 | Zergiebel ......... | A61B 17/07207 |
| 2018/0168756 | A1 | 6/2018 | Liao et al. | |
| 2018/0333155 | A1* | 11/2018 | Hall ........................ | A61B 90/90 |
| 2019/0038279 | A1* | 2/2019 | Shelton, IV ......... | A61B 17/068 |
| 2019/0038281 | A1 | 2/2019 | Shelton, IV et al. | |
| 2019/0125468 | A1* | 5/2019 | Adams ................... | A61B 34/30 |
| 2019/0183594 | A1* | 6/2019 | Shelton, IV .......... | A61B 34/71 |
| 2019/0192245 | A1* | 6/2019 | Abbott ................... | A61B 34/35 |
| 2019/0231451 | A1* | 8/2019 | Lambrecht ............. | F16H 55/17 |
| 2019/0321041 | A1 | 10/2019 | Shelton, IV | |
| 2020/0155151 | A1* | 5/2020 | Overmyer .............. | A61B 34/30 |
| 2020/0405407 | A1* | 12/2020 | Shelton, IV .......... | A61B 34/37 |
| 2021/0145522 | A1* | 5/2021 | DeBuys ............ | A61M 25/0136 |
| 2021/0369368 | A1* | 12/2021 | Heiliger ................. | A61B 34/71 |
| 2021/0393340 | A1* | 12/2021 | Beckman .............. | A61B 17/072 |
| 2021/0393341 | A1* | 12/2021 | Beckman ............... | A61B 34/30 |
| 2021/0393342 | A1* | 12/2021 | Beckman ............... | F16H 25/20 |
| 2021/0393347 | A1* | 12/2021 | Beckman ............... | B25J 5/007 |
| 2022/0022976 | A1* | 1/2022 | Beckman .............. | A61B 34/37 |
| 2022/0202517 | A1* | 6/2022 | Overmyer .............. | A61B 34/30 |

\* cited by examiner

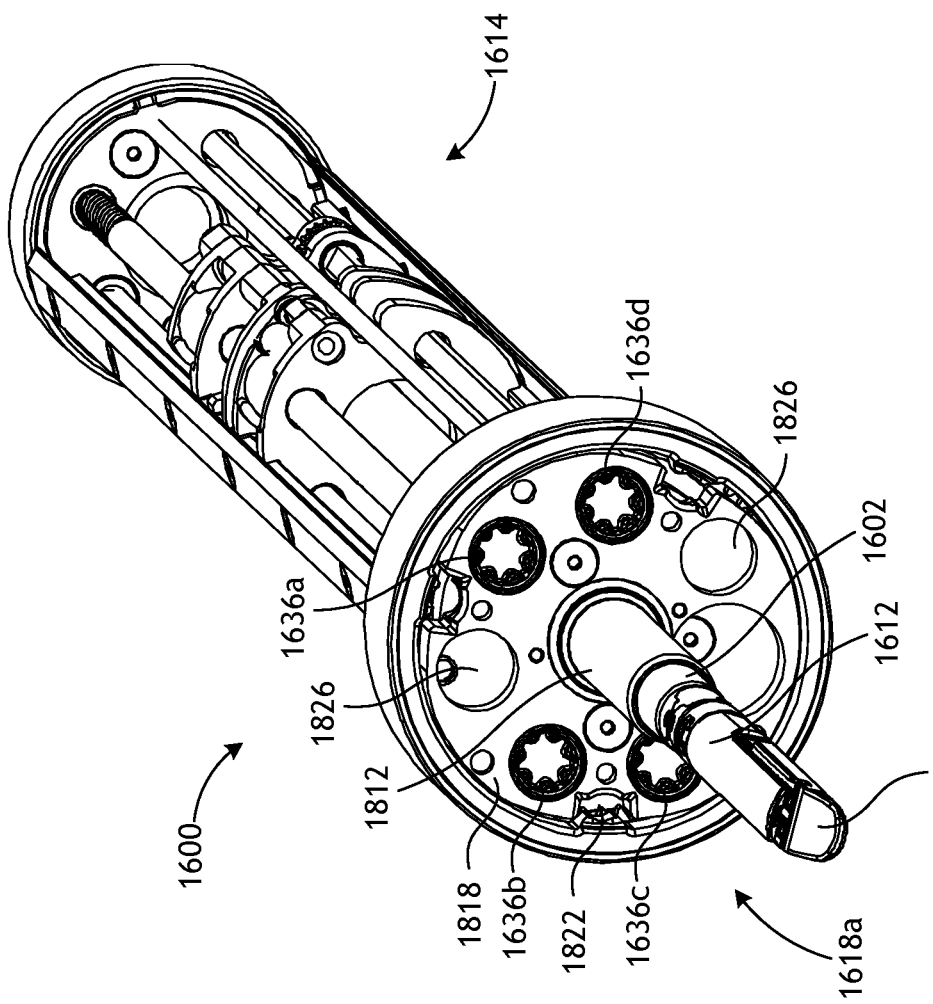
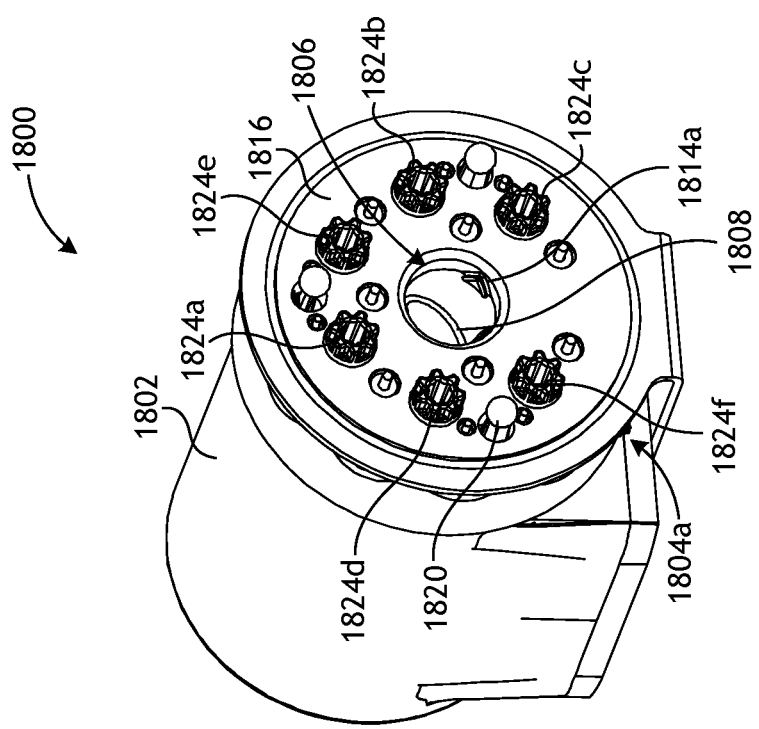
FIG. 18B

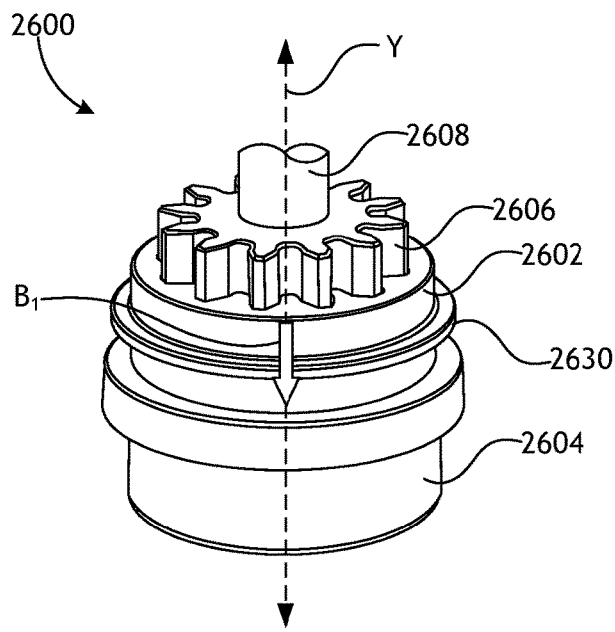
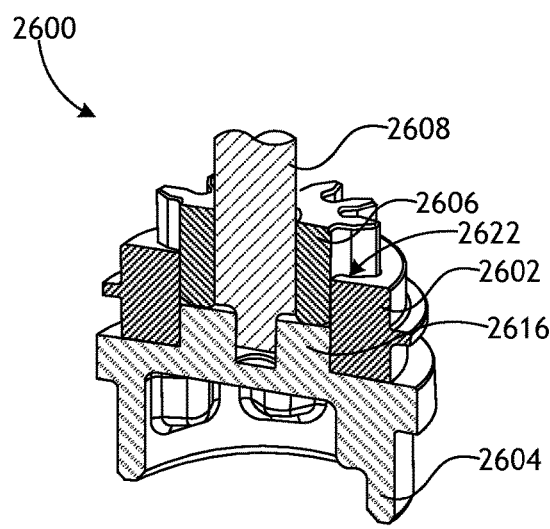
FIG. 27A    FIG. 27B
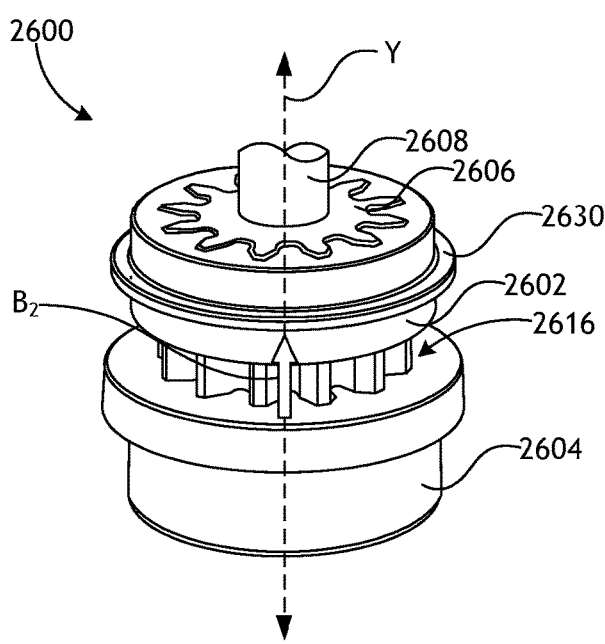
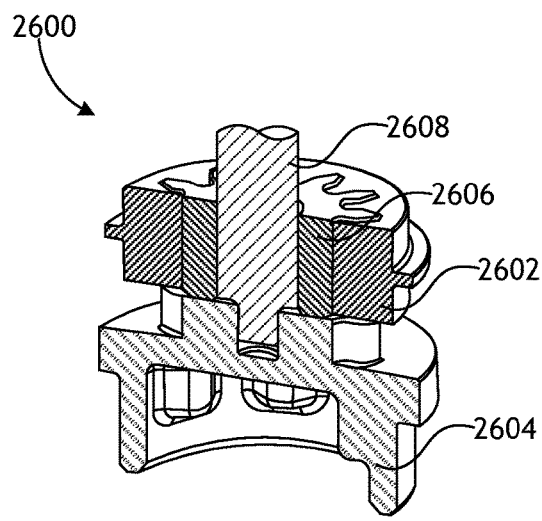
FIG. 27C    FIG. 27D

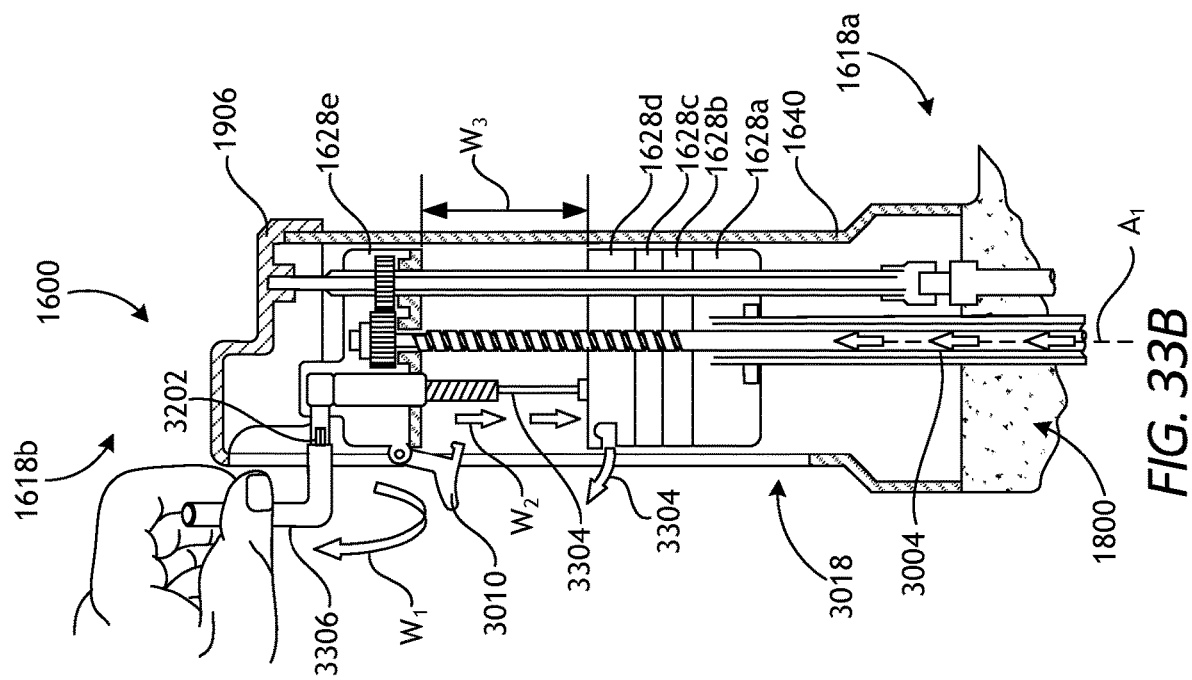
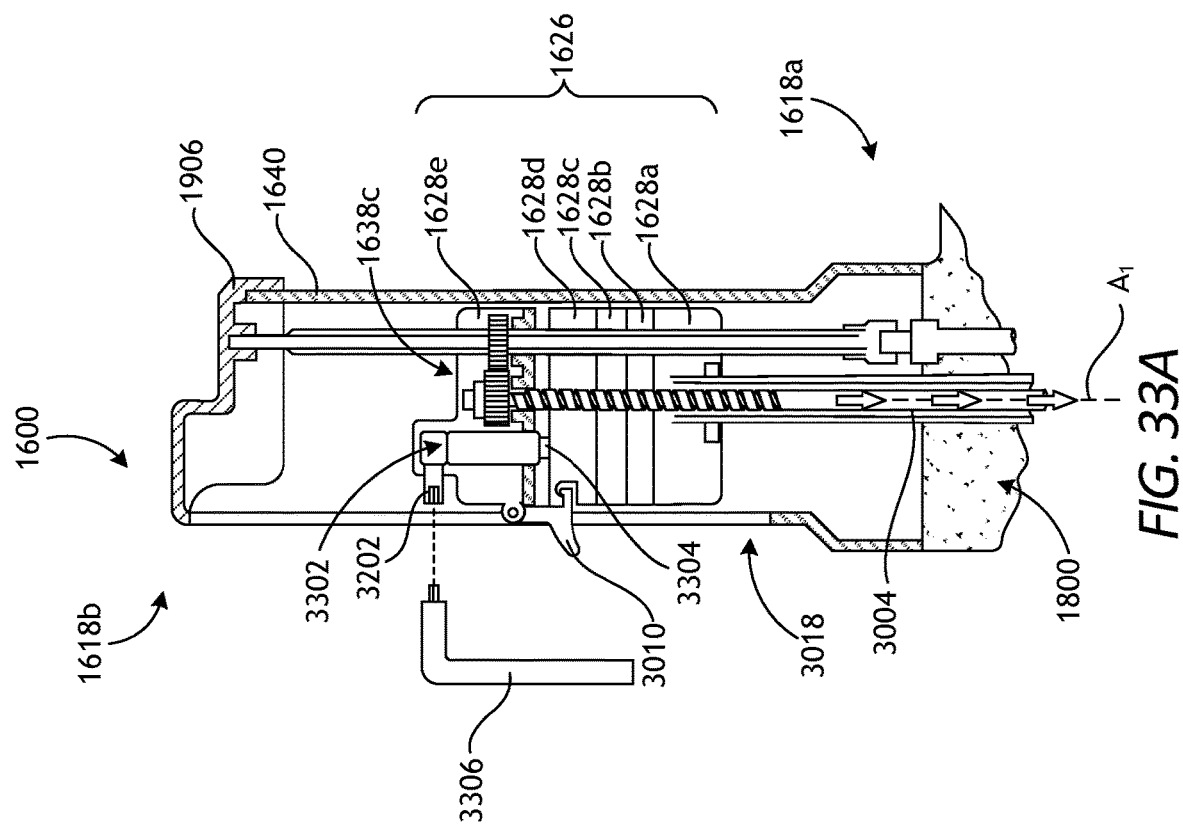

MANUAL DRIVE FUNCTIONS FOR SURGICAL TOOL

TECHNICAL FIELD

The systems and methods disclosed herein are directed to surgical tools and, more particularly, to mechanisms for manually manipulating various functions of a robotic surgical tool.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving the drive cables articulates the end effector to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a surgical tool comprising a drive housing having a first end and a second end and a drive input at the first end, a carriage mounted within the drive housing and being movable between the first and second ends via actuation of the drive input, an instrument driver arranged at an end of a robotic arm and matable with the first end of the drive housing, a drive output provided by the instrument driver and matable with the drive input such that rotation of the drive output correspondingly rotates the drive input to thereby translate the carriage within the drive housing, and a fin connected to the carriage and user accessible from an exterior of the drive housing to manually translate the carriage. In some embodiments, the drive housing includes a shroud extending between the first and second end and the fin radially protrudes outward through a window defined in the shroud. In some embodiments, the tool further includes a ring extending from the fin at least partially around an outer surface of the shroud. In some embodiments, the carriage comprises one or more distal layers and one or more proximal layers attachable to the one or more distal layers, and the surgical tool further comprises a bailout mechanism operable to unlock the one or more proximal layers from the one or more distal layers of the carriage such that the one or more proximal layers may be withdrawn from the drive housing. In some embodiments, the bailout mechanism includes a releasable pin movable between a locked position, where the one or more proximal layers are secured to the one or more distal layers, and an unlocked position, where the one or more proximal layers are unsecured from and movable relative to the one or more distal layers. In some embodiments, when in the locked position, the releasable pin is attached to a locking feature provided within a proximal most layer of the one or more distal layers and the drive input is operatively coupled to the one or more distal layers. In some embodiments, the fin provides an overhanging portion positioned radially outward from the drive housing and extending distally from the fin to cover at least a portion of the one or more distal layers. In some embodiments, the surgical tool further includes an elongate shaft extending distally from the carriage and penetrating the first end, and an end effector arranged at a distal end of the elongate shaft. In some embodiments, the carriage comprises one or more distal layers and one or more proximal layers removably secured to the one or more distal layers, and the surgical tool further includes a position recognition system programmed to remember a last known position of the end effector when the one or more proximal layers are removed from the one or more distal layers.

Embodiments disclosed herein may further include a method of positioning a surgical tool, the method comprising grasping onto a fin of a user interface operatively coupled to a drive housing of the surgical tool, the surgical tool including a drive input at the first end of the drive housing, and a carriage mounted within the drive housing and being movable between the first and second ends via actuation of the drive input, wherein the fin is operatively coupled to the carriage, manually moving the fin along an exterior of the drive housing and thereby moving the carriage within the drive housing, and rotating the drive input as the carriage is manually moved within the drive housing. In some embodiments, the surgical tool further comprises an instrument driver arranged at an end of a robotic arm and matable with the first end of the drive housing, and a drive output provided by the instrument driver and matable with the drive input such that rotation of the drive output correspondingly rotates the drive input to thereby translate the carriage, and wherein rotating the drive input comprises backdriving the drive output provided by the instrument driver. In some embodiments, the surgical tool further comprises an elongate shaft extending distally from the carriage and penetrating the first end, an end effector arranged at a distal end of the elongate shaft, and one or more distal layers and one or more proximal layers removably secured to the one or more distal layers to form the carriage, and the method further comprises: monitoring a position of the end effector with a position recognition system, removing the one or more proximal layers from the one or more distal layers, and remembering a last known position of the end effector when the one or more proximal layers are removed from the one or more distal layers. In some embodiments, the method further comprises re-installing the one or more proximal layers on the one or more distal layers, and determining with the position recognition system whether the one or more proximal layers were previously installed on the one or more distal layers. In some embodiments, the method further comprises positively determining with the position recognition system that the one or more proximal layers were previously installed on the one or more distal layers, and permitting with the position recognition system manual backdriving of the drive output of the instrument driver to thereby manually translate the end effector. In some embodiments, the method further comprises providing a haptic feedback indication with the position recognition system when the end effector is in the last known position. In some embodiments, the surgical tool is a first surgical tool and the one or more proximal layers comprise a first set of the one or more proximal layers, and the method further comprises installing a second set of the one or more proximal layers on the one or more distal layers corresponding to a second surgical tool, determining with the position recognition system that the second set of the one or more proximal layers were correspond to the second surgical tool and were not previously installed on the one or more distal layers, and preventing manual translation of the end effector beyond the last known position with the position recognition system. In some embodiments, the the end effector comprises a first end effector, and the method further comprises determining with the position recognition system whether the second surgical tool includes the first end effector or a second end effector different than the first end effector, and permitting backdriving of the drive output with the position recognition system when the first and second end effectors are similar. In some embodiments, the method further comprises preventing manual translation of the second end effector beyond the last known position with the position recognition system. In some embodiments, the method further comprises providing a haptic feedback indication with the position recognition system when the second end effector is in the last known position. In some embodiments, the surgical tool further comprises a lead screw extending from the first end of the drive housing and rotatably coupled to the first end at the drive input, a carriage nut provided within the carriage such that the carriage is mounted to the lead screw at the carriage nut, such that rotation of the drive input correspondingly rotates the lead screw to thereby translate the carriage nut along the lead screw, wherein rotating the drive input comprises rotating the lead screw and backdriving the drive input as the carriage is manually moved within the drive housing.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 18B provides separated isometric end views of the instrument driver of FIG. 18A and the surgical tool of FIGS. 16-17.

FIGS. 27A-27D illustrate example operation of the clutching mechanism of FIGS. 26A-D, according to one or more embodiments

illustrates the bailout assist mechanism

Figure 32:
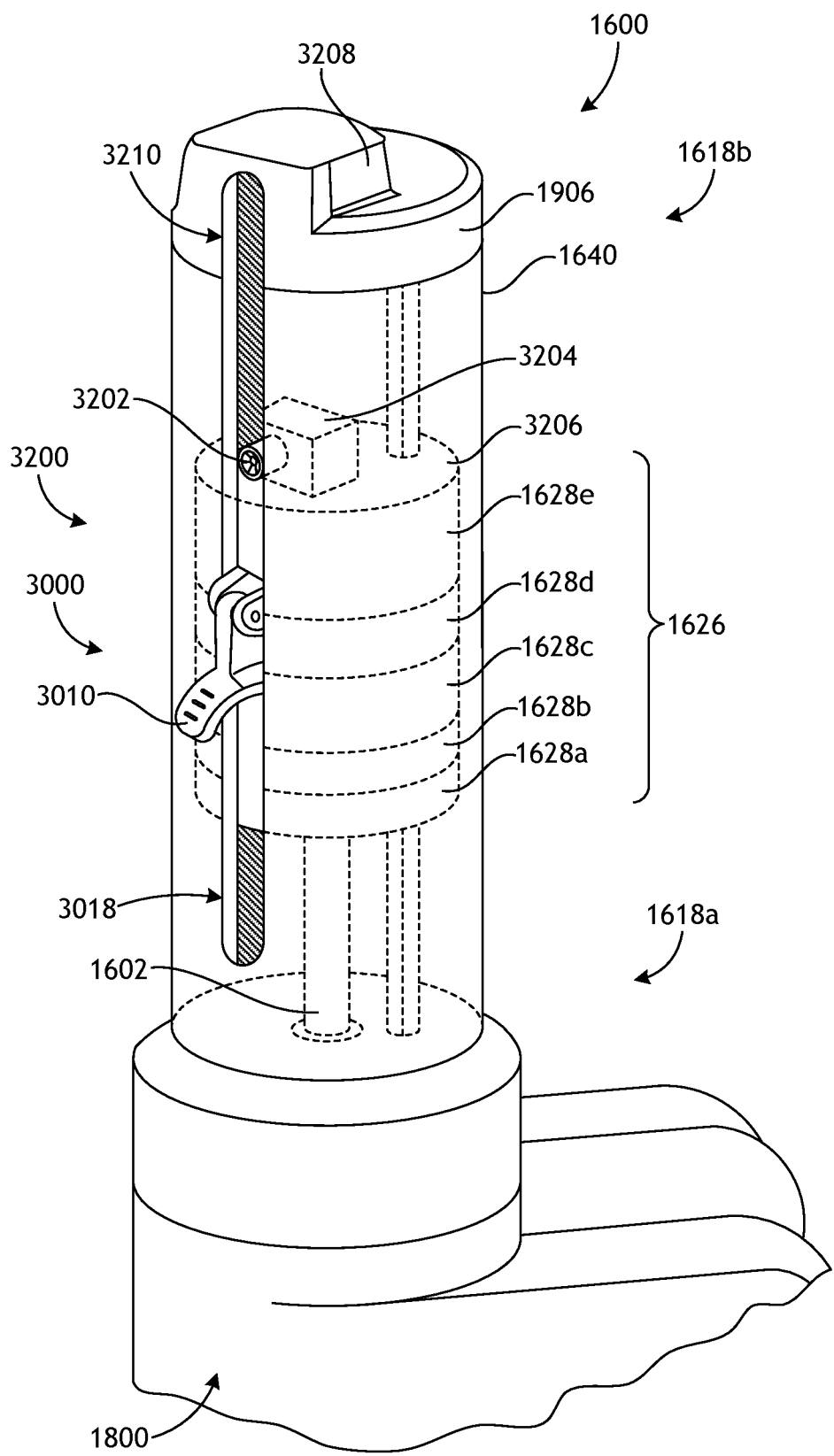
FIG. 32 illustrates the bailout mechanism incorporating a bailout assist mechanism 3200, according to one or more embodiments of the present disclosure.
Figures 34A, 34B:
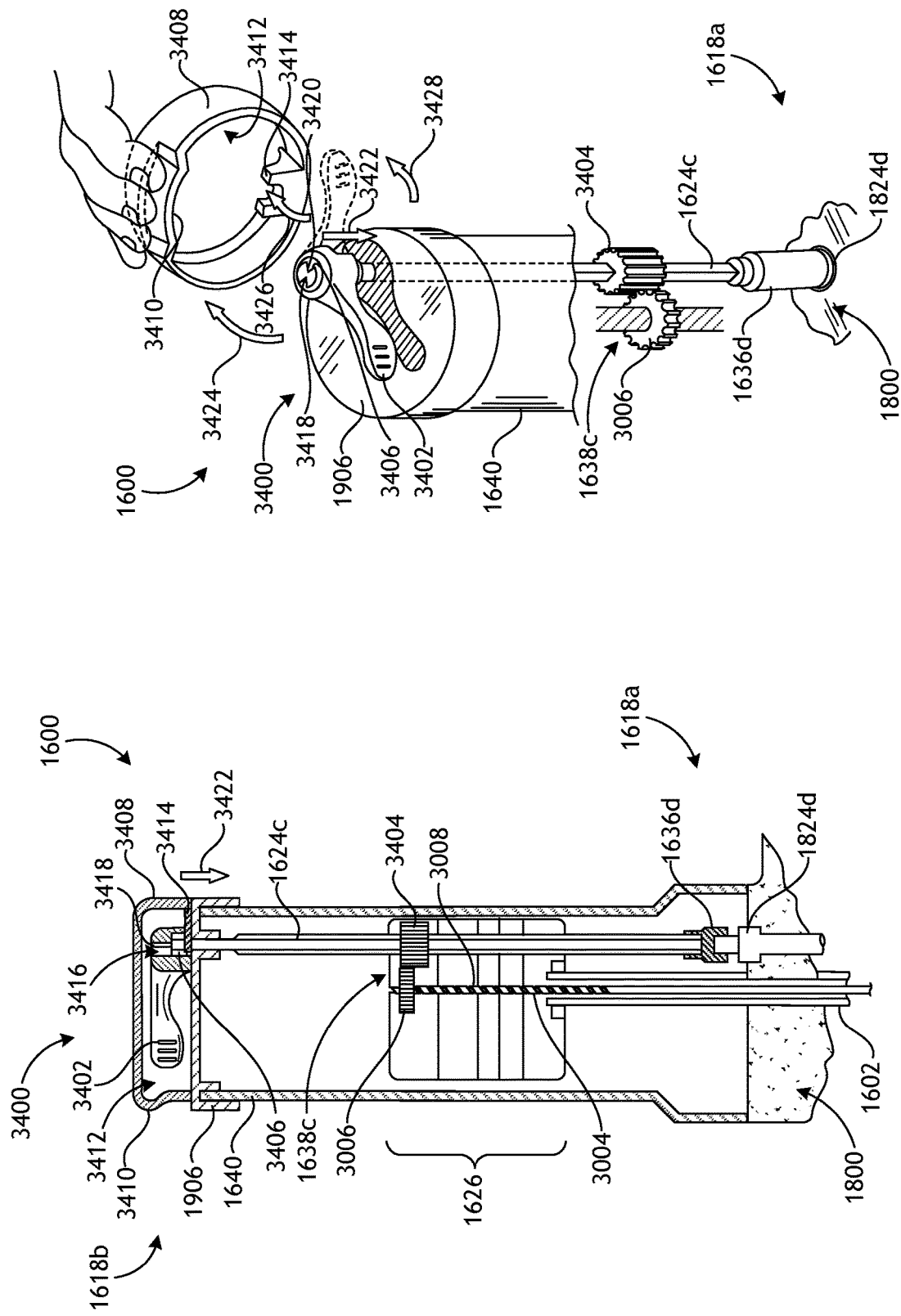

FIGS. 33A-33B illustrate example operation of the bailout assist mechanism of FIG. 32, according to one or more embodiments of the present disclosure FIGS. 34A-34B illustrate a bailout mechanism for a backdrivable motor, according to one or more other embodiments of the present disclosure.

Figure 35A:
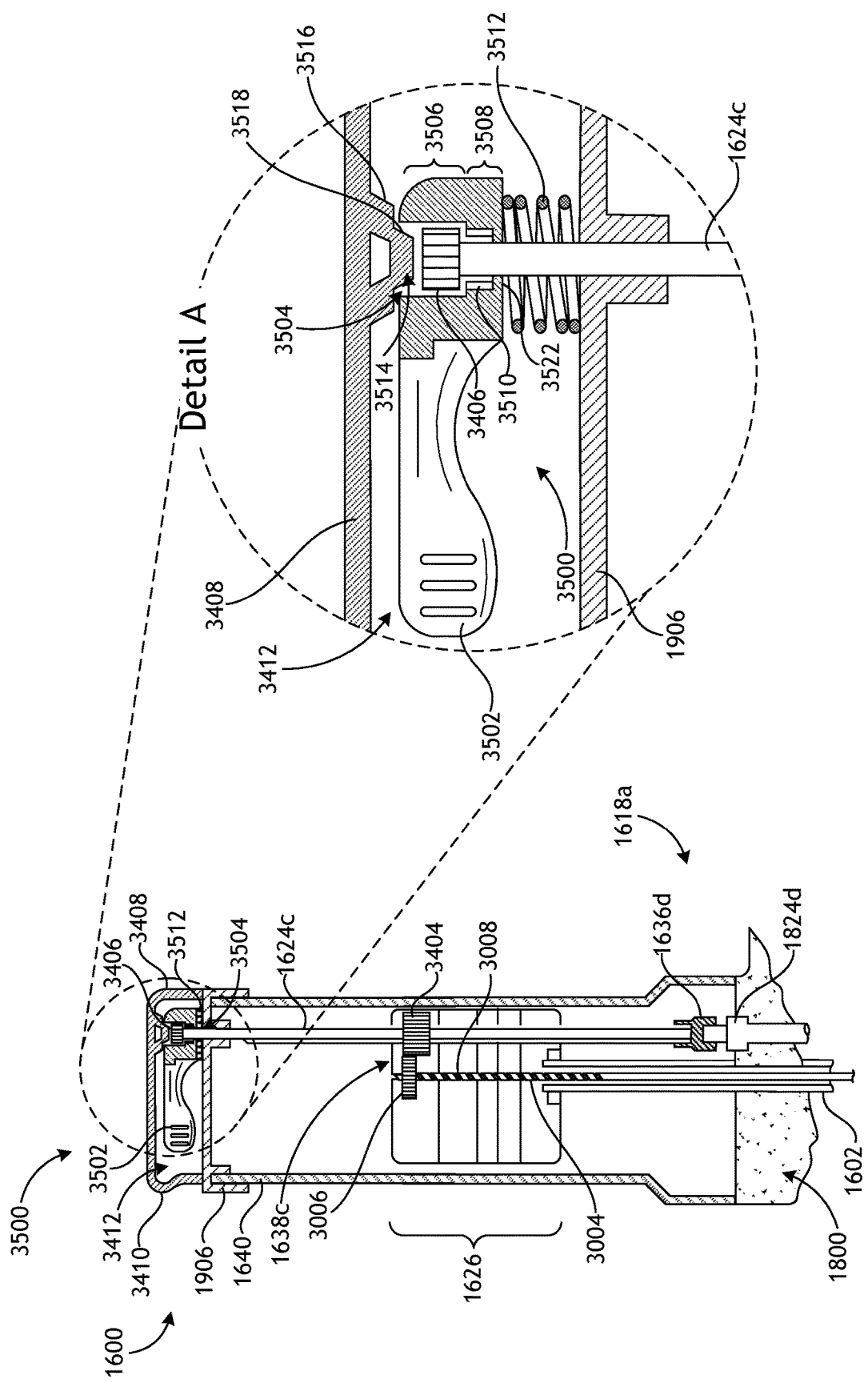
Figure 35B:
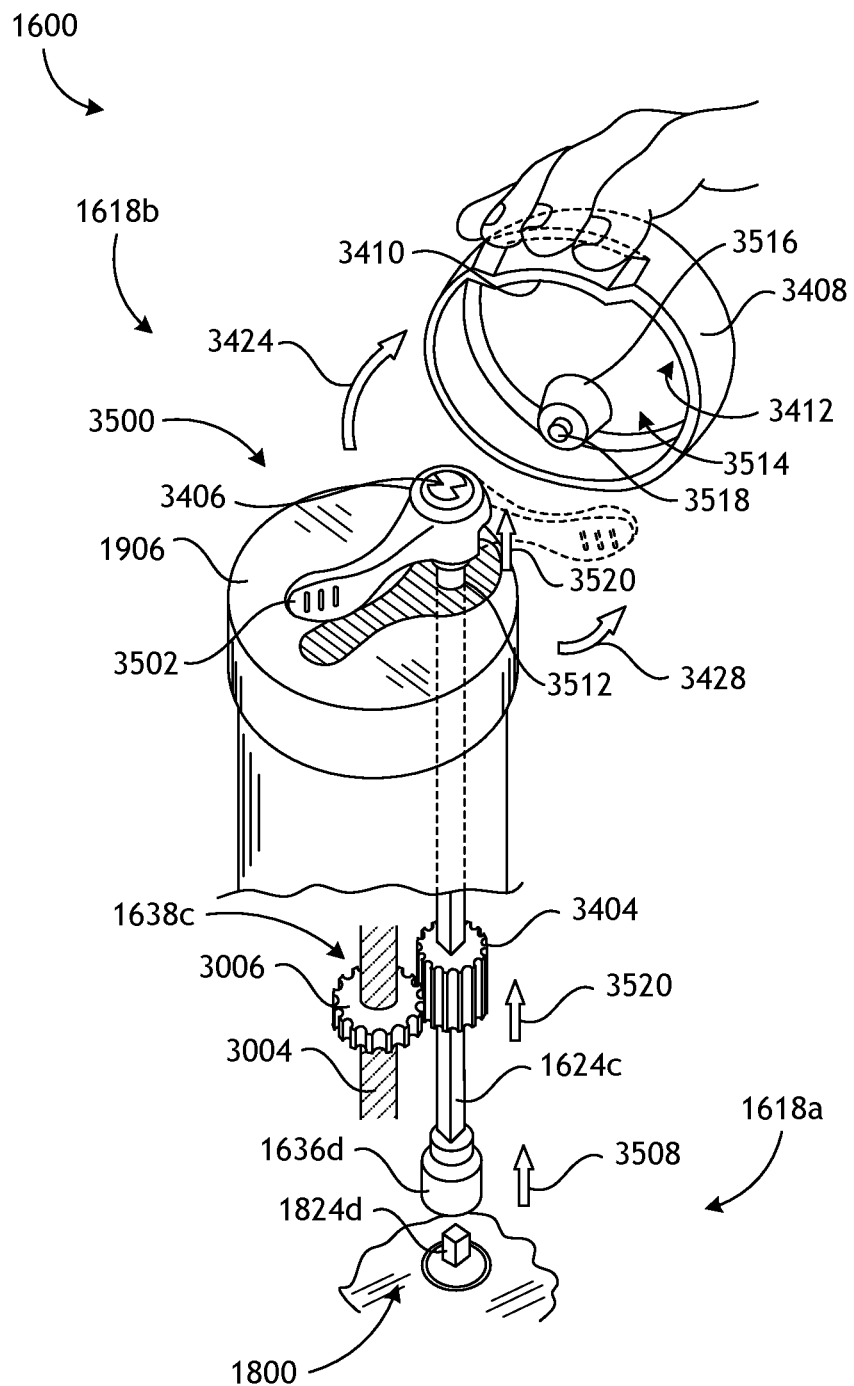

FIGS. 35A-35B illustrate a bailout mechanism for a non-backdrivable motor, according to one or more other embodiments of the present disclosure.

Figure 36:
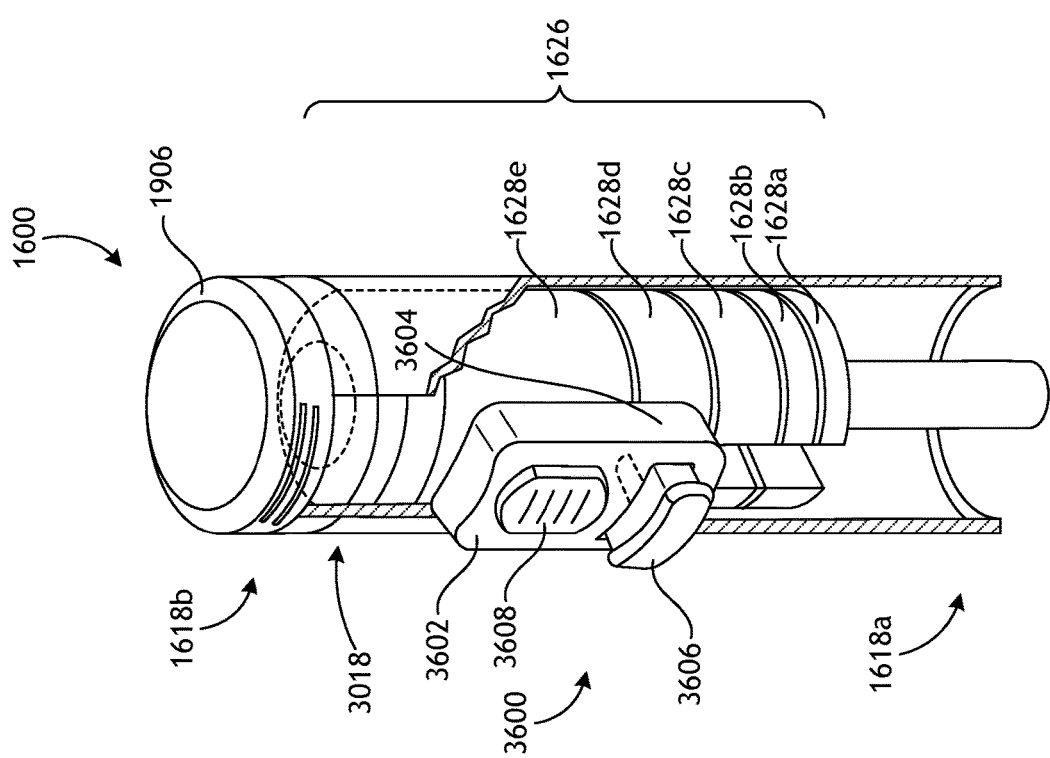

FIG. 36 illustrates user interface mechanism, according to one or more other embodiments of the present disclosure.

Figure 37:
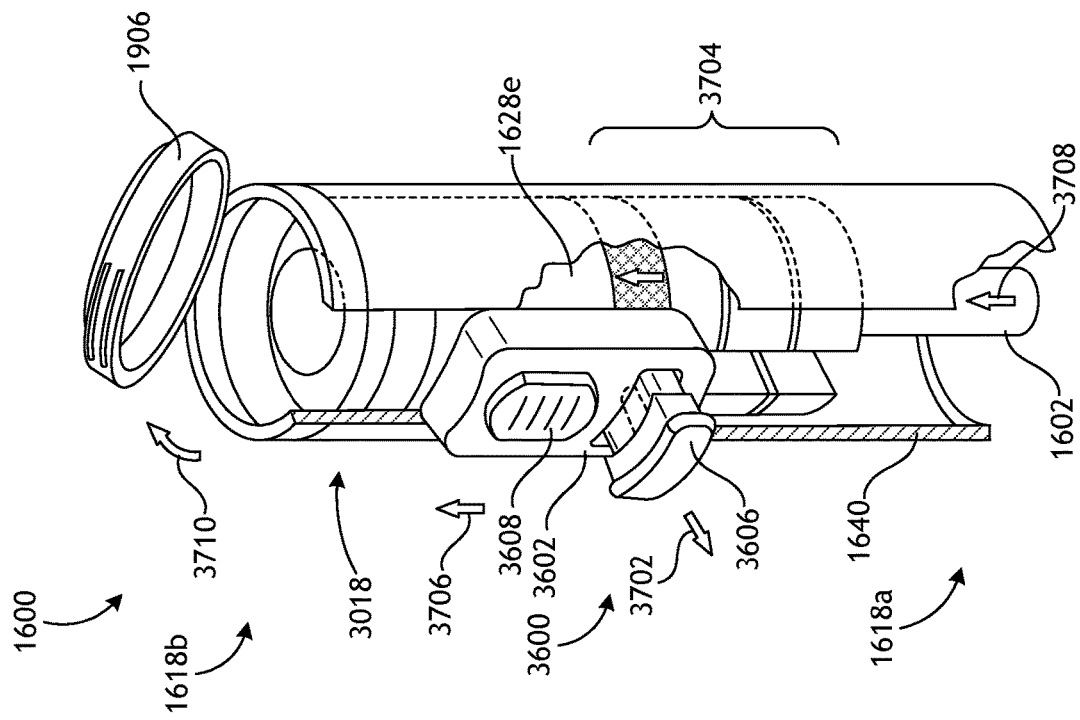

FIG. 37 illustrates example operation of the user interface mechanism of FIG. 36.

Figure 38:
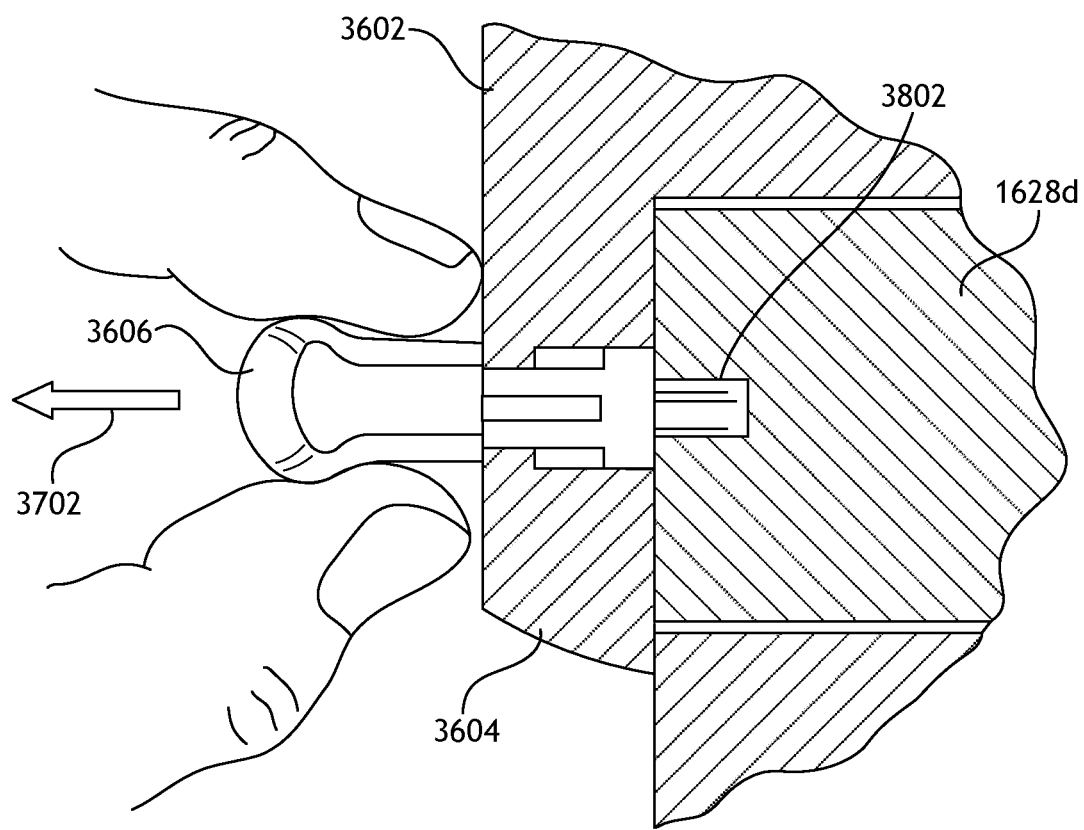

FIG. 38 illustrates a detailed cross-section of user interface mechanism of FIG. 36 when in a locked position.

DETAILED DESCRIPTION

1. Overview

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
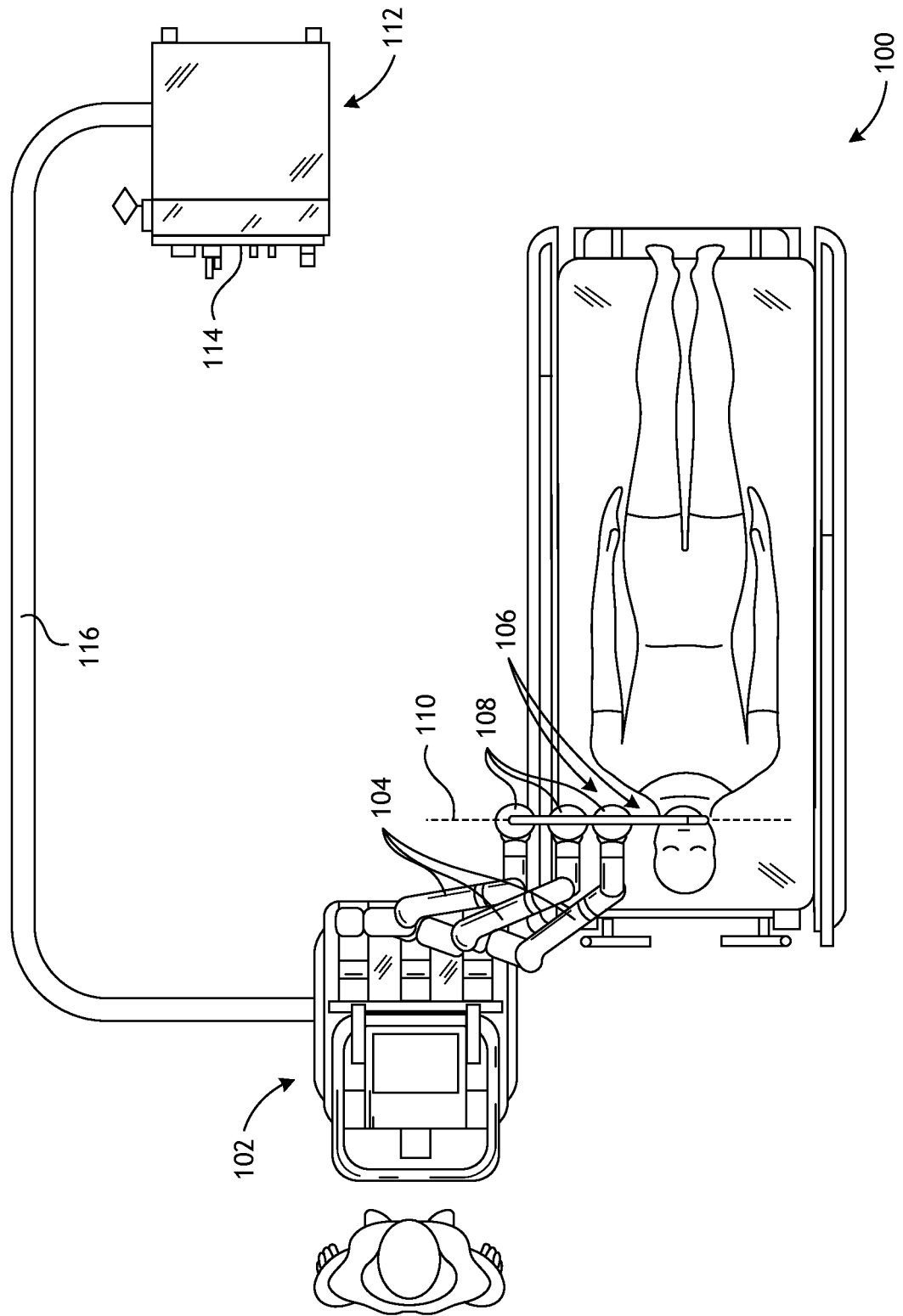
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108 (alternately referred to as "tool drivers"). As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of a medical tool. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
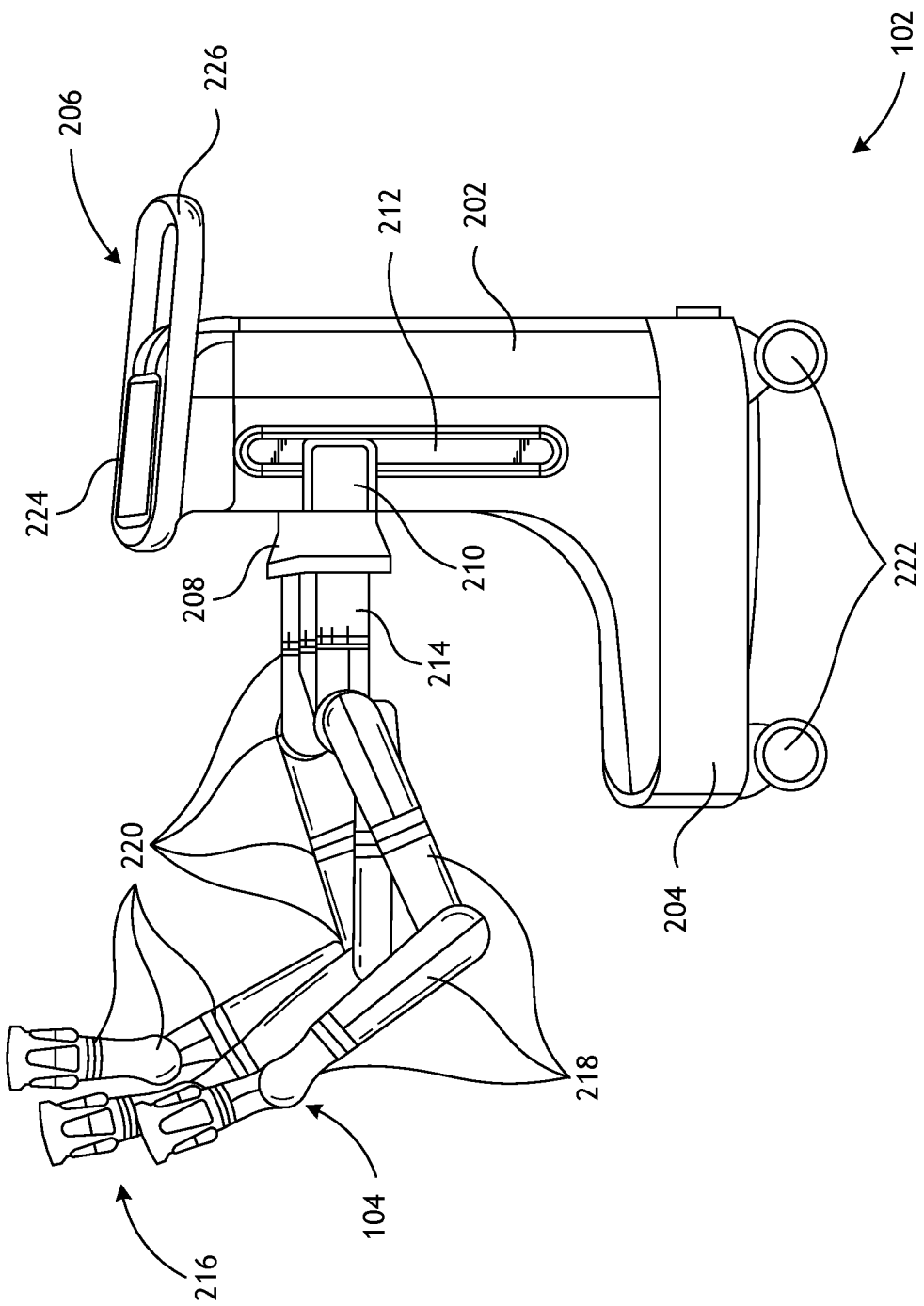
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, that are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, providing seven degrees of freedom. A multitude of joints 220 result in a multitude of degrees of freedom, allowing for "redundant" degrees of freedom. Redundant degrees of freedom allow the robotic arms 104 to position its respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, carriage 208, and arms 104 over the floor. Accordingly, the cart base 204 houses heavier components, such as electronics, motors, power supply, as well as components that either enable movement and/or immobilize the cart. For example, the cart base 204 includes rollable casters 222 that allow for the cart 102 to easily move around a room prior to a procedure. After reaching an appropriate position, the casters 222 may be immobilized using locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
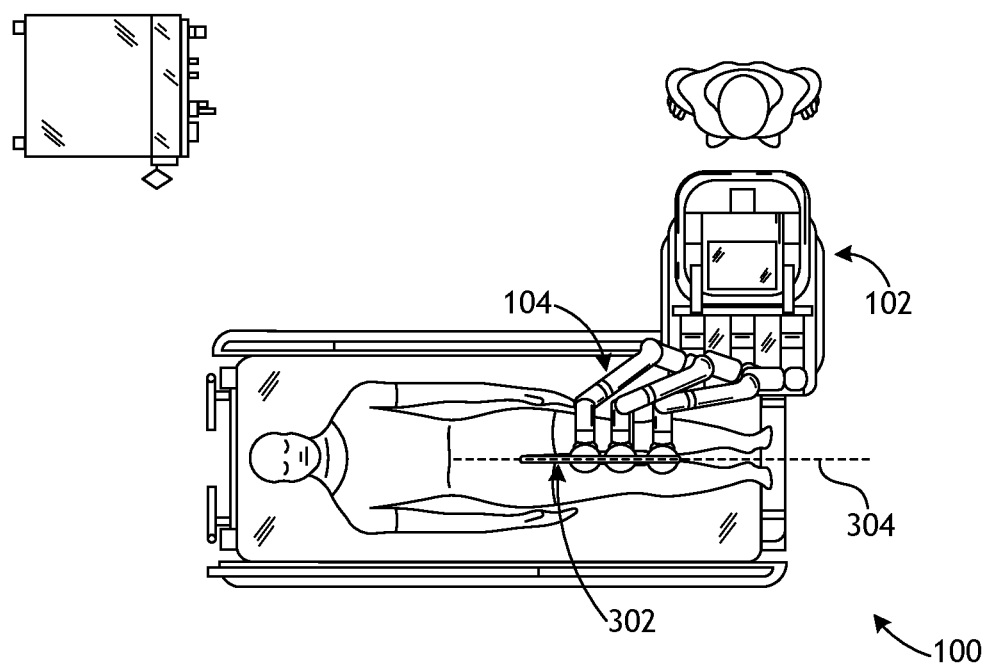
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
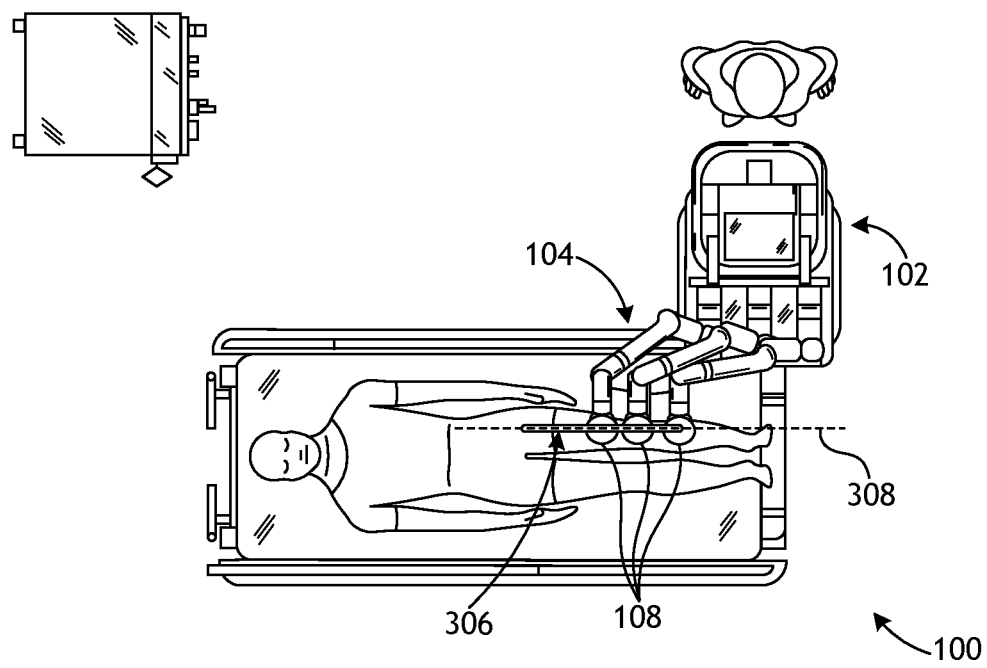
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in an ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
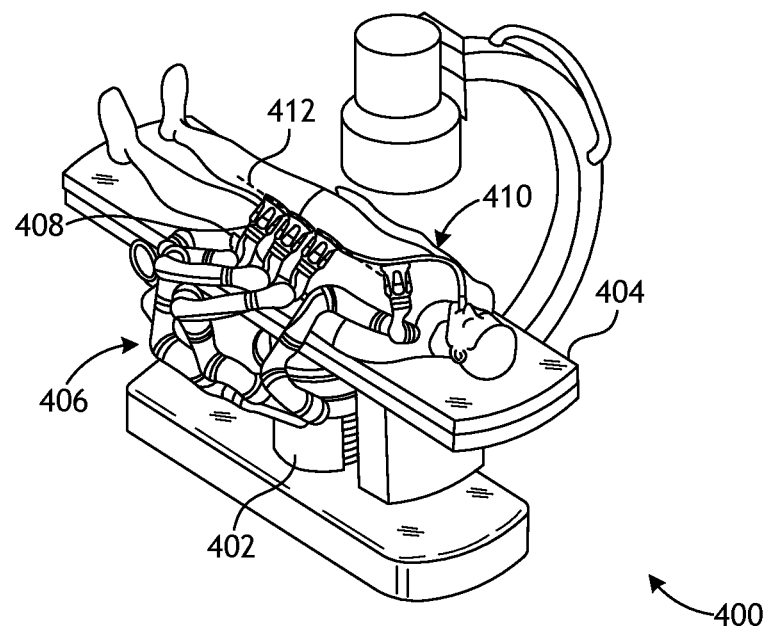
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems 100, end effectors of the robotic arms 406 of the system 400 comprise instrument drivers 408 (alternately referred to as "tool drivers") that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
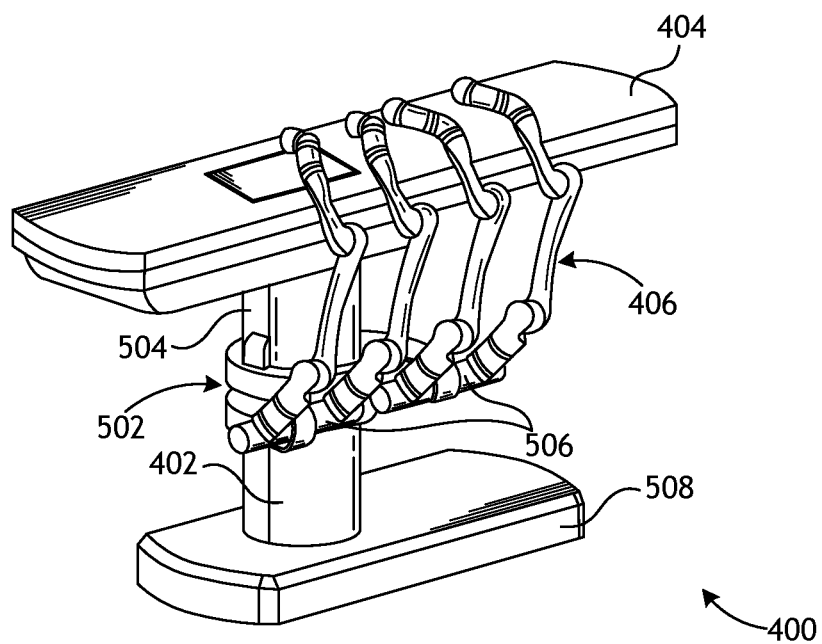
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
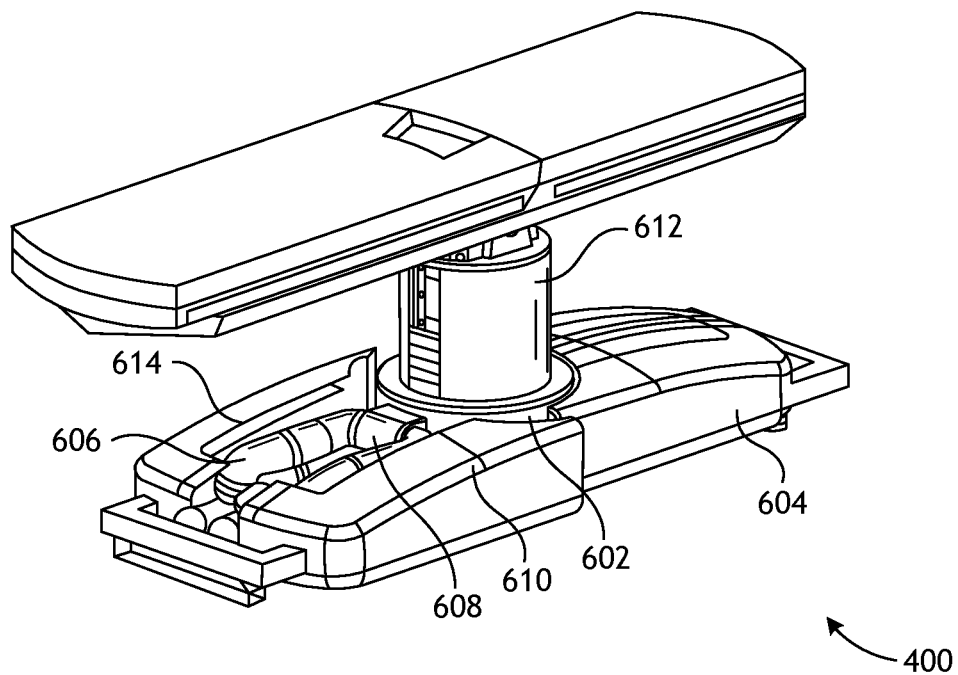
FIG. 6 illustrates an example system configured to stow robotic arm(s).

In some embodiments, a table base may stow and store the robotic arms when not in use. FIG. 6 illustrates an embodiment of the system 400 that is configured to stow robotic arms 606 within a table base 406. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
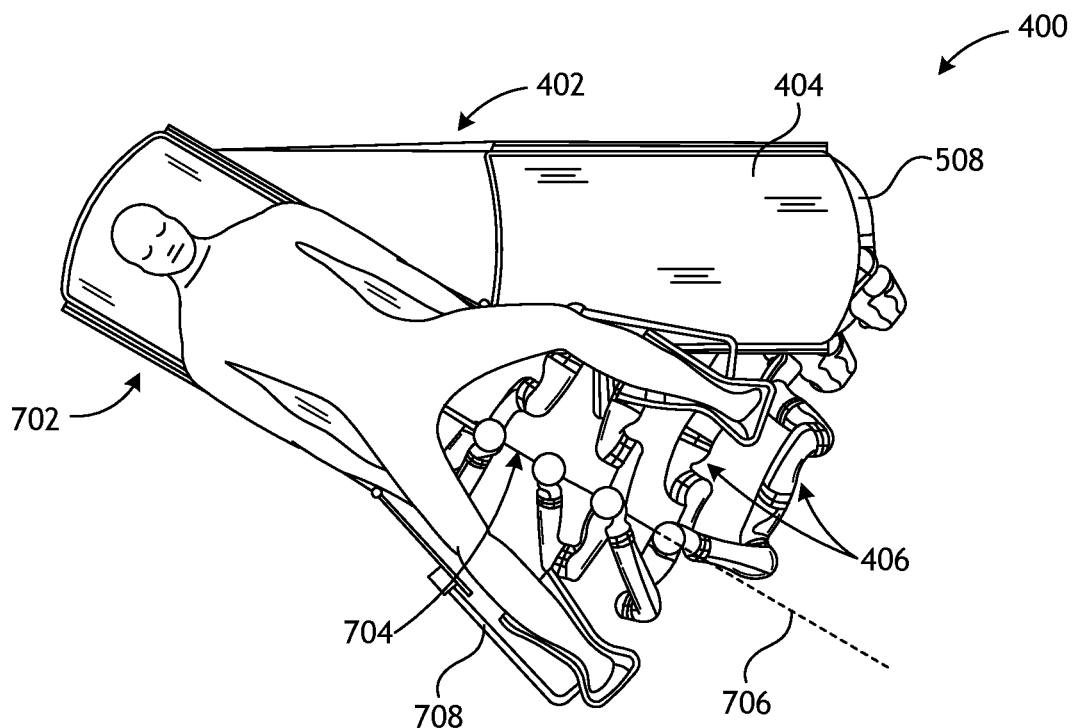
FIG. 7A illustrates an embodiment of a table-based robotic system configured for a ureteroscopy procedure.
Figure 7B:
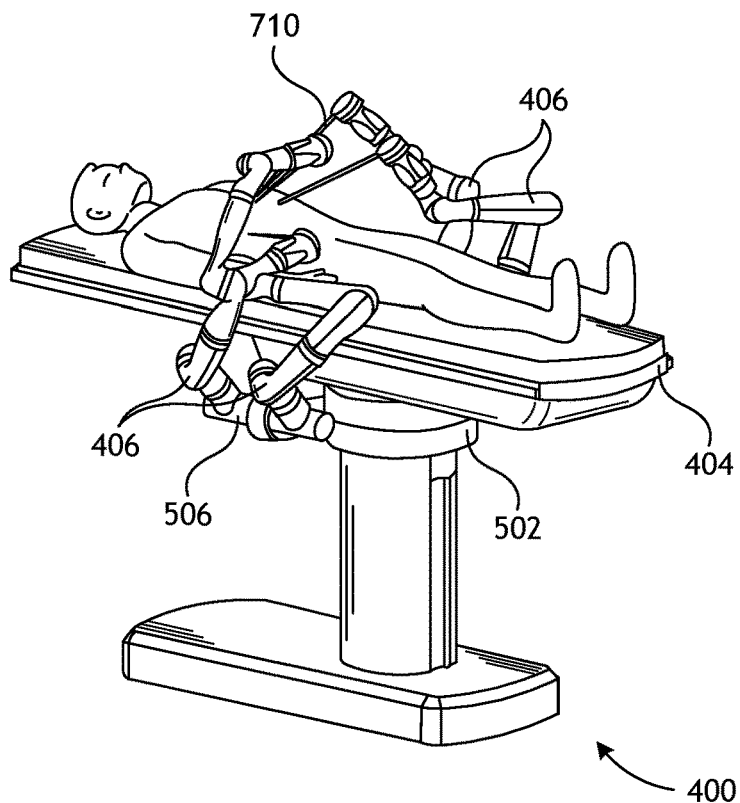
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
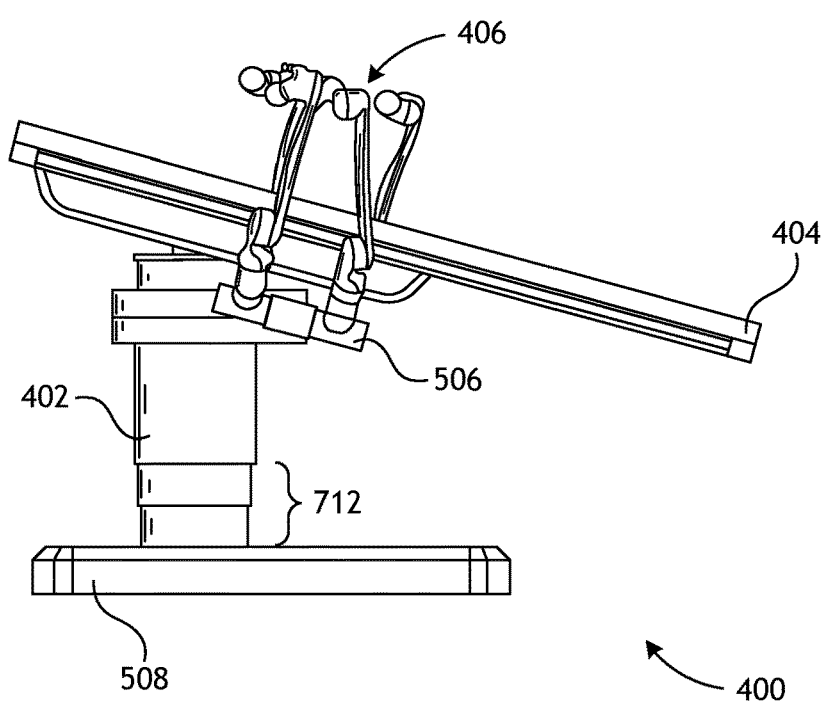
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
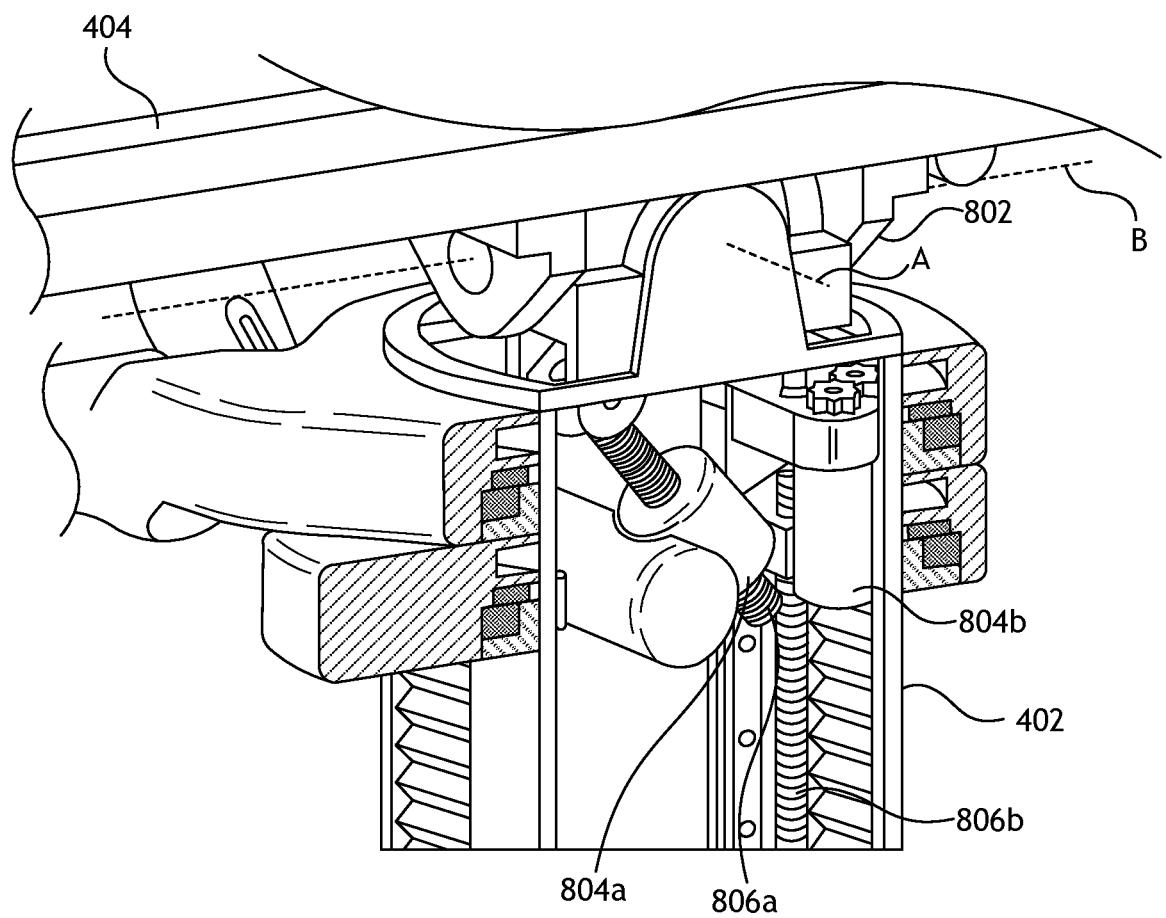
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
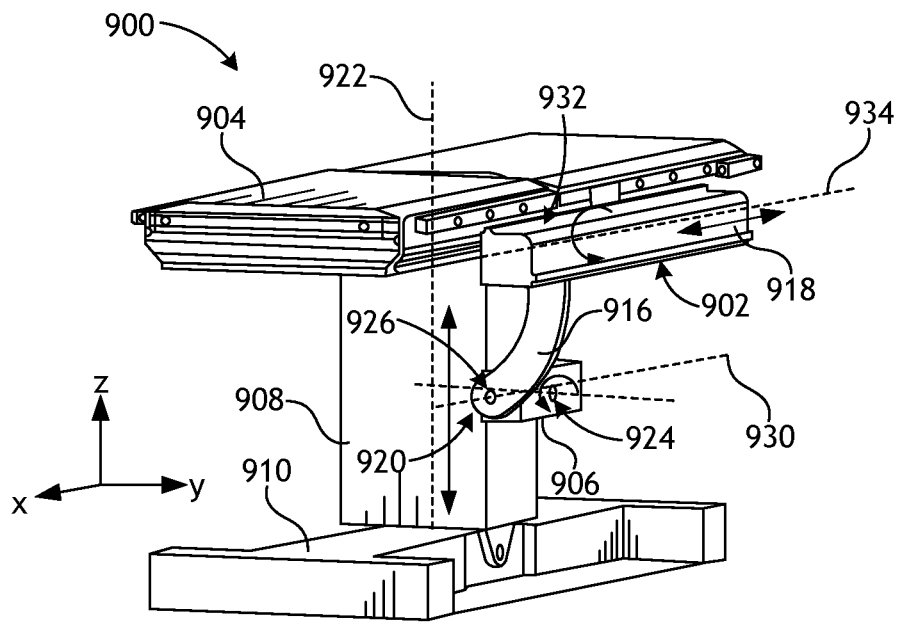
FIG. 9A illustrates an alternative embodiment of a table-based robotic system.
Figure 9B:
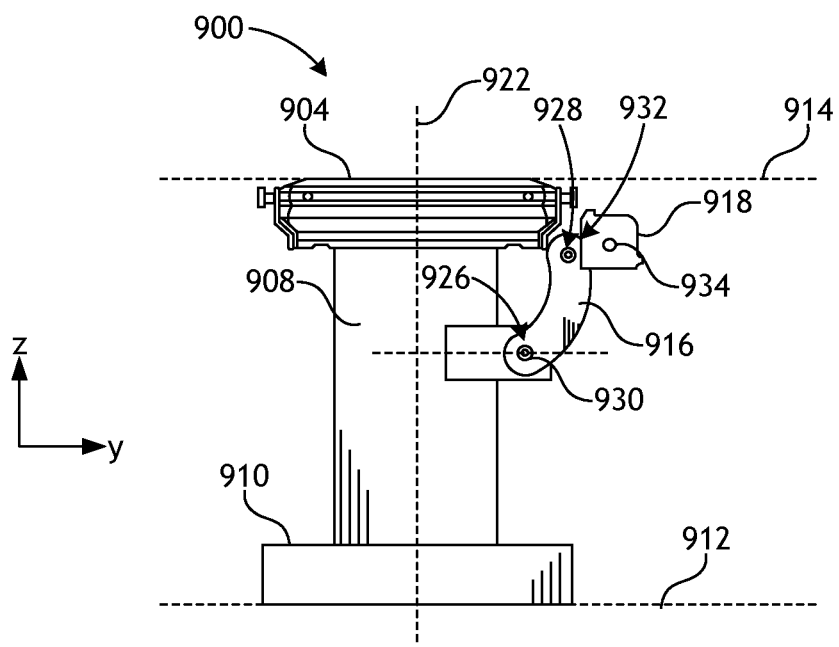
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
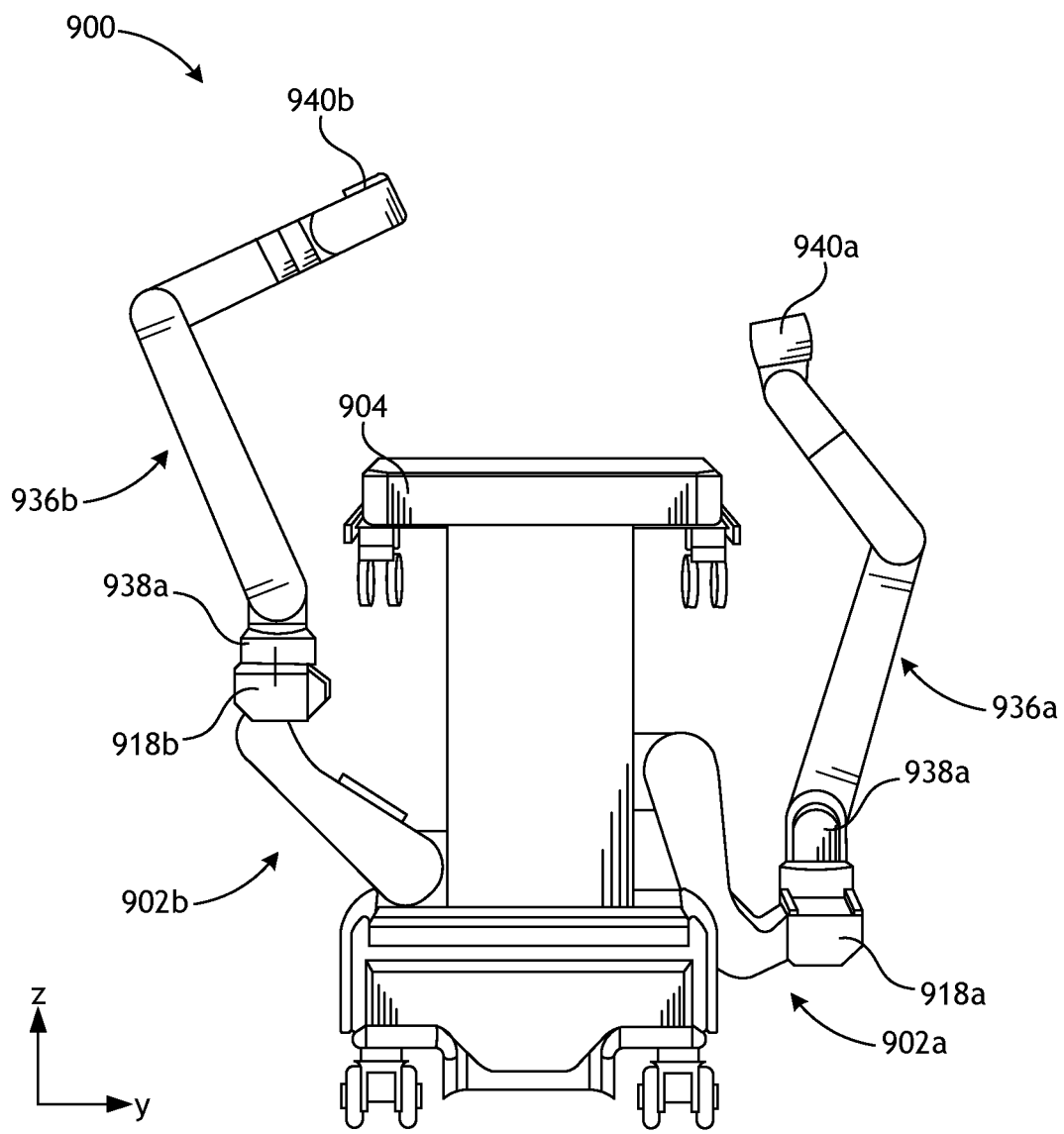
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938*a,b* (1-degree of freedom including translation). In some embodiments, the insertion degree of freedom can be provided by the robotic arm 936*a,b*, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument and, (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
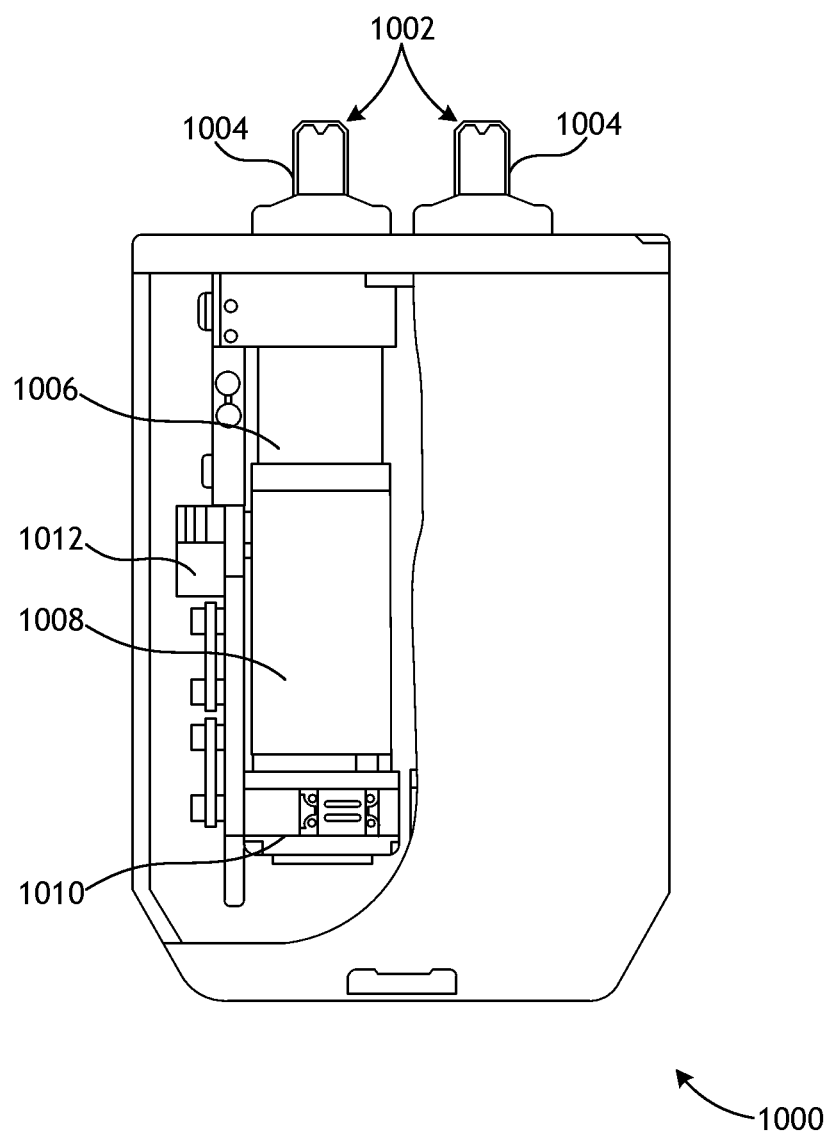
FIG. 10 illustrates an exemplary instrument driver.

FIG. 10 illustrates an example instrument driver 1000, according to one or more embodiments. Positioned at the distal end of a robotic arm, the instrument driver 1000 comprises of one or more drive output 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independent controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
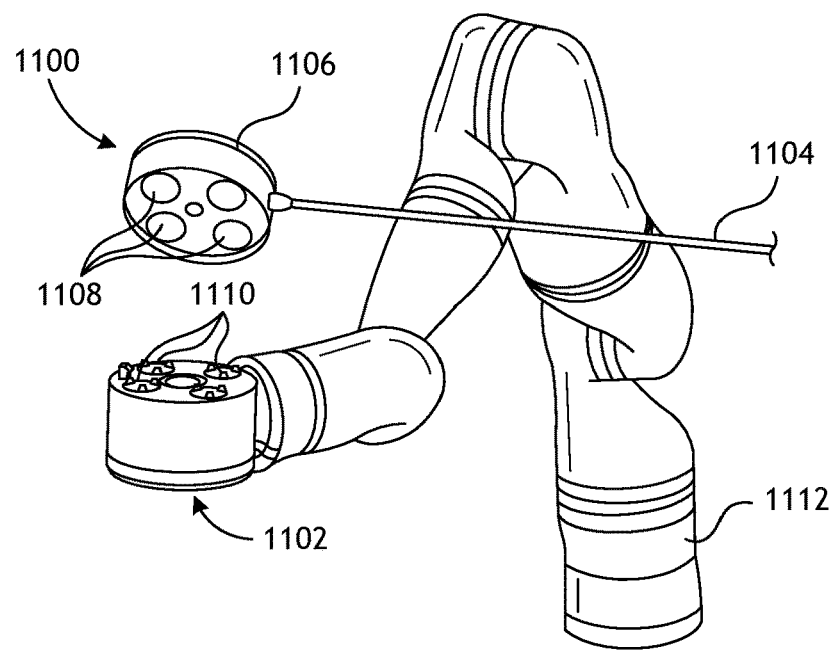
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft 1104 may be connected to an end effector of a surgical tool or medical instrument extending from a jointed wrist formed from a clevis with at least one degree of freedom, such as, for example, a grasper or scissors, that may be actuated based on force from the tendons as the drive inputs 1108 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise of a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
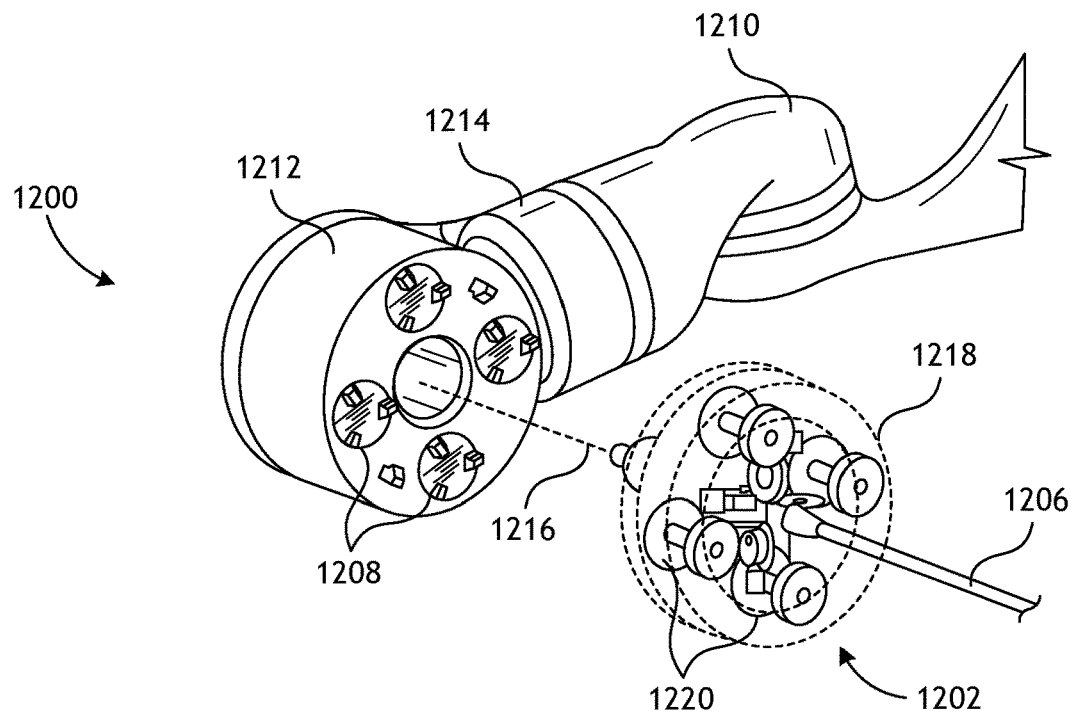
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
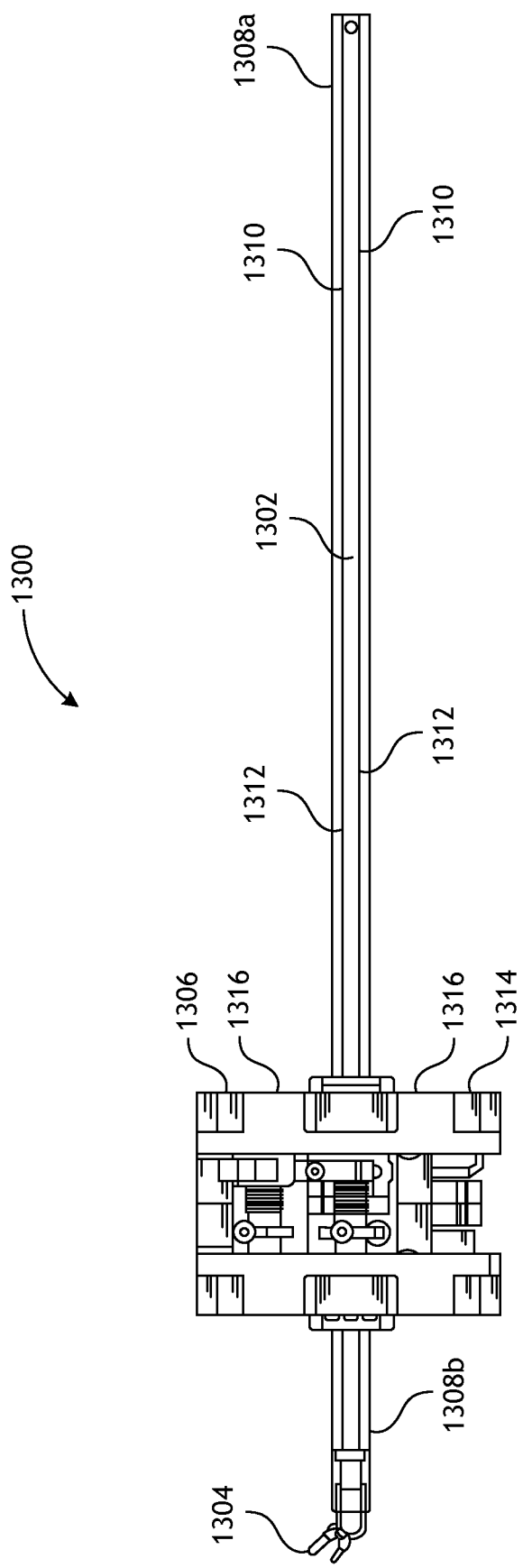
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more torque couplers on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
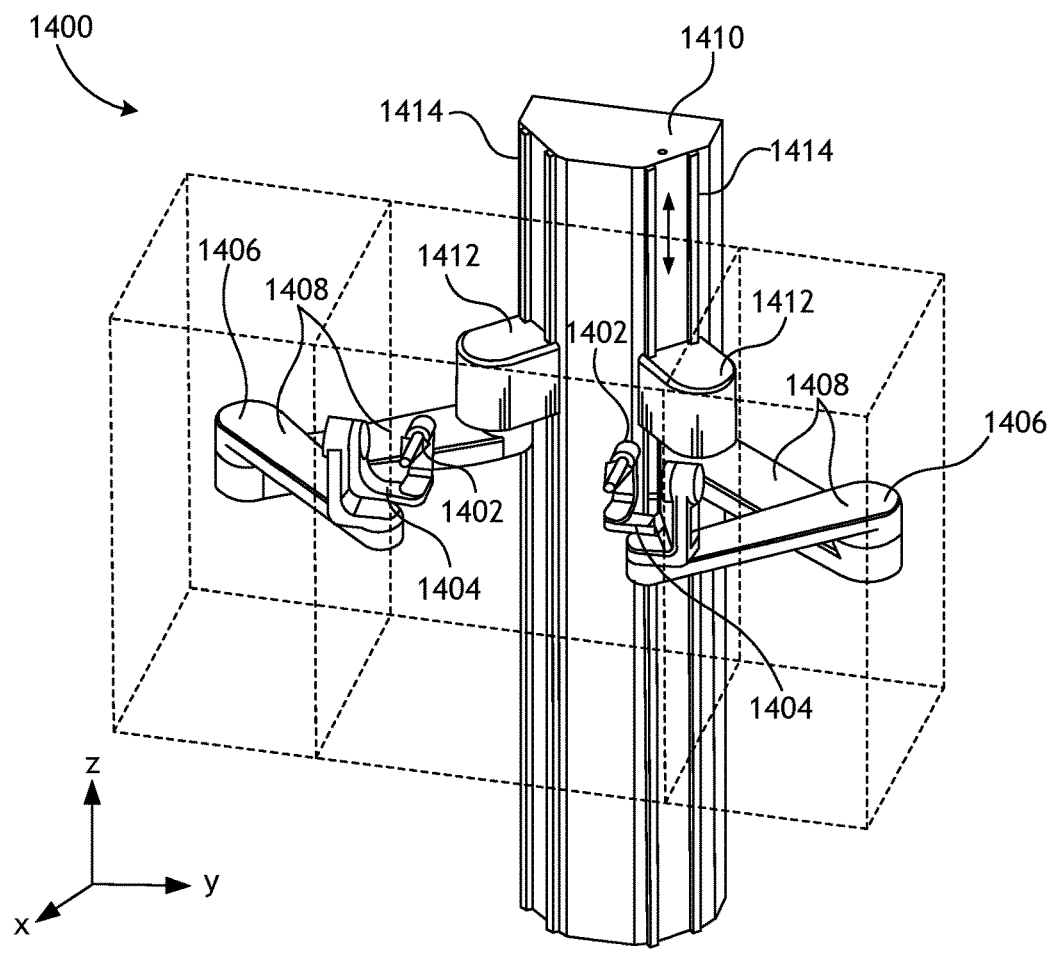
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
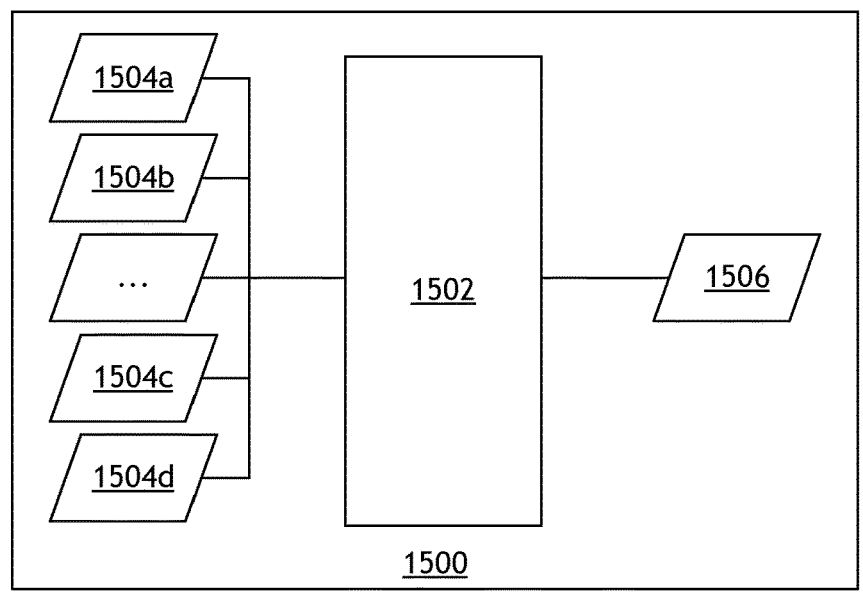
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504b and/or the robotic command and kinematics data 1504d.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction

Embodiments of the disclosure relate to systems and techniques for manually manipulating a surgical tool. The surgical tool may include a fin connected to a carriage within a drive housing and accessible from an exterior of the drive housing to manually translate the carriage, even when the drive housing is installed on an instrument driver arranged at an end of a robotic arm. A user may grasp the fin of a user interface operatively coupled to the drive housing of the surgical tool, manually move the fin along an exterior of the drive housing and thereby moving the carriage within the drive housing, and thereby cause rotation of a drive input on the drive housing.

3. Description

Figure 16:
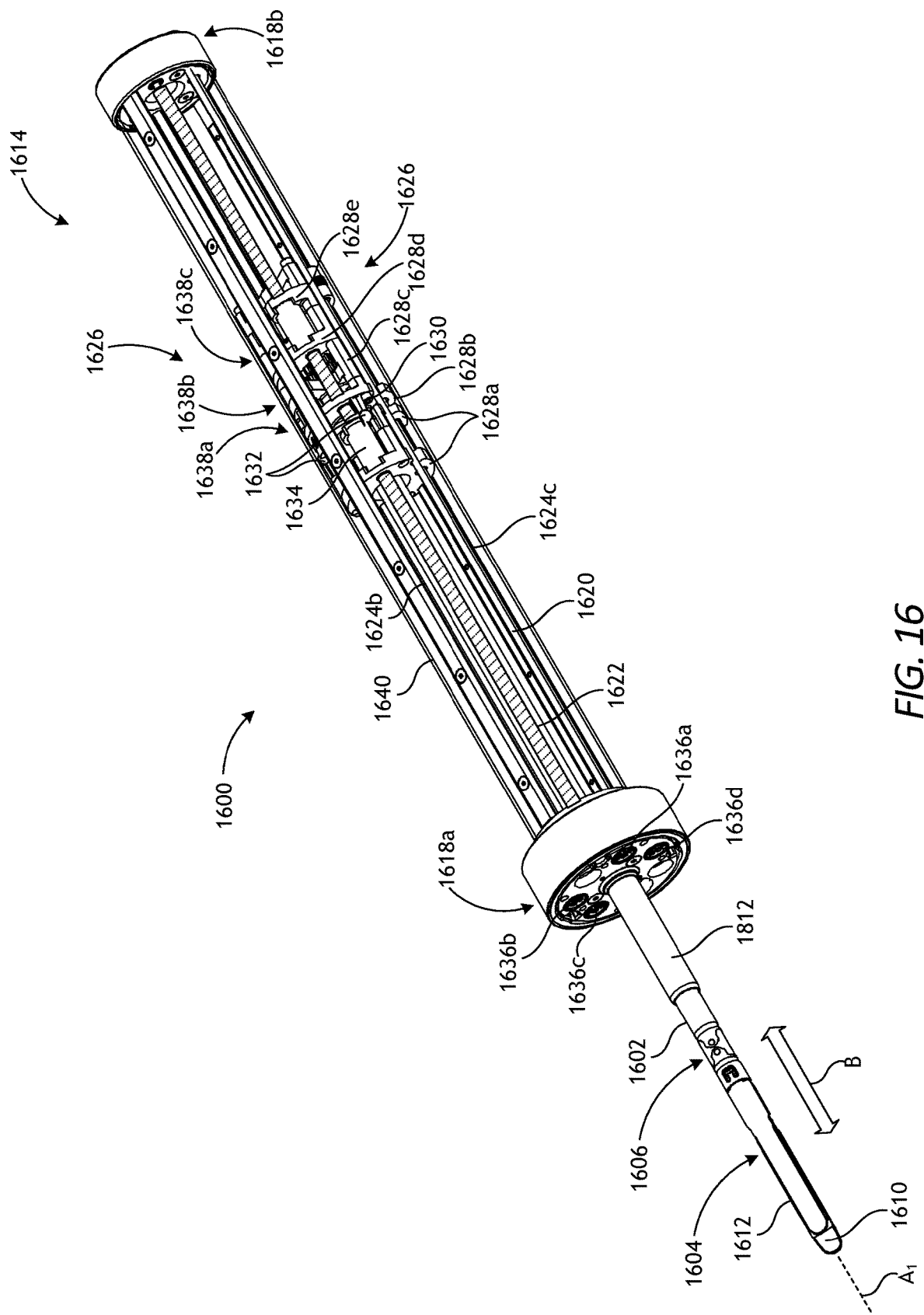
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the medical instruments described above with reference to FIGS. 11-13 and, therefore, may be used in conjunction with a robotic surgical system, such as the robotically-enabled systems 100, 400, and 900 of FIGS. 1-13. As illustrated, the surgical tool 1600 includes an elongated shaft 1602, an end effector 1604 arranged at the distal end of the shaft 1602, and an articulable wrist 1606 (alternately referred to as a "wrist joint") that couples the end effector 1604 to the distal end of the shaft 1602.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue.

As illustrated, the end effector 1604 includes opposing jaws 1610, 1612 configured to move (articulate) between open and closed positions. Alternatively, the end effector 1604 may comprise other types of instruments requiring the opposing jaws 1610, 1612 such as, but not limited to, tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods. Such end effectors or instruments include, but are not limited to, a suction irrigator, an endoscope (e.g., a camera), a probe, a scope, an advanced imaging system, or any combination thereof.

One or both of the jaws 1610, 1612 may be configured to pivot to actuate the end effector 1604 between open and closed positions. In the illustrated example, the second jaw 1612 is rotatable (pivotable) relative to the first jaw 1610 to move between an open, unclamped position and a closed, clamped position. In other embodiments, however, the first jaw 1610 may move (rotate) relative to the second jaw 1612, without departing from the scope of the disclosure. In yet other embodiments, both jaws 1610, 1612 may move to actuate the end effector 1604 between open and closed positions.

In the illustrated example, the first jaw 1610 may be characterized or otherwise referred to as a "cartridge" jaw, and the second jaw 1612 may be characterized or otherwise referred to as an "anvil" jaw. The first jaw 1610 may include a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

In the illustrated embodiment, the pivoting motion at the wrist 1606 is limited to movement in a single plane, e.g., only yaw movement relative to the longitudinal axis $A_1$. The end effector 1604 is depicted in FIG. 16 in the unarticulated position where a longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing 1614, alternately referred to as a "stage," that operates as an actuation system designed to facilitate articulation of the wrist 1606 and actuation (operation) of the end effector 1604 (e.g., clamping, firing, rotation, articulation, energy delivery, etc.). As described in more detail below, the drive housing 1614 includes coupling features that releasably couple the surgical tool 1600 to an instrument driver of a robotic surgical system.

The drive housing 1614 includes a plurality of drive members (obscured in FIG. 16) that extend to the wrist 1606 and the end effector 1604. Selective actuation of some drive members causes the end effector 1604 to articulate (pivot) relative to the shaft 1602 at the wrist 1606. Selective actuation of other drive members cause the end effector 1604 to actuate (operate). Actuating the end effector 1604 may include closing and/or opening the second jaw 1612 relative to the first jaw 1610 (or vice versa), thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot (obscured from view) defined in the first jaw 1610. As it moves distally, the cutting element transects any tissue grasped between the opposing jaws 1610, 1612. Moreover, as the cutting element advances distally, a plurality of staples contained within the staple cartridge (e.g., housed within the first jaw 1610) are urged (cammed) into deforming contact with corresponding anvil surfaces (e.g., pockets) provided on the second jaw 1612. The deployed staples may form multiple rows of staples that seal opposing sides of the transected tissue.

As illustrated, the drive housing 1614 has a first or "distal" end 1618a and a second or "proximal" end 1618b opposite the first end 1618a. The first end 1618a is alternately referred to as the "handle". In some embodiments, one or more struts 1620 (two shown) extend longitudinally between the first and second ends 1618a,b to help fix the distance between the first and second ends 1618a,b and provide structural stability to the drive housing 1614. In other embodiments, however, the struts 1620 may be omitted, without departing from the scope of the disclosure.

A lead screw 1622 and one or more splines 1624 also extend longitudinally between the first and second ends 1618a,b. In the illustrated embodiment, the drive housing 1614 includes a first spline 1624a, a second spline 1624b, and a third spline 1624c. While three splines 1624a-c are depicted, more or less than three may be included in the drive housing 1614, without departing from the scope of the disclosure. Unlike the struts 1620, the lead screw 1622 and the splines 1624a-c are rotatably mounted to the first and second ends 1618a,b. As described in more detail below, selective rotation of the lead screw 1622 and the splines 1624a-c causes actuation of various components within the drive housing 1614, which thereby causes various functions of the surgical tool 1600 to transpire, for example, such as translating the end effector 1604 along the longitudinal axis $A_1$, causing the end effector 1604 to articulate (pivot) at the wrist 1606, and causing the end effector 1604 to actuate (operate).

The drive housing 1614 further includes a carriage or kart 1626 movably mounted along the lead screw 1622 and the splines 1624a-c and housing various activating mechanisms configured to cause operation of specific functions of the end effector 1604. The carriage 1626 may comprise two or more layers, shown in FIG. 16 as a first layer 1628a, a second layer 1628b, a third layer 1628c, a fourth layer 1628d, and a fifth layer 1628e. While five layers 1628a-e are depicted, more or less than five may be included in the carriage 1626, without departing from the scope of the disclosure.

In addition, one or more of the layers 1628a-e of the carriage 1626 may be detachable relative to the remaining layers 1628a-e. In this manner, one or more of the layers 1628a-e of the carriage 1626 may be secured together as a block of layers that may be releasably secured to the remaining layer(s) to define the carriage 1628. For example, some of the layers 1628a-e may be integrally secured together in series, to form a block of layers, and such block of layers may be selectively secured to the remaining one or more layers 1628a-e that are not integrally secured to the block of layers. In the illustrated embodiment, the layers 1628b-e are secured to each other in series using one or more mechanical fasteners 1630 (one visible) extending between the second layer 1628b and the fifth layer 1628e and through coaxially aligned holes in each layer 1628b-e to form a block of layers configured to be releasably secured to the first layer 1628a, as described below. In the illustrated example, one or more snaps 1632 (two visible) are utilized to align (or clock) and releasably attach the block of layers 1628b-e to the first layer 1628a, as further described below, but various other types of one or more releasable connector(s) may be utilized.

While four layers 1628b-e are depicted as being secured together via the mechanical fastener(s) 1630 to define the block of secured-together layers 1628b-e releasably attached to the first layer 1628a via the snaps 1632, the block of secured-together layers may include more or less than four layers, without departing from the scope of the disclosure. Moreover, one or more additional layers may be mechanically fastened in series to the first layer 1628a (e.g., the second layer 1628b) to define a second block of secured-together layers that is releasably attached to the first block of secured-together layers (e.g., the three layers 1628c-e), without departing from the scope of the disclosure. As further described below, configuring the carriage 1626 with one or more layers that are releasably secured relative to the remaining layers will provide a degree of modularity to the surgical tool 1600 to thereby allow one or more components of the surgical tool 1600 to be interchangeable, reusable, and/or replaceable.

The shaft 1602 is coupled to and extends distally from the carriage 1626 through the first end 1618a of the drive housing 1614. In the illustrated embodiment, for example, the shaft 1602 penetrates the first end 1618a at a central aperture defined through the first end 1618a. The carriage 1626 is movable between the first and second ends 1618a,b along the longitudinal axis $A_1$ and is thereby able to advance or retract the end effector 1604 relative to the drive housing 1614, as indicated by the arrows B. More specifically, in some embodiments, the carriage 1626 includes a carriage nut 1634 mounted to the lead screw 1622 and secured with respect to the first layer 1628a. In this manner, the first layer 1628a of the carriage 1626 may define an elevator upon which the other layers 1628b-e releasably attached thereon may be translated, as described below. The outer surface of the lead screw 1622 defines helical threading and the carriage nut 1634 defines corresponding internal helical threading (not shown) matable with the outer helical threading of the lead screw 1622. As a result, rotation of the lead screw 1622 causes the carriage nut 1634 to advance or retract the carriage 1626 along the longitudinal axis $A_1$ and correspondingly advance or retract the end effector 1604 relative to the drive housing 1614.

As indicated above, the lead screw 1622 and the splines 1624a-c are rotatably mounted to the first and second ends 1618a,b. More specifically, the first end 1618a of the drive housing 1614 may include one or more rotatable drive inputs, shown as a first drive input 1636a, a second drive input 1636b, a third drive input 1636c, and a fourth drive input 1636d. As discussed in more detail below, each drive input 1636a-d may be matable with a corresponding drive output of an instrument driver such that movement (rotation) of a given drive output correspondingly moves (rotates) the associated drive input 1636a-d.

The first drive input 1636a may be operatively coupled to the lead screw 1622 such that rotation of the first drive input 1636a correspondingly rotates the lead screw 1622, which causes the carriage nut 1634 and the first layer 1628a constraining the carriage nut 1634 to advance or retract along the longitudinal axis $A_1$, depending on the rotational direction of the lead screw 1622. Moreover, as described herein the first layer 1628a of the carriage 1626 may be configured as an elevator (of the carriage 1626) that translates the remaining layers 1628b-e of the carriage 1626 releasably connected to the first layer 1628a. Thus, when the remaining layers 1628b-e are installed on the first layer 1628a, to thereby define the carriage 1626 as depicted in FIG. 16, rotation of the first drive input 1636a correspondingly rotates the lead screw 1622, which causes the entirety of the carriage 1626 now fully coupled to the carriage nut 1634, to advance or retract along the longitudinal axis $A_1$, depending on the rotational direction of the lead screw 1622.

The second drive input 1636b may be operatively coupled to the first spline 1624a such that rotation of the second drive input 1636b correspondingly rotates the first spline 1624a. In some embodiments, the first spline 1624a may be operatively coupled to a first activating mechanism 1638a of the carriage 1626, and the first activating mechanism 1638a may be operable to open and close the jaws 1610, 1612. Accordingly, rotating the second drive input 1636b will correspondingly actuate the first activating mechanism 1638a and open or close the jaws 1610, 1612, depending on the rotational direction of the first spline 1624a. In addition, the second layer 1628b is configured to accommodate the first activating mechanism 1638a such that the jaws 1610, 1612 are operable as described herein and, in the illustrated example, the first activating mechanism 1638a is at least partially constrained by the second layer 1628b and the third layer 1628c.

The third drive input 1636c may be operatively coupled to the second spline 1624b such that rotation of the third drive input 1636c correspondingly rotates the second spline 1624b. In some embodiments, the second spline 1624b may be operatively coupled to a second activating mechanism 1638b of the carriage 1626, and the second activating mechanism 1638b may be operable to articulate the end effector 1604 at the wrist 1606. Accordingly, rotating the third drive input 1636c will correspondingly actuate the second activating mechanism 1638b and cause the wrist 1606 to articulate in at least one degree of freedom, depending on the rotational direction of the second spline 1624b. In addition, the third layer 1628c is configured to accommodate the second activating mechanism 1638b for articulation of the wrist 1606 as described herein and, in the illustrated example, the second activating mechanism 1638b is at least partially constrained by the third layer 1628c and the fourth layer 1628d.

The fourth drive input 1636d may be operatively coupled to the third spline 1624c such that rotation of the fourth drive input 1636d correspondingly rotates the third spline 1624c. In some embodiments, the third spline 1624c may be operatively coupled to a third activating mechanism 1638c of the carriage 1626, and the third activating mechanism 1638c may be operable to translate a drive bar (see FIGS. 30-31) extending within the elongate shaft 1602 and thereby fire the cutting element (knife) at the end effector 1604. Accordingly, rotating the fourth drive input 1636d will correspondingly actuate the third activating mechanism 1638c and cause the knife to advance or retract, depending on the rotational direction of the third spline 1624c. In addition, the fifth layer 1628e is configured to accommodate the third activating mechanism 1638c for firing the cutting element of the end effector 1604 as described herein and, in the illustrated example, the third activating mechanism 1638c is at least partially constrained by the fifth layer 1628e and a thrust bearing layer 1628f of the carriage 1626.

In the illustrated embodiment, the activating mechanisms 1638a-c comprise intermeshed gearing assemblies including one or more drive gears driven by rotation of the corresponding spline 1624a-c and configured to drive one or more corresponding driven gears that cause operation of specific functions of the end effector 1604.

In some embodiments, the layers 1628b-e are secured to the shaft 1602 and the activating mechanisms 1638a-c are operatively housed within their associated layer 1628b-e so as to actuate the surgical tool 1600 as described herein. In the illustrated embodiment, the layers 1628b-e are fastened together with the mechanical fastener(s) 1630 to constrain the associated activating mechanisms 1638a-c in positions where they intermesh to provide functionality at the end effector 1604 and the wrist 1606. Here, the first layer 1628a of the carriage 1626, the lead screw 1622, and the carriage nut 1634 are operatively secured within (or to) the drive housing 1614, such that the first layer 1628a defines an elevator onto which the other layers 1628b-e may be releasably secured when assembly the surgical tool 1600.

FIG. 16 illustrates an embodiment of the drive housing 1614 having a shroud 1640 that defines a periphery of the drive housing 1614 for handling and manipulation by the operator or user. In the illustrated embodiment, the shroud 1640 is depicted as a transparent material (or at least a partially transparent material), such that the internal components of the drive housing 1614 are visible through the shroud 1640. However, in other examples, the shroud 1640 need not be transparent. Where included, the shroud 1640 may be sized to receive the lead screw 1622, the splines 1624a-c, and the carriage 1626, as well as other internal components of the drive housing 1614.

Figure 17:
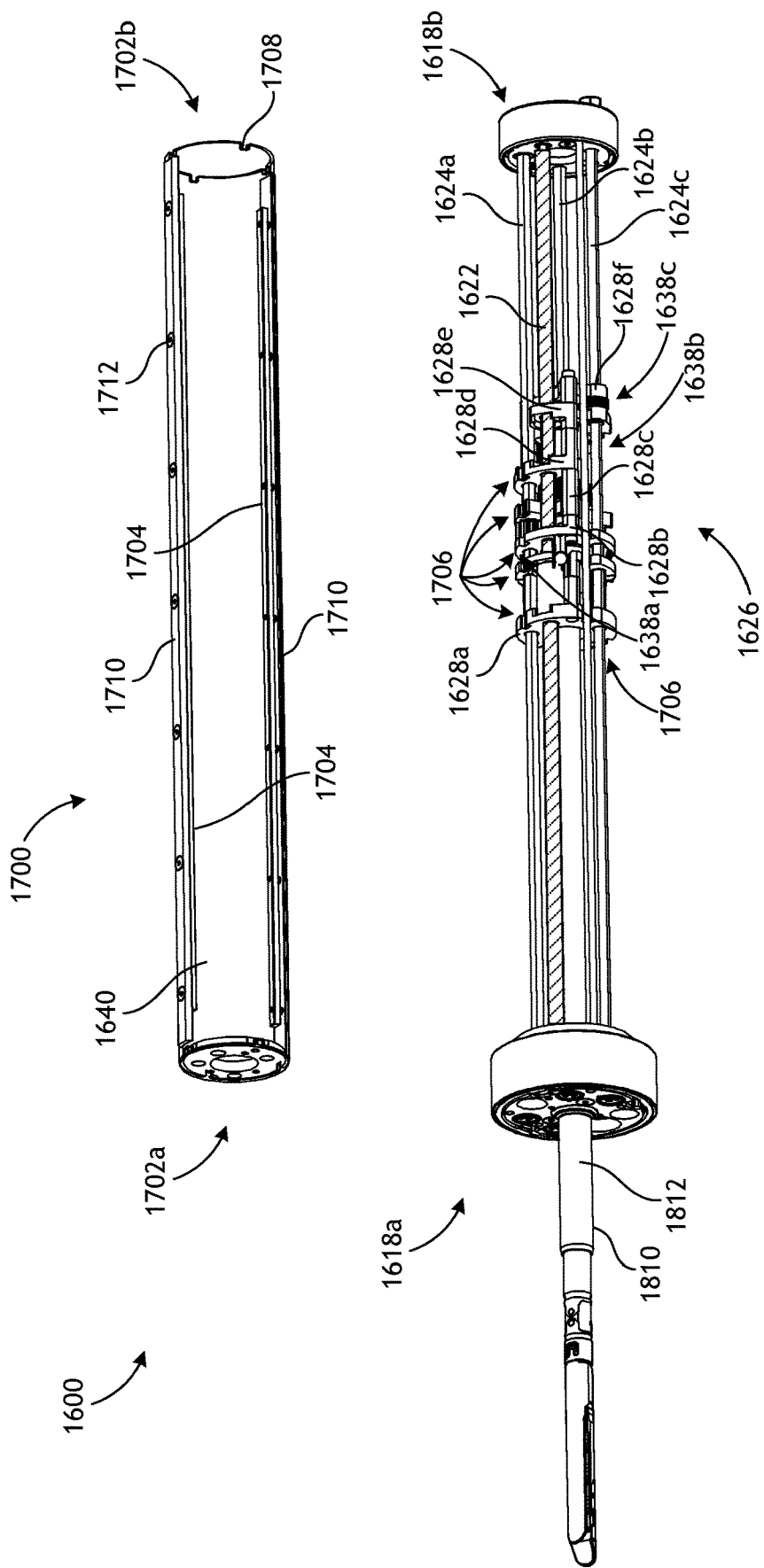
FIG. 17 is an isometric view of the surgical tool of FIG. 16 when unassembled from its shroud assembly, according to one or more embodiments.

In some embodiments, the shroud 1640 may be incorporated in a shroud assembly of the drive housing 1614. FIG. 17 is an isometric view of the surgical tool 1600 of FIG. 16 illustrating the drive housing 1614 when partially disassembled, according to one or more embodiments. In particular, FIG. 17 depicts an exemplary shroud assembly 1700 of the drive housing 1614 incorporating the shroud 1640 when disassembled from the remaining portion of the drive housing 1614, according to one or more embodiments. In the illustrated embodiment, the shroud assembly 1700 defines a tubular or cylindrical structure having (i) a first end 1702a matable with the first end 1618a of the drive housing 1614 and (ii) a second end 1702b opposite the first end 1702a and matable with the second end 1618b of the drive housing 1614. The carriage 1626, the lead screw 1622, and the splines 1624a-c may all be accommodated within the interior of the shroud 1640, and the carriage 1626 may engage and ride on one or more rails 1704 (sometimes referred to as guide rails) coupled to the shroud 1640. The rails 1704 extend longitudinally and parallel to the lead screw 1622, and the rails 1704 are sized to be received within corresponding notches 1706 defined on the outer periphery of the carriage 1626 and, more particularly, on one or more of the layers 1628a-e. As the carriage 1626 translates along the longitudinal axis $A_1$, the rails 1704 help maintain the angular position of the carriage 1626 and assume any torsional loading that would otherwise adversely affect the carriage 1626. In addition, the shroud 1640 may include one or more alignment notches 1708 for aligning the second end 1618b on the shroud assembly 1700. The rails 1704 may be fastened within an interior of the shroud 1640 and, in the illustrated examples, are coupled within the interior of the shroud 1640 via exterior rails 1710 positioned exterior the shroud 1640 and connected to the (guide) rails 1704 via a plurality of fasteners 1712 that extend through the shroud 1640.

Figure 18A:
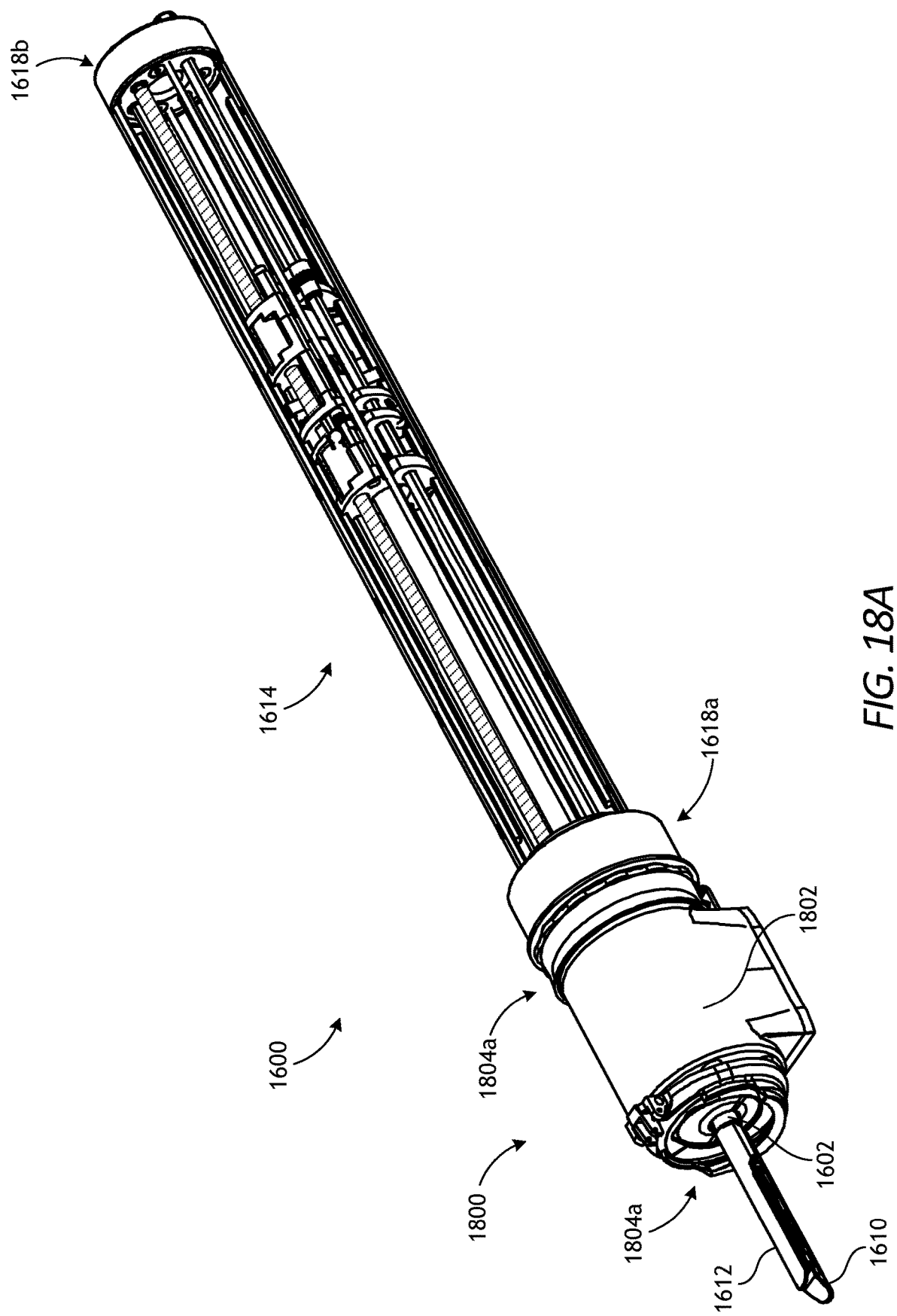
FIG. 18A is an isometric view of the surgical tool of FIGS. 16-17 releasably coupled to an example instrument driver, according to one or more embodiments.

FIG. 18A is an isometric view of the surgical tool 1600 of FIGS. 16 and 17 releasably coupled to an example instrument driver 1800, according to one or more embodiments. The instrument driver 1800 may be similar in some respects to the instrument drivers 1102, 1200 of FIGS. 11 and 12, respectively, and therefore may be best understood with reference thereto. Similar to the instrument drivers 1102, 1200, for example, the instrument driver 1800 may be mounted to or otherwise positioned at the end of a robotic arm (not shown) and designed to provide the motive forces required to operate the surgical tool 1600. Unlike the instrument drivers 1102, 1200, however, the shaft 1602 of the surgical tool 1600 extends through and penetrates the instrument driver 1800.

The instrument driver 1800 has a body 1802 having a first or "proximal" end 1804a and a second or "distal" end 1804b opposite the first end 1804a. In the illustrated embodiment, the first end 1804a of the instrument driver 1800 is matable with the first end 1618a of the drive housing 1614, and the shaft 1602 of the surgical tool 1602 extends into the first end 1804a, through the body 1802, and distally from the second end 1804b of the body 1802.

FIG. 18B provides separated isometric end views of the first end 1804a of the instrument driver 1800 and the first end 1618a of the drive housing 1614 of the surgical tool 1600 of FIGS. 16 and 17. With the jaws 1610, 1612 closed, the shaft 1602 and the end effector 1604 are designed to penetrate the instrument driver 1800 by extending through a central aperture 1806 defined longitudinally through the body 1802 between the first and second ends 1804a,b. To angularly align the surgical tool 1600 with the instrument driver 1800 in a proper angular orientation, one or more alignment guides 1808 may be provided or otherwise defined within the central aperture 1806 and configured to engage one or more corresponding alignment features 1810 provided by the surgical tool 1600 (obscured from view, see FIG. 17). In the illustrated embodiment, the alignment feature 1810 comprises a protrusion or projection defined on or otherwise provided by an alignment nozzle 1812 extending distally from the first end 1618a of the drive housing 1614. In one or more embodiments, the alignment guide 1808 may comprise a curved or arcuate shoulder configured to receive the alignment feature 1810 as the shaft 1602 enters the central aperture 1806 and guide the surgical tool 1600 to a proper angular alignment with the instrument driver 1800 as the shaft 1602 is advanced distally through the central aperture 1806.

In addition, one or more additional alignment features 1814 may be arranged within the central aperture 1806 and configured to mate with one or more corresponding recesses (not illustrated) provided on the alignment nozzle 1812 for ensuring the surgical tool 1600 is installed at a proper rotational alignment with respect to the instrument driver 1800.

As illustrated, a drive interface 1816 is provided at the first end 1804a of the instrument driver 1800, and a driven interface 1818 is provided at the first end 1618a of the drive housing 1614. The driver and driven interfaces 1816, 1818 may be configured to mechanically, magnetically, and/or electrically couple the drive housing 1614 to the instrument driver 1800. To accomplish this, the driver and driven interfaces 1816, 1818 may provide one or more matable locating features configured to secure the drive housing 1614 to the instrument driver 1800. In the illustrated embodiment, for example, the drive interface 1816 provides one or more interlocking features 1820 (three shown) configured to locate and mate with one or more substantially complimentary shaped pockets 1822 (three shown) provided on the driven interface 1818. The interlocking features 1820, exemplified as bulbous protrusions, may be configured to align and mate with the pockets 1822 via an interference or snap fit engagement, for example.

The instrument driver 1800 also includes one or more drive outputs that extend through the drive interface 1816 to mate with the drive inputs 1636a-d provided on the driven face 1818 at the first end 1618a of the drive housing 1614. More specifically, in the illustrated embodiment, the drive interface 1816 of the instrument driver 1800 includes a first drive output 1824a matable with the first drive input 1636a, a second drive output 1824b matable with the second drive input 1636b, a third drive output 1824c matable with the third drive input 1636c, and a fourth drive output 1824d matable with the fourth drive input 1636d. In some embodiments, as illustrated, the drive outputs 1824a-d may comprise splines designed to mate with corresponding splined receptacles on the drive inputs 1636a-d. Once properly mated, the drive inputs 1636a-d will share axes of rotation with the corresponding drive outputs 1824a-d to allow the transfer of rotational torque from the drive outputs 1824a-d to the corresponding drive inputs 1636a-d. In some embodiments, each drive output 1824a-d may be spring loaded and otherwise biased to spring outwards away from the drive interface 1816. Each drive output 1824a-d may be capable of partially or fully retracting into the drive interface 1816.

In some embodiments, the instrument driver 1800 may include additional drive outputs, depicted in FIG. 18B as a fifth drive output 1824e and a sixth drive output 1824f. The fifth and sixth drive outputs 1824e,f may be configured and positioned to mate with additional drive inputs (not shown) of the drive housing 1614 to help undertake one or more additional functions of the surgical tool. In the illustrated embodiment, the drive housing 1614 does not include additional drive inputs, and the driven interface 1818 defines corresponding pockets 1826 configured to receive the fifth and sixth drive outputs 1824e,f.

Figure 19:
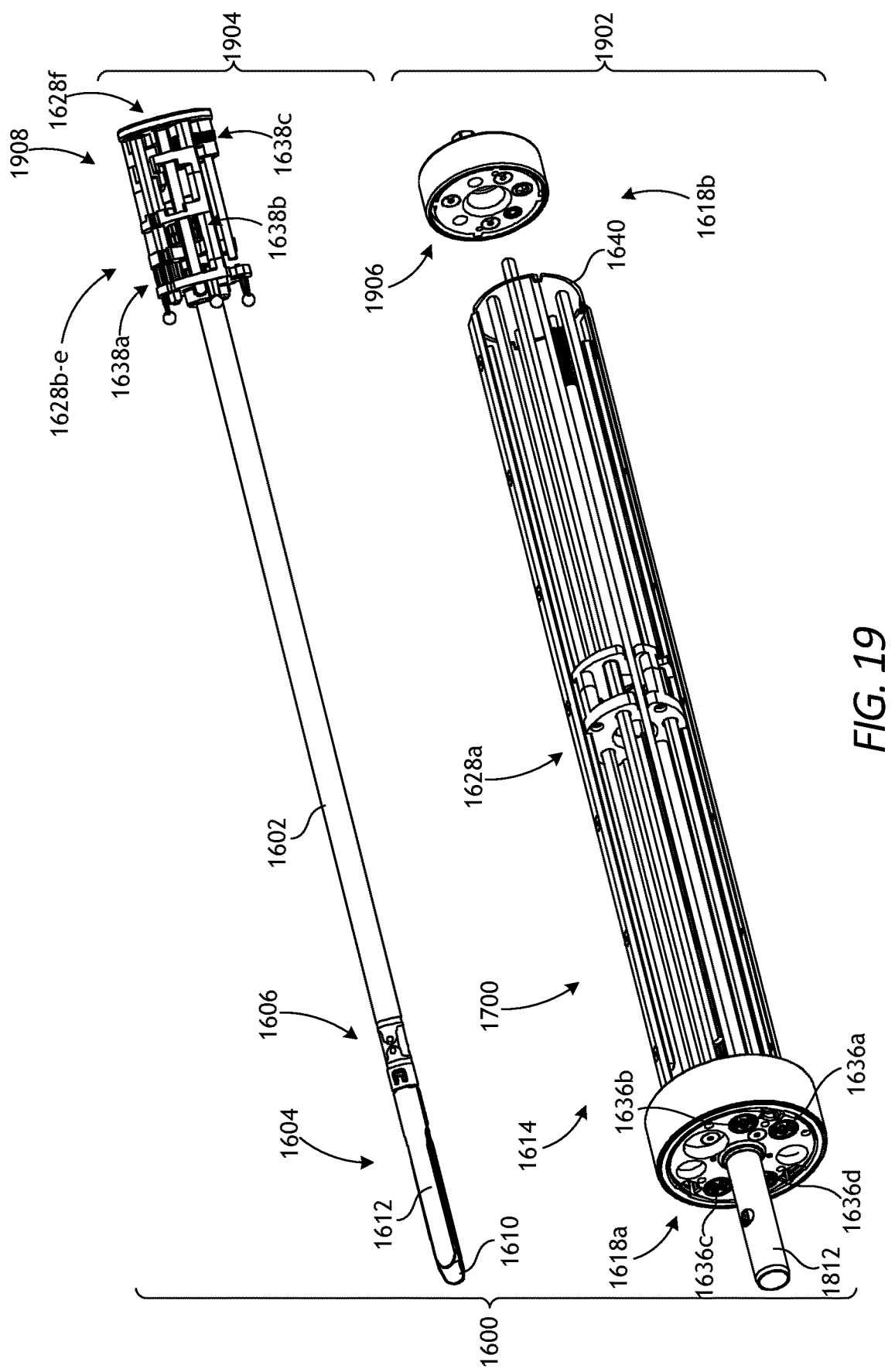
FIG. 19 illustrates the surgical tool of FIGS. 16-17 having a stage portion and an instrument portion when removed from a stage portion, according to one or more embodiments.

FIG. 19 illustrates the surgical tool 1600 configured with a stage portion 1902 and an instrument portion 1904 that may releasably attach to the stage portion 1902, according to one or more embodiments. In the illustrated embodiment, the instrument portion 1904 encompasses or comprises various component parts of a surgical stapler (e.g., an endocutter), but, as mentioned elsewhere herein, in other embodiments the instrument portion 1904 may encompass or comprise component parts relating to other types of surgical tools.

As illustrated, the stage portion 1902 may include an end cap or removable cap 1906 that may be removed from the shroud 1640 so that the instrument portion 1904 may be installed on or otherwise coupled to the stage portion 1902. In some embodiments, the end cap 1906 is removably attachable to the second end 1618b of the drive housing 1614 and removable to allow the instrument portion 1904 to be mated with a proximal side of the stage portion 1902. Accordingly, the end cap 1906 is sometimes referred to herein as the removable cap 1906. Here, the instrument portion 1904 includes a handle assembly 1908 (alternatively referred to as a "handle drive assembly") comprising the layers 1628b-e, the thrust bearing layer 1628f, and the associated activating mechanisms 1638a-c constrained thereby, and the shaft 1602 extends through a correspondingly sized central aperture in at least a portion of the handle assembly 1908. In this embodiment, the handle assembly 1908 may be dropped onto a proximal side of the first layer 1628a (i.e., the elevator layer) after removal of the removable cap 1906.

In the embodiments described above, the splines 1624a-c (FIG. 16) and the lead screw 1622 (FIG. 16) extend between the first and second ends 1618a,b. As described above, the splines 1624a-c and the lead screw 1622 extend from the first end 1618a, where they are operatively connected to the drive inputs 1636a-d of the surgical tool 1600 that are matable with and driven by a corresponding drive output 1824a-f (FIG. 18B) of the instrument driver 1800 (FIG. 18B), such that movement (rotation) of a given drive output 1824a-f correspondingly moves (rotates) the associated drive input 1636a-d, which thereby moves (rotates) the splines 1624a-c and the lead screw 1622 associated therewith. Also in these embodiments, the splines 1624a-c and the lead screw 1622 extend and are operatively coupled to the removable cap 1906.

Figure 20A:
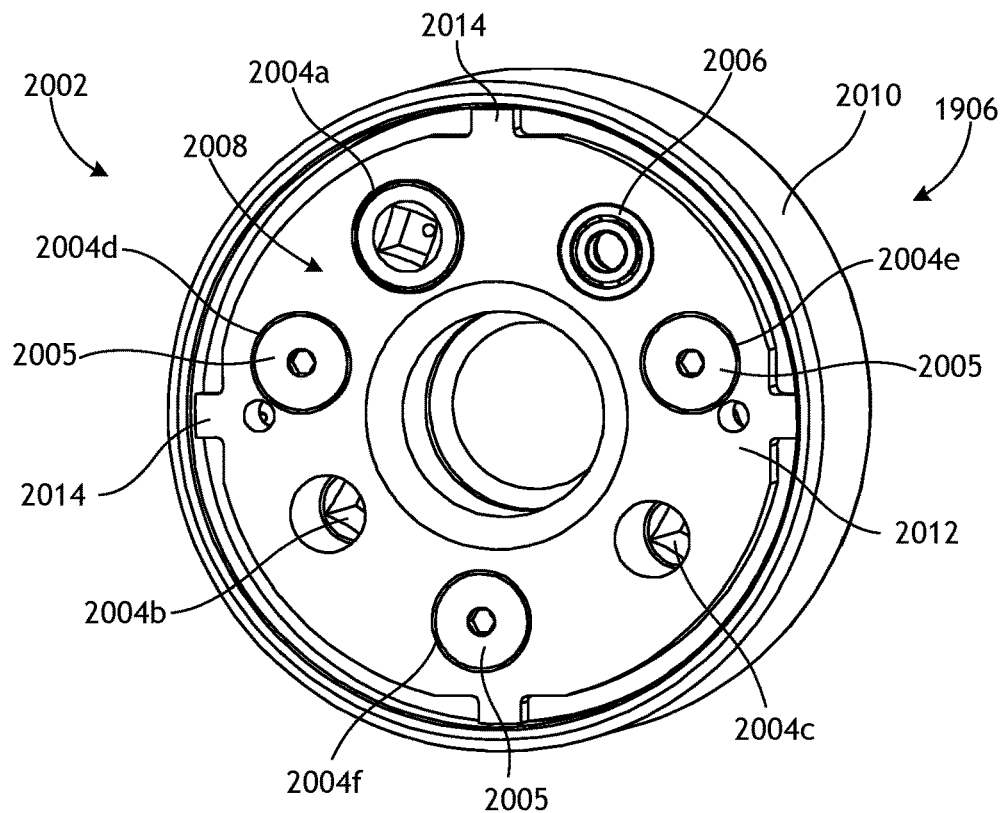
FIGS. 20A-20B illustrate respective bottom end and top end views of the removable cap of FIG. 19, according to one or more embodiments.
Figure 20B:
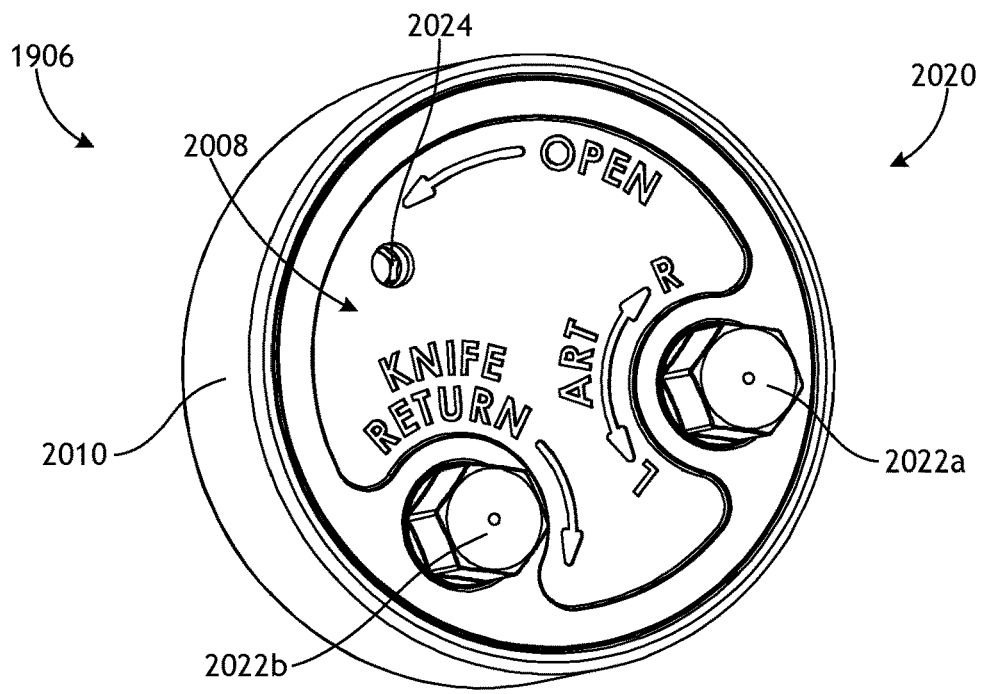

FIGS. 20A and 20B illustrate front and rear perspectives, respectively, of the removable cap 1906 of FIG. 19. In particular, FIG. 20A illustrates an interior engagement side 2002 of the removable cap 1906, according to one or more embodiments. The interior engagement side 2002 is configured to receive the ends of the splines 1624a-c (FIG. 16) and the lead screw 1622 (FIG. 16) when the removable cap 1906 is installed, and also configured to permit uncoupling from the splines 1624a-c and the lead screw 1622 for removal of the removable cap 1906. Thus, the interior engagement side 2002 may include couplings (receptacles) for each of the splines and/or lead screws. In the illustrated embodiment, the interior engagement side 2002 includes three spline couplings 2004a, 2004b, and 2004c arranged to correspond with the three splines 1624a-c. However, the interior engagement side 2002 may include more or less than the three spline couplings 2004a-c, for example, in embodiments having more or less than the three splines 1624a-c. Thus, additional locations 2004d-f may be configured to receive additional splines or drive elements. Here, hex head set screws 2005 are arranged at the additional locations 2004d-f as the illustrated embodiment utilizes the three spline couplings 2004a-c. In addition, the interior engagement side 2002 includes a stage coupling 2006 arranged to correspond with the lead screw 1622 (FIG. 16).

The spline couplings 2004a-c and the stage coupling 2006 are rotatably mounted within the removable cap 1906, such that they rotate with their corresponding spline 1624a-c (FIG. 16) and lead screw 1622 (FIG. 16) when engaged therewith by installing the removable cap 1906. Also, any or all of the spline couplings 2004*a-c* and/or stage coupling 2006 may be keyed to the end geometry of their corresponding splines 1624*a-c* and/or lead screw 1622. In some embodiments, the splines 1624*a-c* each include a square shaped end and each spline coupling 2004*a-c* includes a recess correspondingly shaped to receive the particular end geometry of the corresponding spline 1624*a-c*, so as to ensure that the spline couplings 2004*a-c* rotate with their associated splines 1624*a-c* while minimizing relative slippage there-between. It should be appreciated, however, that the splines 1624*a-c* and the associated spline couplings 2004*a-c* may be keyed with other geometries (e.g., triangular, polygonal, ovoid, etc.) and that each associated spline and coupling pair may be keyed with a geometry different from one or more of the other associated spline and coupling pair, without departing from the present disclosure.

In the illustrated embodiment, the stage coupling 2006 is illustrated as a low friction thrust bearing keyed to a corresponding end geometry of the lead screw 1622 (FIG. 16). As illustrated, the geometry of the stage coupling 2006 is circular, and in such embodiments, the end of the lead screw 1622 may be received within the stage coupling 2006 via an interference fit or the like. In other embodiments, however, the lead screw 1622 may be differently connected to the stage coupling 2006. In at least some embodiments, for example, the lead screw 1622 (FIG. 16) may be threaded into the screw coupling 2006. As described herein, alternate mechanisms or actuators are utilized to affect linear translation of the carriage 1626 (FIG. 16) instead of the lead screw 1622, such as, for example, a belt or cable drive actuator arranged to cause linear translation of the carriage 1626, and, in such embodiments, the stage coupling 2006 may be appropriately configured to integrate with said alternate mechanisms or actuators such that activation of the appropriately configured stage coupling correspondingly activates said alternate mechanisms or actuators as described herein.

In the illustrated embodiment, the removable cap 1906 further includes a frame assembly 2008 and a ring 2010 arranged about the frame assembly 2008. The frame assembly 2008 is configured to retain the spline couplings 2004*a-c* and the stage coupling 2006. In some examples, additional spline couplings (e.g., similar to the spline couplings 2004*a-c*) may be arranged at the additional locations 2004*d-f* with an organization that comports with a standard alignment of splines such that the removable cap 1906 is utilizable with the maximum number of splines even where the handle assembly 1908 (FIG. 19) riding thereon may not be configured to receive input from one or more of the maximum number of splines.

The interior engagement side 2002 of the removable cap 1906 may be configured to mate with the shroud assembly 1700 (FIG. 17). In the illustrated example, the frame assembly 2008 includes a boss 2012 protruding outward to define a plurality of alignment tabs 2014. When installing the removable cap 1906, the alignment tabs 2014 may be used to ensure proper alignment by locating the alignment tabs 2014 within the corresponding alignment notches 1708 (FIG. 17) defined in the shroud 1640 (FIG. 17).

According to embodiments of the present disclosure, the removable cap 1906 may be configured to allow manual actuation of the splines 1624*a-c* (FIG. 16) and/or the lead screw 1622 (FIG. 16), independent of the instrument driver 1800. FIG. 20B illustrates an exterior side 2020 of the removable cap 1906 that is configured for manually actuating the splines 1624*a-c* (FIG. 16) and the lead screw 1622 (FIG. 16). In the illustrated embodiment, a pair of manual control nuts 2022*a* and 2022*b* are provided for allowing manual rotation of the spline couplings 2004*b-c*, respectively, and a stage socket 2024 is provided for allowing manual rotation of the stage coupling 2006. The manual control nuts 2022*a,b* are rotationally fixed to their corresponding spline coupling 2004*b,c* such that manual rotation of the manual control nuts 2022*a,b* correspondingly rotates the associated spline coupling 2004*b-c* as well as the interconnected (mated) spline 1624*b,c* (FIG. 16) when the removable cap 1906 is installed. Similarly, the stage socket 2024 is rotationally fixed to the stage coupling 2006 such that the stage socket 2024 and the stage coupling 2006 rotate in unison. In this manner, a user may manually rotate the lead screw 1622 (FIG. 16) when the removable cap 1906 is installed by turning the stage socket 2024, for example, with an Allen wrench. In other embodiments, alternate actuation is utilized to axially translate the carriage 1626 (FIG. 16) of the surgical tool 1600 in lieu of the lead screw 1622, such as, for example, a belt or cable drive actuator, and in such embodiments, the user may manually activate such alternate actuation when the removable cap 1906 is installed by turning the stage socket 2024 as described herein.

Such manual features may prove advantageous in allowing a user to manually manipulate the functions of the surgical tool 1600 (FIG. 16), such as articulating or firing the end effector 1604 (FIG. 16) and/or advancing or retracting the elongate shaft 1602 (FIG. 16) by axially translating the carriage 1626 (FIG. 16). This may help in manual bailout situations when power to the surgical tool 1600 may be lost or the surgical tool 1600 is otherwise rendered inoperable.

In the illustrated example, the manual control nuts 2022*a,b* and their corresponding spline coupling 2004*b-c* are associated with the spline 1624*b,c*, such that rotation of the manual control nuts 2022*a,b* causes articulation of the wrist 1606 (FIG. 16) and firing of the end effector 1604 (FIG. 16). However, either or both of the manual control nuts 2022*a,b* and their corresponding spline coupling 2004*b-c* may be associated with a different spline to manually actuate or drive the functionality of the surgical tool 1600 associated with that different spline. For example, one of the manual control nuts 2022*a,b* and its corresponding spline coupling 2004*b-c* may be associated with the first spline 1624*a* to open or close the jaws 1610,1612. Thus, the manual control nuts 2022*a,b* and their corresponding spline coupling 2004*b-c* may be configured to manually actuate or drive any functionality of the surgical tool 1600, regardless of whether the end effector 1604 is configured as a surgical stapler or any of the other types of surgical instruments mentioned herein.

The removable cap 1906 may also be configured to manually actuate or drive an additional function of the surgical tool 1600 that is not associated with the manual control nuts 2022*a,b* and their corresponding spline coupling 2004*b-c*. For example, the removable cap 1906 may be configured to permit manual actuation of the first spline coupling 2004*a* (FIG. 20A) and the interconnected first spline 1624*a* (FIG. 16) received therein to thereby manually actuate or drive an additional function of the surgical tool 1600. In the illustrated embodiment, the ring 2010 is operatively coupled to the first spline coupling 2004 such that manually rotating the ring 2010 relative to the frame assembly 2008 will correspondingly rotate the first spline coupling 2004. Here, the ring 2010 extends about a periphery of the frame assembly 2008 and is arranged thereon so that it may rotate around the periphery relative to the frame assembly 2008.

Figure 21:
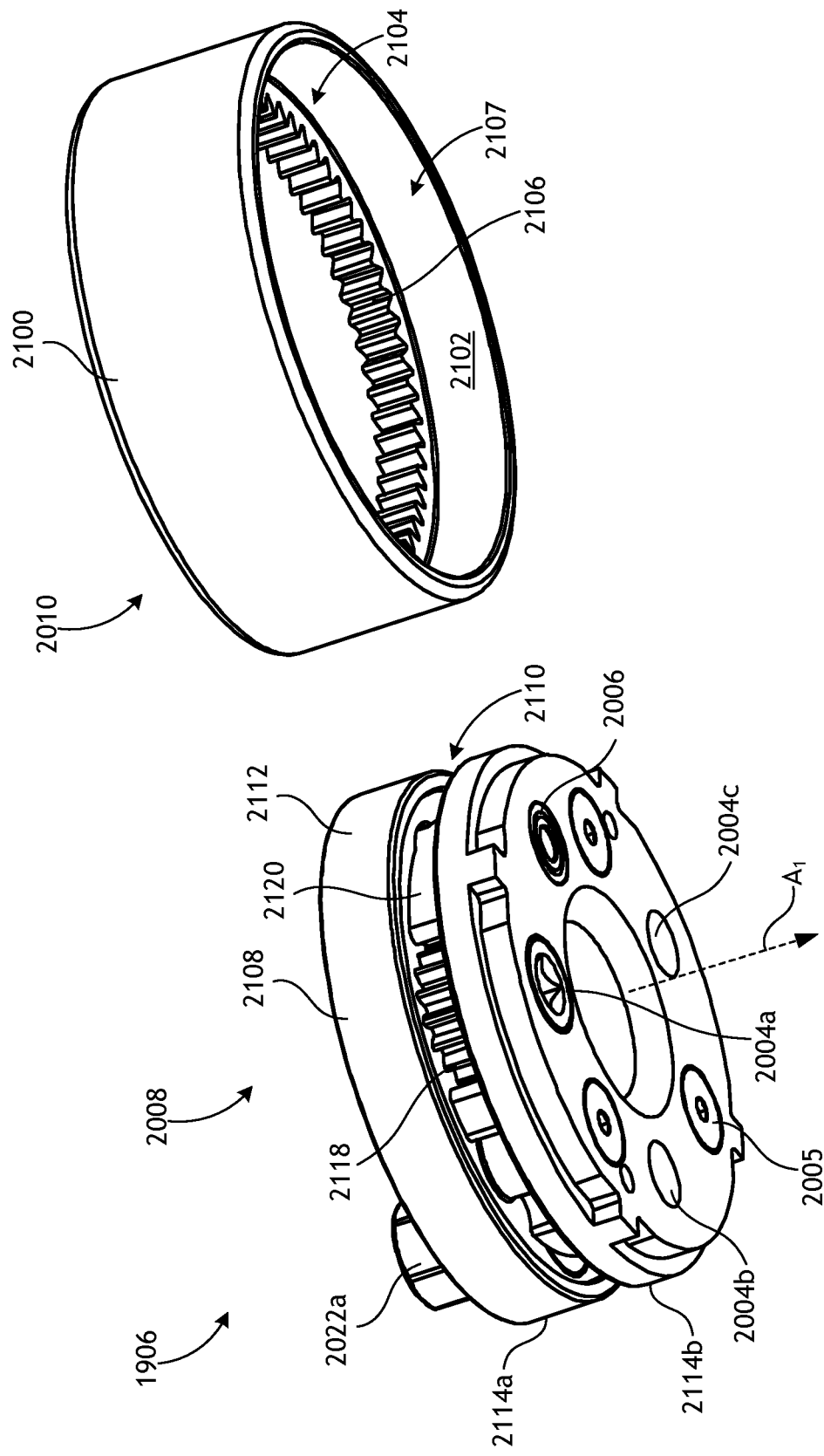
FIG. 21 illustrates a partially-exploded view of the removable cap of FIGS. 20A-20B, according to one or more embodiments.

FIG. 21 is a partially exploded view of the removable cap 1906 of FIGS. 20A-20B, according to one or more embodiments. In particular, FIG. 21 illustrates the removable cap 1906 with the ring 2010 having been removed from the frame assembly 2008. As illustrated, the ring 2010 includes an annular body 2100 having an inner surface 2102, and a ring gear 2104 is provided (defined) on the inner surface 2102. The ring gear 2104 comprises a plurality of teeth 2106 and extends circumferentially about all or a portion of the inner surface 2102. As shown, the ring gear 2104 protrudes radially inward from the inner surface 2102 and into a bore 2107 of the body 2100 so as to define a ridge having a smaller diameter as compared to the larger diameter of the inner surface 2102.

The frame assembly 2008 includes a body 2108 about which the ring 2010 extends. The body 2108 is configured to permit rotation of the ring 2010 about an axis $A_1$ of the frame assembly 2008 and relative to the body 2108 when the ring 2010 is arranged thereon. In addition, the body 2108 may be configured to inhibit axial translation of the ring 2010 relative to the body 2108 when the ring 2010 is arranged thereon. Thus, the body 2108 is configured to permit relative rotation of the ring 2010 while simultaneously inhibiting relative axial translation of the ring 2010.

In the illustrated embodiment, the body 2108 includes a channel 2110 extending circumferentially around a periphery 2112 of the body 2108, and the channel 2110 is arranged to align with the ring gear 2104 of the ring 2010 and may thus be sized accordingly. Also in the illustrated embodiment, the body 2108 comprises a top (or first) component 2114a and a bottom (or second) component 2114b that is separable from the top component 2114a. To assemble the body 2108, the top component 2114a may be partially inserted into the bore 2107 of the ring 2010 from its top until engaging the ring gear 2104, and the bottom component 2114b may be partially inserted into the ring 2010 from its bottom until engaging the ring gear 2104 on the underside. One or more set screws 2005 may then be used to couple the top and bottom components 2114a-b while simultaneously capturing the ring gear 2104 between the top and bottom components 2114a-b. In the illustrated, example, three set screws 2005 are illustrated for assembling the body 2108 to the ring 2010, but more or less may be used in other embodiments.

The spline coupling 2004a may include a pinion gear 2116 having a plurality of teeth 2118. The pinion gear 2116 is secured to the spline coupling 2004a such that they rotate in unison (together). The pinion gear 2116 may be rotatably mounted to the body 2108 such that the pinion gear 2116 extends into the channel 2110 and is engageable by the ring gear 2104 through the channel 2110. Thus, the channel 2110 defines an annular surface 2120, and the annular surface 2120 and the ring gear 2104 may be correspondingly sized and positioned such that the ring gear 2104 travels within the channel 2110 without any interference between the teeth 2106 of the ring gear 2104 and the channel 2110 as the ring 2010 rotates about the body 2108 of the frame assembly 2008.

The pinion gear 2116 may be arranged such that the teeth 2118 extend beyond the annular surface 2120 and into the channel 2110. In this manner, the teeth 2106 of the ring gear 2104 may engage and mesh with the teeth 2118 of the pinion gear 2116 when the ring 2010 is assembled on the frame assembly 2008, such that rotation may be imparted on the pinion gear 2116 by rotating the ring gear 2104 through interaction of their respective teeth 2106, 2118. Accordingly, rotation of the ring 2010 about the axis $A_1$ of the frame assembly 2008 causes the ring gear 2104 to similarly rotate about the axis $A_1$, which in turn causes rotation of the pinion gear 2116 intermeshed with the ring gear 2104 and rotation of the spline coupling 2004a extending from the pinion gear 2116, such that the first spline 1624a (FIG. 16) when received within the spline coupling 2004a may be manually actuated (independent of the instrument driver 1800 of FIG. 18A) by rotating the removable cap 1906.

Figure 22:
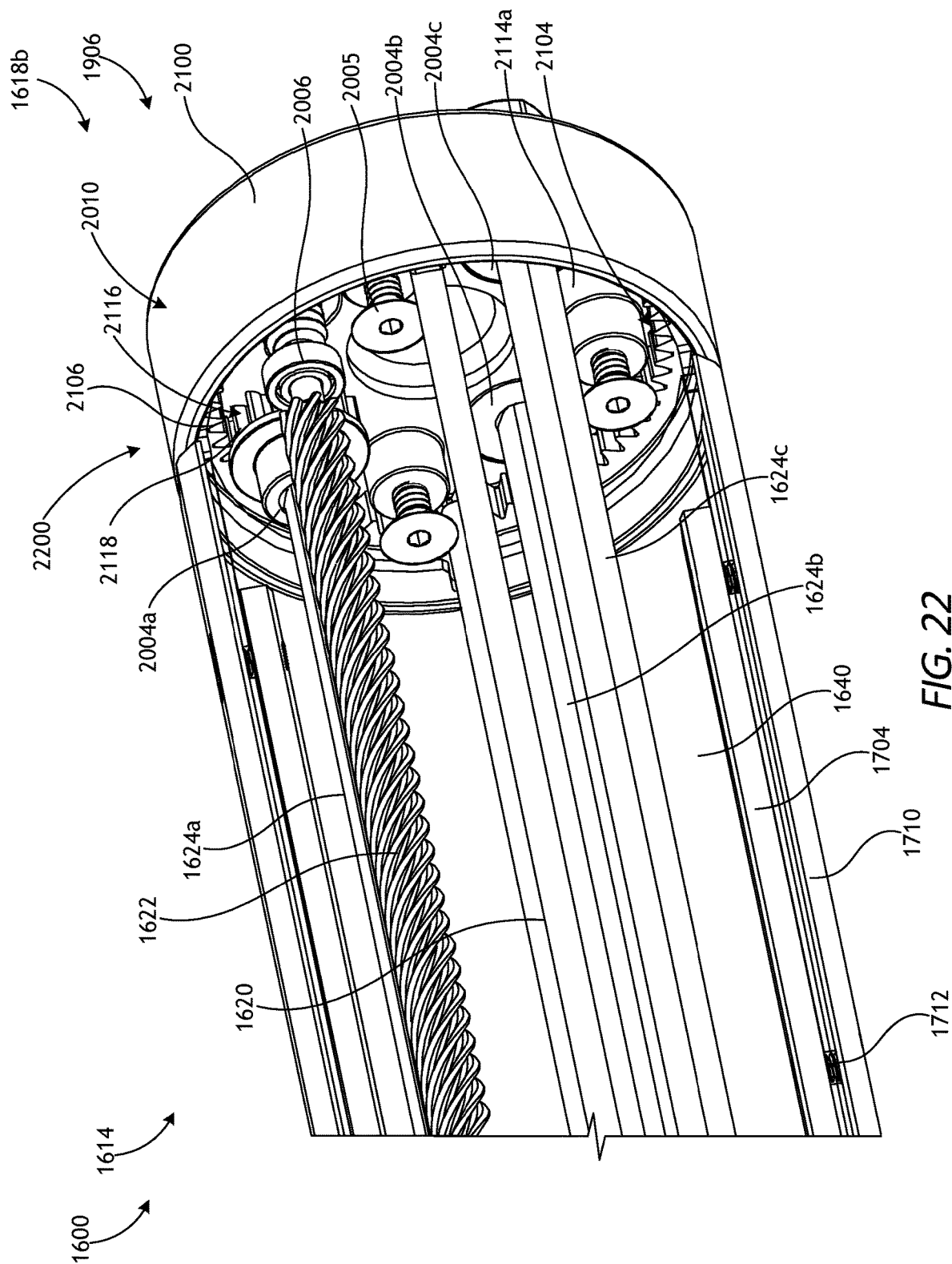
FIG. 22 illustrates a partially disassembled view of the removable cap when installed on the surgical tool and in operational engagement with the lead screw and the splines, according to one or more embodiments.

The removable cap 1906 thus embodies mechanisms for manually actuating the lead screw 1622 and the splines 1624a-c and, thereby, for manually activating the various functions of the surgical tool 1600 associated with the lead screw 1622 and the splines 1624a-c. Accordingly, when the removable cap 1906 is installed on the (proximal) second end 1618b of the surgical tool 1600, such that the stage coupling 2006 and the spline couplings 2004a-c are operationally engaged with the lead screw 1622 and the splines 1624a-c as mentioned above, the removable cap 1906 embodies a proximal manual actuation mechanism. FIG. 22 illustrates the removable cap 1906 configured as a proximal manual actuation mechanism 2200 for manually activating one or more functions of the surgical tool 1600, according to one or more embodiments. As illustrated, the proximal manual actuation mechanism 2200 is provided to manually actuate the first spline coupling 2004a, together with the first spline 1624a arranged therein, via rotation of the ring 2010 such that a user may utilize the proximal manual actuation mechanism 2200 to manually activate the first activating mechanism 1638a (FIG. 19) and thereby manually open or close the jaws 1610, 1612 (FIG. 19).

Accordingly, the proximal manual actuation mechanism 2200 may embody a manual jaw open and closure mechanism. However, in other embodiments, the proximal manual actuation mechanism 2200 may instead be provided to manually activate any other functionality of the surgical tool 1600. For example, the proximal manual actuation mechanism 2200 may instead be provided to manually actuate the stage coupling 2006 and the lead screw 1622 arranged therein to manually activate the corresponding functionality of the surgical tool 1600 (i.e., to provide manual translation of the carriage nut 1634 (FIG. 16) and first layer 1628a or the carriage 1626 (FIG. 16) when so assembled), such that the proximal manual actuation mechanism 2200 embodies a manual stage translation mechanism. In other examples, the proximal manual actuation mechanism 2200 may instead be provided to manually actuate the second spline coupling 2004b together with the second spline 1624b arranged therein to manually drive the second activating mechanism 1638b (FIG. 16) and thereby manually articulate the wrist 1606 (FIG. 16), such that the proximal manual actuation mechanism 2200 embodies a manual wrist articulation mechanism. In even other examples, the proximal manual actuation mechanism 2200 may instead be provided to manually actuate the third spline coupling 2004c together with the third spline 1624c arranged therein to manually drive the third activating mechanism 1638c (FIG. 16) and thereby manually fire the end effector 1604 (FIG. 16), such that the proximal manual actuation mechanism 2200 embodies a manual firing mechanism. Alternatively, the proximal manual actuation mechanism 2200 may be provided to manually activate two or more functions of the surgical tool 1600. As described below, the proximal manual actuation mechanism 2200 may embody both the proximal manual jaw open and closure mechanism and the proximal manual stage translation mechanism, or various other combinations of two or more functionalities.

In FIG. 22 the removable cap 1906 is depicted without the bottom component 2114b, so as to more clearly depict example operation of the proximal manual actuation mechanism 2200. In particular, FIG. 22 illustrates an exemplary interaction between the ring gear 2104 provided within the ring 2010 and the pinion gear 2116 provided on the spline coupling 2004a in which the first spline 1624a is provided. As described above, the spline couplings 2004a-c are each rotatably mounted within the frame assembly 2008 (FIG. 21), and the frame assembly 2008 is attachable to struts 1620 (when the removable cap 1906 is installed) such that the frame assembly 2008 is constrained by the drive housing 1614 and rotationally fixed to the ring 2010. In this manner, the ring 2010 may be rotated about the frame 2008 while the frame 2008 remains stationary relative to the remainder of the drive housing 1614.

To utilize the proximal manual actuation mechanism 2200, the user may hold the surgical tool 1600 at the first end 1618a (FIG. 16) or at the shroud 1640 and then manually apply a rotational force to (twist) the ring 2010 of the removable cap 1906, which thereby causes the ring 2010 to rotate about the frame assembly 2008 (FIG. 21). As mentioned, the ring gear 2104 rotates with the ring 2010, the pinion gear 2116 rotates with the first spline coupling 2004a, and the ring gear 2014 and the pinion gear 2166 are operatively coupled together via intermeshing of the teeth 2106 of ring gear 2104 with the teeth 2118 of the pinion gear 2116. Rotation of the ring 2010 and the ring gear 2104 provided thereon drives (rotates) the pinion gear 2116 operatively coupled thereto, and rotation of the pinion gear 2116 correspondingly drives (rotates) the first spline coupling 2004a provided on the pinion gear 2116 to thereby drive (rotate) the first spline 1624a received in the first spline coupling 2004a. Thus, the proximal manual actuation mechanism 2200 may be provided such that manually rotating of the ring 2010 in a first rotational direction actuates of the first spline 1624 to thereby open the jaws 1610, 1612 (FIG. 16), whereas manually rotating of the ring 2010 in a second rotational direction (opposite the first rotational direction) actuates of the first spline 1624 to thereby close the jaws 1610, 1612 (FIG. 16).

As mentioned, the proximal manual actuation mechanism 2200 may also be provided to manually actuate one or more additional functions of the surgical tool 1600. Thus, the stage coupling 2006 and/or either or both of the spline couplings 2004b-c may be operatively coupled to the ring gear 2104 such that rotation of the ring 2010 activates their associated functionality(ies) while simultaneously opening or closing the jaws 1610, 1612 (FIG. 16). For example, one or more of the stage coupling 2006 and the spline couplings 2004b-c may each be provided with a pinion gear, similar as described with reference to the first spline coupling 2004a, to drive the stage coupling 2006 and/or spline couplings 2004b-c corresponding therewith and thereby cause activation of the associated functionality of the surgical tool 1600. However, other gearing mechanisms may be utilized to operatively couple the ring gear 2104 with any one or more of the stage coupling 2006 and/or the spline couplings 2004b-c.

In one example embodiment, rotation of the proximal manual actuation mechanism 2200 manually opens or closes the jaws 1610, 1612 (FIG. 16), as described above, while simultaneously rotating the stage coupling 2006, together with the lead screw 1622 received therein, to translate the carriage nut 1634 (FIG. 16) and the first layer 1628a (FIG. 16) connected thereto, which may be beneficial for removing the instrument portion 1904 (FIG. 19) of the surgical tool 1600 from the stage portion 1902 (FIG. 19). In one such embodiment, rotation of ring 2010 in the first rotational direction causes simultaneous closure of the jaws 1610, 1612 and proximal translation of the first layer 1628a. In this manner, when the instrument portion 1904 is assembled on the stage portion 1902, the user may rotate the ring 2010 in the first rotational direction to proximally translate the carriage 1626 (FIG. 16) while simultaneously closing the jaws 1610, 1612, such that the jaws 1610, 1612 may be retracted through the alignment nozzle 1812 (FIG. 19) provided at the (distal) first end 1618a of the drive housing 1614 (FIG. 19) without interference as the jaws 1610, 1612 translate proximally with the carriage 1626. This dual functionality of the proximal manual actuation mechanism 2200 may prove helpful when removing the instrument portion 1904 from the stage portion 1902.

The proximal manual actuation mechanism 2200 allows the user to open or close the jaws 1610, 1612 (FIG. 16) (or manually activate one or more other or additional functions of the surgical tool 1600) with a single hand. Also, the proximal manual actuation mechanism 2200 may be utilized to install (or exchange) a staple cartridge in the end effector 1604 (FIG. 16). For example, a user may manipulate the proximal manual actuation mechanism 2200 the open or close the jaws 1610, 1612 when detached from the instrument driver 1800 (FIG. 18) to remove a staple cartridge from the jaws 1610, 1612 and/or install a new staple cartridge therein. However, the proximal manual actuation mechanism 2200 may also be manipulated when the surgical tool 1600 is attached to the instrument driver 1800.

Figure 23:
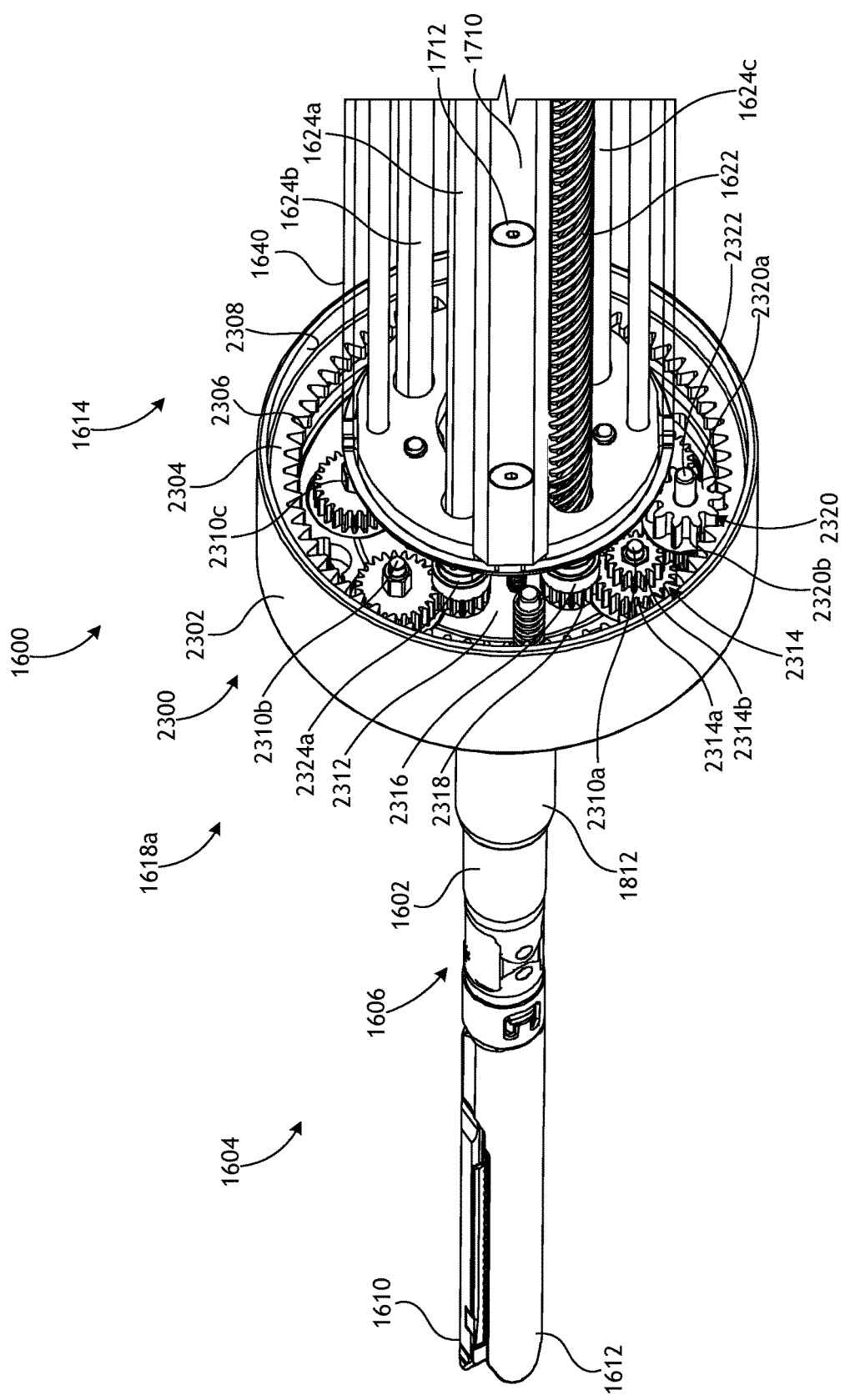
FIG. 23 illustrates a partially disassembled view of a distal manual actuation mechanism for manually activating one or more functions of a surgical tool, according to one or more embodiments.

In some embodiments, a manual actuation mechanism may be provided at the first (distal) end 1618a of the drive housing 1614 (FIG. 18A). FIG. 23 illustrates a distal manual actuation mechanism 2300 for manually activating one or more functions of the surgical tool 1600, according to one or more embodiments. In the illustrated embodiment, the distal manual actuation mechanism 2300 includes an enclosure or distal drive housing 2302 coupled to the driven interface 1818 (FIG. 18B) provided at the first end 1618a of the drive housing 1614. Here, the distal drive housing 2320 is ring shaped and rotatably coupled to the driven interface 1818 such that the ring shaped distal drive housing 2320 may rotate about and relative to the driven interface 1818 and the remainder of the drive housing 1614, similar to as described with regards to the ring 2010 of FIGS. 21-22. Also, a ring gear 2304 having a plurality of teeth 2306 is provided along an inner periphery (or circumference) 2308 of the distal drive housing 2302, such that the ring gear 2304 and the teeth 2306 thereof may rotate in unison with the distal drive housing 2302.

As previously mentioned, the drive inputs 1636a-d (FIG. 18B) are provided on the driven face 1818 (FIG. 18B) at the first end 1618a of the drive housing 1614. In the illustrated embodiment, the first drive input 1636a (FIG. 18B) is operatively coupled to the lead screw 1622 such that rotation of the first drive input 1636a correspondingly rotates the lead screw 1622 to cause translation of the first layer 1628a (FIG. 16) and the carriage 1626 (FIG. 16) when assembled. The second drive input 1636b (FIG. 18B) is operatively coupled to the first spline 1624a such that rotation of the second drive input 1636b correspondingly rotates the first spline 1624a operatively coupled to the first activating mechanism 1638a (FIG. 16) to thereby open and close the jaws 1610, 1612 (FIG. 16). In addition, the third drive input 1636c (FIG. 18B) may be operatively coupled to the second spline 1624b such that rotation of the third drive input 1636c correspondingly rotates the second spline 1624b operatively coupled to the second activating mechanism 1638*b* (FIG. 16) operable to thereby articulate the end effector 1604 (FIG. 16) at the wrist 1606 (FIG. 16). Moreover, the fourth drive input 1636*d* (FIG. 18B) may be operatively coupled to the third spline 1624*c* such that rotation of the fourth drive input 1636*d* correspondingly rotates the third spline 1624*c* operatively coupled to the third activating mechanism 1638*c* (FIG. 18B) operable to thereby fire the cutting element (knife) at the end effector 1604.

A drive input shaft is provided on each of the drive inputs 1636*a-d* (FIG. 18B), such rotation of each of the drive inputs 1636*a-d* in turn rotates its respective drive input shaft. In FIG. 23, a first drive input shaft 2310*a* is shown extending from the first drive input 1636*a* (FIG. 18B) such that the first drive input shaft 2310*a* rotates in unison with the first drive input 1636*a*. A second drive input shaft 2310*b* also extends from the second drive input 1636*b* (FIG. 18B) such that the second drive input shaft 2310*b* rotates in unison with the second drive input 1636*b*. Moreover, a third drive input shaft 2310*c* is shown extending from its respective third drive input 1636*c* (FIG. 18B) such that the third drive input shaft 2310*c* rotates in unison with the third drive input 1636*c*. Similarly, a fourth drive input shaft 2310*d* (occluded from view) extends from its respective fourth drive input 1636*d* (FIG. 18B), such that the fourth drive input shaft 2310*d* rotates in unison with the fourth drive input 1636*d*. The drive input shafts 2310*a-d* are rotatably mounted on a base plate 2312 of the driven face 1818 (FIG. 18B).

A compound drive gear 2314 is provided on the first drive input shaft 2310*a*. The compound drive gear 2314 comprises a first drive gear 2314*a* and a second drive gear 2314*b*, and the first and second drive gears 2314*a,b* are each disposed on the first drive input shaft 2310*a* such that they rotate together in unison with the first drive input shaft 2310*a*. Also, a stage coupling 2316 is provided on a distal end of the lead screw 1622 and the stage coupling 2316 includes a driven gear 2318 extending therefrom, such that the driven gear 2318 rotates in unison with the lead screw 1622. The compound drive gear 2314 and the stage coupling 2316 are arranged on the base plate 2312 such that the first drive gear 2314*a* of the compound drive gear 2314 intermeshes with the driven gear 2318 of the stage coupling 2316. Accordingly, the compound drive gear 2314 and the stage coupling 2316 operatively couple the first drive input 1636*a* (FIG. 18B) and the lead screw 1622, such that rotation of the first drive input 1636*a* correspondingly rotates the first drive gear 2314*a*, which in turn drives the driven gear 2318 intermeshed therewith to cause rotation of the stage coupling 2316 and the lead screw 1622 to cause translation of the first layer 1628*a* (FIG. 16) and the carriage 1626 (FIG. 16) when assembled.

A compound idler gear 2320 operatively couples the ring gear 2304 with the lead screw 1622, such that rotation of the distal drive housing 2302 causes rotation of the lead screw 1622. In the illustrated embodiment, the compound idler gear 2320 comprises a first idler gear 2320*a* and a second idler gear 2320*b*. The first and second idler gears 2320*a,b* are secured to an idler shaft 2322 and connected together to rotate in unison on the idler shaft 2322. The idler shaft 2322 and the compound idler gear 2320 are arranged such that teeth of the first idler gear 2320*a* intermesh with the teeth 2306 of the ring gear 2304 and such that teeth of the second idler gear 2320*b* intermesh with the teeth of the second drive gear 2314*b* of the compound drive gear 2314. As previously mentioned, the second drive gear 2314*b* rotates with the first drive gear 2314*a* and the teeth of the first drive gear 2314*a* intermesh with the teeth of the driven gear 2318, which rotates with the stage coupling 2316. Accordingly, rotation of the distal drive housing 2302 and the ring gear 2304 fixed therein rotates the compound idler gear 2320 via interaction between the ring gear 2304 and the first idler gear 2320*a*, rotation of the compound idler gear 2320 in turn rotates the compound drive gear 2314 via interaction between the second idler gear 2320*b* and the second drive gear 2314*b*, and rotation of the compound drive gear 2314 in turn rotates the stage coupling 2316 via interaction between the first drive gear 2314*a* and the driven gear 2318, thereby rotating the lead screw 1622 and translating the first layer 1628*a* within the drive housing 1614. Thus, the distal manual actuation mechanism 2300 may embody a distal manual stage translation mechanism utilized to manually translate at least the first layer 1628*a* (or the carriage 1626 when assembled) within the drive housing 1614.

In other embodiments, however, the distal manual actuation mechanism 2300 may embody a distal manual jaw open and closure mechanism for manually opening or closing the jaws 1610, 1612. For example, the distal manual actuation mechanism 2300 may alternatively be provided to manually actuate a first spline coupling 2324*a*, together with the first spline 1624*a* that is rotationally fixed to the first spline coupling 2324*a*, via rotation of the distal drive housing 2302 such that a user may utilize the distal manual actuation mechanism 2300 to manually activate the first activating mechanism 1638*a* (FIG. 19) and thereby manually open or close the jaws 1610, 1612 (FIG. 19). In this example, a pinion gear (not illustrated) attached to the first spline coupling 2324*a* may be provided to couple the ring gear 2304 and the first spline coupling 2324*a*, as described with reference to the pinion gear 2116 in FIGS. 21-22. Alternatively, one or more idler gears (not illustrated) may be provided to operatively couple the ring gear 2304 and the first spline coupling 2324*a* as described with reference to FIG. 23. Thus, various configurations of operatively connected gears having different gear ratios, speeds, loads, or gear positions may be utilized without departing from the present disclosure. In some embodiments, the distal manual actuation mechanism 2300 may embody both the distal manual stage translation mechanism and the distal manual jaw open and closure mechanism.

It will be appreciated that the distal manual actuation mechanism 2300 may instead be operatively coupled to the second and/or third splines 1624*b,c* in addition to or instead of either or both of the lead screw 1622 and the first spline 1624*a*. For example, the distal manual actuation mechanism 2300 may instead be provided to manually actuate a second spline coupling (occluded from view) together with the second spline 1624*b* arranged therein to manually drive the second activating mechanism 1638*b* (FIG. 16) and thereby manually articulate the wrist 1606 (FIG. 16), such that the distal manual actuation mechanism 2300 embodies a distal manual wrist articulation mechanism. In other examples, the distal manual actuation mechanism 2300 may instead be provided to manually actuate a third spline coupling (occluded from view) together with the third spline 1624*c* arranged therein to manually drive the third activating mechanism 1638*c* (FIG. 16) and thereby manually affect firing of the end effector 1604 (FIG. 16), such that the distal manual actuation mechanism 2300 embodies a distal manual firing mechanism. Alternatively, the distal manual actuation mechanism 2300 may be provided to manually activate two or more functions of the surgical tool 1600. Accordingly, the distal manual actuation mechanism 2300 may embody both the distal manual jaw open and closure mechanism and the distal manual stage translation mechanism, or various other combinations of two or more functionalities of the surgical tool 1600 in a manner similar to the proximal manual actuation mechanism 2200 (FIGS. 21-22).

Figure 24:
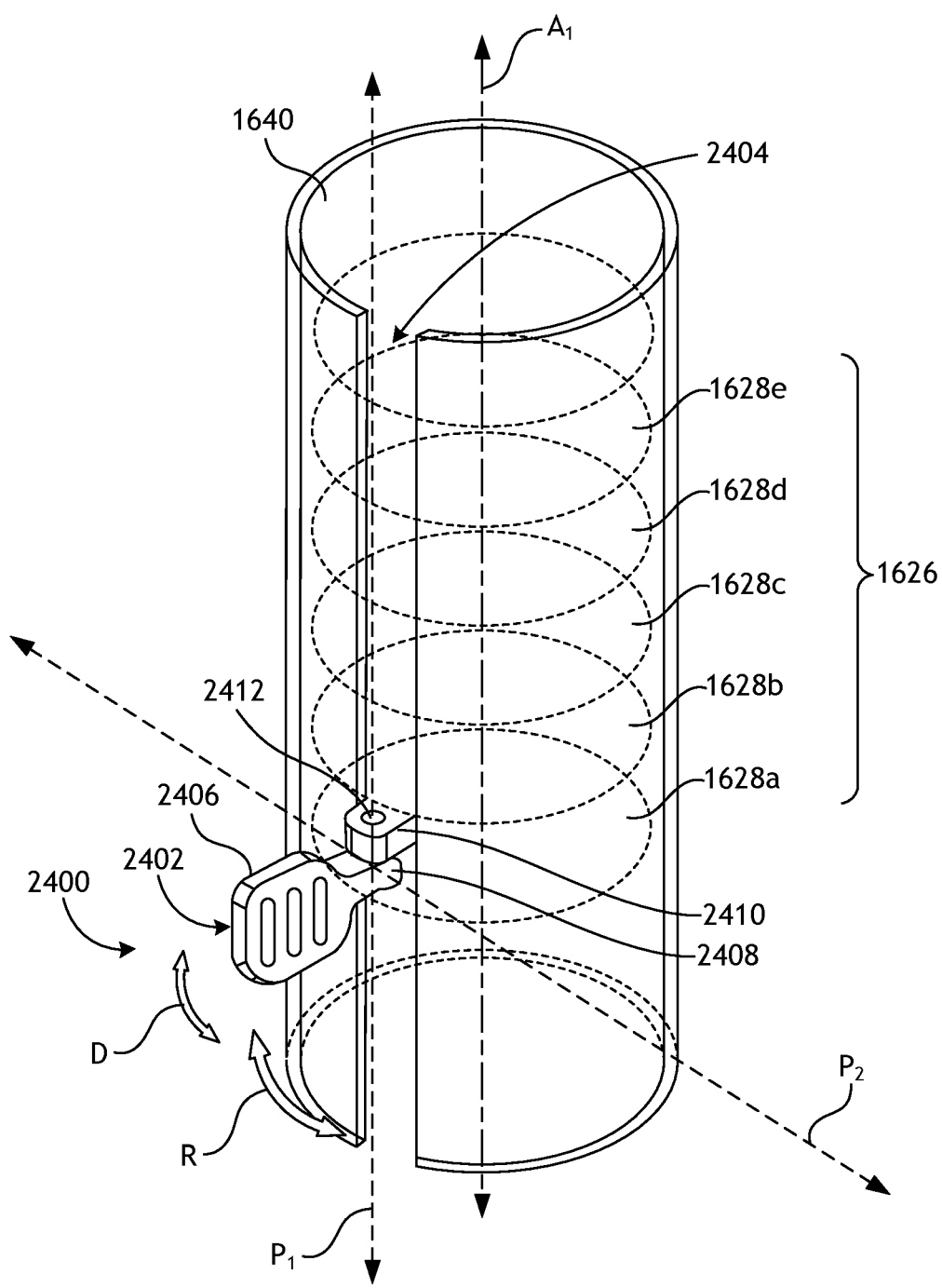
FIG. 24 illustrates a manual lever jaw opening and closure mechanism, according to one or more embodiments.

FIG. 24 illustrates an alternate manual jaw opening and closure mechanism 2400, according to one or more embodiments. In the illustrated embodiment, the manual jaw opening and closure mechanism 2400 (hereinafter, the "mechanism 2400") includes a lever 2402 operatively coupled to the carriage 1626 and movable to switch or change loading (i.e., input rotation) of the first activating mechanism 1638a (FIG. 16). More specifically, the lever 2402 is movable to decouple (disengage) the first spline 1624a (FIG. 16) from the first activating mechanism 1638a, such that the first spline 1624a does not impart rotational force (load) on the first activating mechanism 1638a (via the instrument driver 1800 of FIG. 18B). The lever 2402 may further be movable to load the first activating mechanism 1638a with rotation force to affect movement of the jaws 1610, 1612 (FIG. 16). As the lever 2402 decouples (disengages) the first spline 1624a from the first activating mechanism 1638a, the lever 2402 may simultaneously couple (engage) the activating mechanism 1638a to a new source of rotational force (load) for manually actuating first activating mechanism 1638a and the jaws 1610, 1612.

In the illustrated embodiment, the carriage 1626 is provided in the shroud 1640 and the lever 2402 protrudes outward from the carriage 1626 through an opening 2404 defined in the shroud 1640. Here, the opening 2404 is defined in the form of a longitudinal slot that vertically extends the entirety (or a substantial length) of the shroud 1640, between the first and second ends 1618a,b (FIG. 16). In other embodiments, however, the opening 2404 may be differently shaped and/or sized to allow the lever 2402 to protrude outward therefrom and to allow pivoting movement of the lever 2402, as described below. While the lever 2402 is shown extending from the first layer 1628a of the carriage 1626, in other embodiments, the lever 2402 may be operatively coupled at the second layer 1628b, at the third layer 1628c, or at the fourth layer 1628d, for example, in embodiments where the first activating mechanism 1638a is housed in the second layer 1628b, the third layer 1628c, or at the fourth layer 1628d. Also, while the lever 2402 is described as being operable with regard to the first activating mechanism 1638a, in other embodiments, it may be integrated into the carriage 1626 to affect loading of the carriage nut 1626, the second activating mechanism 1638b (FIG. 16), and/or the third activating mechanism 1638c (FIG. 16), without departing from the scope of the disclosure.

As illustrated, the lever 2402 may include a user engagement (tab) portion 2406 extending from an arm 2408. The arm 2408 extends radially outward from the carriage 1626 through the opening 2404 and orients and supports the user engagement portion 2406 in a mechanically advantageous position for manipulation by a user. The user engagement portion 2406 may further collapse, unfold, etc. into an extended state for further increasing mechanical advantage. For example, the user engagement portion 2406 may unfold outward at a hinge, like a pocket knife, or telescope outward to provide increased mechanical advantage. A pin mount 2410 of a universal joint (obscured from view) extends from the carriage 1626 and supports a first pin 2412 oriented along a first pivot (vertical) axis $P_1$. The universal joint is arranged within the arm 2408 to retain and rotatably couple the lever 2402 to the pin mount 2410, such that the lever 2402 may rotate about the first pivot (vertical) axis $P_1$ as shown by arrow R. In this manner, the first pin 2412 operates as a fulcrum, defined by the first pivot axis $P_1$, on which the arm 2408 of the lever 2402 may pivot (rotate) laterally and sideways as shown by arrow R when a lateral force is applied to the user engagement portion 2406.

The universal joint also pivotally couples the lever 2402 to the carriage 1626 such that the lever 2402 may rotate about a second pivot (horizontal) axis $P_2$ (see FIGS. 25A-25C), as shown by directional arrow D. In the illustrated embodiment, the universal joint couples the lever 2402 to the carriage 1626 such that the lever 2402 may be pivoted downward about the second pivot (horizontal) axis $P_2$ (see FIG. 25), as shown by directional arrow D, and then pivoted laterally sideways about the first pivot (vertical) axis $P_1$ normal to the second pivot axis $P_2$, as shown by rotational arrows R.

Figure 25A:
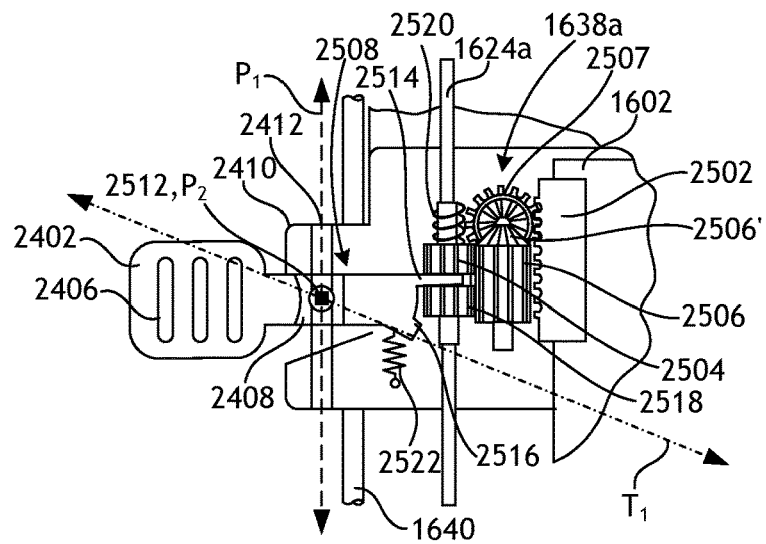
FIGS. 25A-25C illustrate an exemplary operation of the mechanism of FIG. 24.
Figure 25B:
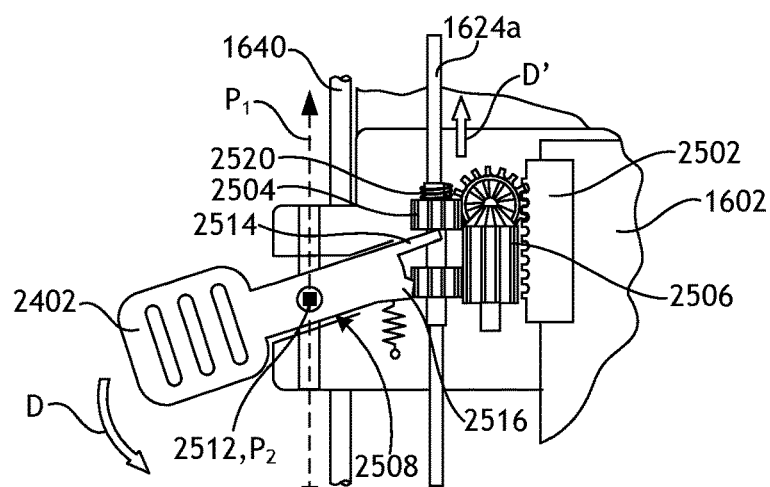
Figure 25C:
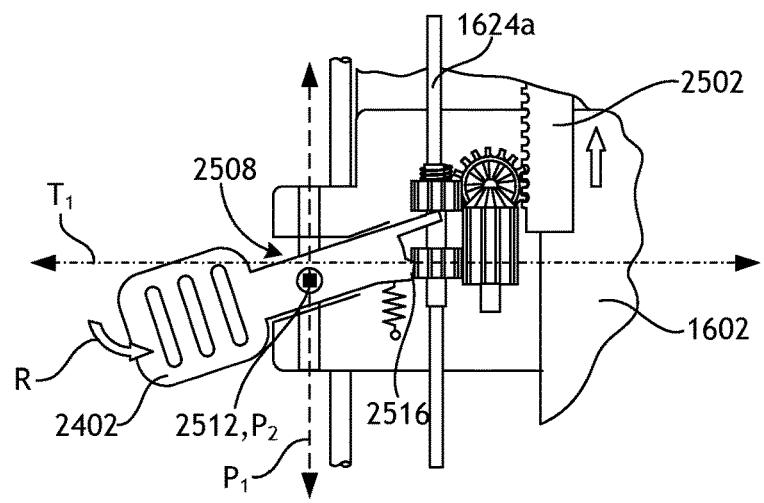

FIGS. 25A-25C are cut-away side views illustrating example operation of the mechanism 2400 of FIG. 24, according to one or more embodiments. In particular, FIG. 25A illustrates the lever 2402 in a first (engaged) position where the first spline 1624a is engaged with the first activating mechanism 1638a. FIG. 25B illustrates the lever 2402 moved or pivoted in direction D into a second position where the first spline 1624a is disengaged from the first activating mechanism 1638a and where a new manual drive source is engaged with the first activating mechanism 1638a. Lastly, FIG. 25C illustrates moving lever 2402 in direction R about the first pivot axis $P_1$ and thereby manually actuating the first activating mechanism 1638a. Thus, the lever 2402 is movable about two different axes $P_1$, $P_2$ relative to the carriage 1626, and these figures exemplify how pivoting or moving the lever 2402 about the second pivot axis $P_2$ in direction D disengages (uncouples) the first activating mechanism 1638a from the first spline 1624a while simultaneously engaging (coupling) the first activating mechanism 1638a with a new manual drive source. FIGS. 25A-C also depict how subsequently pivoting or moving the lever 2402 about the first pivot axis $P_1$, as shown by directional arrow R, manually actuates the first activating mechanism 1638a to affect opening or closure of the jaws 1610, 1612 (FIG. 16). The progressive views of FIGS. 25A-25C further illustrate how the first activating mechanism 1638a is loaded via the first spline 1624a driven by the instrument drive 1800 (FIG. 18B) when the lever 2402 is in the first position (FIG. 25A), but that the lever 2402 may be moved into the second position (FIG. 25B) were it is utilizable to manually drive or load the first activating mechanism 1638a (FIG. 25C).

In the illustrated embodiment, the elongated shaft 1602 may include or provide a closure tube that is axially movable to open or close the jaws 1610, 1612 (FIG. 16). Here, the first activating mechanism 1638a includes a driven gear 2502 provided about the exterior of the shaft 1602 (i.e., the closure tube), a spline drive gear 2504 provided on the first spline 1624a, and a pair of idler gears 2506, 2507 arranged between the spline drive gear 2504 and the driven gear 2502 to transfer rotary force from the first spline 1624a to the driven gear 2502. In the illustrated embodiment, the first idler gear 2506 intermeshes with the spline drive gear 2504 and is provided with a bevel gear 2506' that intermeshes with the second idler gear 2507, whereas the second idler gear 2507 is a pinion gear that intermeshes with both the driven gear 2502 and the bevel gear 2506' of the first idler gear 2506 to thereby transfer rotational input from the spline drive gear 2504. Also in the illustrated embodiment, the driven gear 2502 is provided as a rack gear fixed on the elongate shaft 1602 to thereby translate the elongate shaft 1602 when driven by the second idler (pinion) gear 2507; however, in other examples, the driven gear 2502 may instead be provided as a worm gear fixed about the elongate shaft 1602 to thereby carry the elongate shaft 1602 with it as it axially translates when activated by rotation of the idler gear 2506 rather than via the second idler gear 2507.

Here, rotation of the second idler gear 2507 drives the driven gear 2502 and the elongate shaft 1602 in an axial direction to thereby cause axial translation of the elongate shaft 1602. Thus, the spline drive gear 2504 rotates with the first spline 1624*a* to rotate (drive) the first idler gear 2506 and the bevel gear 2506' thereof (when intermeshed therewith as described below), rotation of the bevel gear 2506' drives (rotates) the second idler gear 2507, and rotation of the second idler gear 2507 in turn drives the driven gear 2502 to thereby translate the elongate shaft 1602 with the driven gear 2502. In other embodiments, the second idler 2507 and the bevel gear 2506' may be absent and the driven gear 2502 is provided as a worm gear fixed about the elongate shaft 1602 to thereby carry the elongate shaft 1602 with it as it axially translates when directly activated by rotation of the first idler gear 2506 that intermeshes with the worm gear threading of the driven gear 2502 rather than via the second idler gear 2507. In even other embodiments, the driven gear 2502 is provided as an internal gear (or an internally threaded gear) matable with exterior gear teeth (or threads) defined on the elongate shaft 1602 to axially translate the elongate shaft 1602 upon rotation of the driven gear 2502, relative to the elongate shaft 1602, where such relative rotation causes interaction between the internal gear (or threads) and the external gear teeth (or threads) to thereby axially translate the elongate shaft 1602. Moreover, in other non-illustrated embodiments, the spline drive gear 2504 directly engages (meshes) the driven gear 2502 such that the idler gear 2506 may be omitted in addition to omission of the second idler gear 2507.

As mentioned above, a universal joint 2508 may be provided for coupling the lever 2402 to the carriage 1626 such that the lever 2402 may rotate about both the first (vertical) pivot axis $P_1$ and the second (horizontal) pivot axis $P_2$. Thus, the arm 2408 of the lever 2402 is also pivotally (or rotatably) coupled to the carriage 1626 such that the lever 2402 may rotate about the second (horizontal) pivot axis $P_2$. In the illustrated embodiment, the carriage supports a second pin 2515 of the universal joint 2508 oriented along the second pivot axis $P_2$. As illustrated, the second pin 2512 extends through the arm 2408 of the lever 2402 to retain and rotatably couple the lever 2402 to the carriage 1626. In this manner, the second pin 2512 operates as a second fulcrum, defined by the second pivot axis $P_2$, on which the lever 2402 pivots (rotates) in direction D.

The lever 2402 may include a finger or scoop portion 2514 and a set of gear teeth 2516. The scoop portion 2514 is provided to move (lift) the spline drive gear 2504 out of engagement with the first idler gear 2506 when the lever 2402 is moved about the second pivot axis $P_2$. The set of gear teeth 2516 extends from the arm 2408 in alignment with a transverse axis Ti, such that the set of gear teeth 2516 is not operatively coupled to the first idler gear 2506 when the lever 2402 is in the first position (FIG. 25A), and such that the set of gear teeth 2516 are operatively coupled with the first idler gear 2506 when the lever 2402 is in the second position (FIG. 25B). In the illustrated embodiment, a manual drive gear 2518 is provided on the first spline 1624*a*. Here, the manual drive gear 2518 may rotate about independent of the first spline 1624*a* to operatively couple the set of gear teeth 2516 on the lever 2402 to gear teeth of the first idler gear 2506 when the lever 2402 is in the second position (FIG. 25B). The manual drive gear 2518 rotates independent of the first spline 1624*a* such that when the lever 2402 is in the first position (FIG. 25A), the manual drive gear 2518 may be rotated by the first idler gear 2506 while the set of gear teeth 2516 on the lever 2402 is positioned out of engagement (uncoupled) with the manual drive gear 2518 and within a plane defined by the second pivot axis $P_2$ and the transverse axis Ti. Thus, both the spline drive gear 2504 and the manual drive gear 2518 are mounted to the first spline 1624*a*, with the former being rotatably fixed thereon while the latter is rotatable thereon, and each engage the first idler gear 2506 when the lever 2402 when in the first position, and pulling the lever 2402 down in direction D disengages the spline drive gear 2504 from the first idler gear 2506 while simultaneously engaging the set of gear teeth 2516 (on the lever 2402) with the manual drive gear 2518. In one example, the set of gear teeth 2516 are configured as a set of one-way teeth, or as a single tooth or pawl of a ratchet, with the manual drive gear 2518 having corresponding teeth that are engaged by the set of gear teeth 2516 when the lever 2402 is rotated in a first direction but are not engaged by the set of gear teeth 2516 when the lever 2402 is rotated in an opposite direction.

In some embodiments, a biasing element 2520 (e.g., a spring) is provided for biasing the spline drive gear 2504 into engagement with the first idler gear 2506. A second biasing element 2522 (e.g., a spring) may also be provided to help maintain the lever 2402 in the first position where the set of gear teeth 2516 is uncoupled from the first activating mechanism 1638*a* (FIG. 16). Here, the first and second biasing elements 2520, 2522 bias the lever 2402 toward the first position (FIG. 25A), which can be considered a natural or default position. While the illustrated example includes both the first and second biasing elements 2520, 2522, in other examples just one may be utilized and/or other configurations of one or more biasing elements may be utilized instead. Moving the user engagement portion 2406 in the direction D (FIG. 25B) to overcome the biasing elements 2520, 2522 causes rotation of the lever 2402 and pivoting movement of the scoop portion 2514 to thereby push (slide) the spline drive gear 2504 axially along the first spline 1624*a* (against the biasing element 2520), as indicated by arrow D' (FIG. 25B), to a position where the spline drive gear 2504 is no longer engaged with the first idler gear 2506 (FIG. 25B). Moving the user engagement portion 2406 in the direction D (FIG. 25B) also intermeshes the set of gear teeth 2516 on the lever 2402 with the gear teeth of the manual drive gear 2518, which in turn is intermeshed with the first idler gear 2506, whereby the first activating mechanism 1638*a* (FIG. 16) may be actuated by moving the lever 2402 about the first pivot axis $P_1$ as indicated by direction R (FIG. 25C). Accordingly, the lever 2402 is operable to disengage the spline drive gear 2504 from the first idler gear 2506 and drive the first activating mechanism 1638*a* (FIG. 16) to affect manual opening or closing of the jaws 1610, 1612 (FIG. 16).

As discussed above, the instrument driver 1800 (FIG. 18B) is configured to actuate each of the drive outputs 1824*a-f* (FIG. 18B). For example, the instrument driver 1800 includes one or more motors (not illustrated) that cause rotation of the drive outputs 1824*a-f*. The drive outputs 1824*a-f* may each be associated with an individual motor, or two or more of the drive outputs 1824*a-f* may be associated with the same individual motor. However, one or more of the motors within the instrument driver 1800 might not be backdrivable, meaning such motors are difficult to manually rotate in either or both angular directions (i.e., clockwise and counter-clockwise). Such motors are referred to herein as "non-backdrivable" motors and are incapable (or at least very difficult) of being manually manipulated to reverse a corresponding tool function. In cases where the instrument driver 1800 incorporates non-backdrivable motor(s), it may be beneficial to provide a mechanism for decoupling the splines 1624*a-c* (FIG. 16) and/or the lead screw 1622 (FIG. 16) from the associated drive outputs 1824*a-f* such that the user may manually activate one or more functions of the surgical tool 1600 (FIG. 16).

For example, an unintended event may occur where the instrument driver 1800 (FIG. 18B) has stalled and is unable to return the surgical tool 1600 (FIG. 16) to a safe state (e.g., during a power outage). In such a scenario, the user must utilize the removable cap 1906 (FIG. 22), the distal manual actuation mechanism 2300 (FIG. 23), and/or the manual jaw opening and closure mechanism 2400 (FIG. 24) to manually actuate one or more of the spline 1624*a-c* and/or the lead screw 1622 (FIG. 16) and, thereby, manually activate the associated function of the surgical tool 1600 as described above. Thus, a clutching mechanism may be provided to allow for manual activation of one or more functions of the surgical tool 1600 without having to overcome the non-backdrivable motors within the instrument driver 1800.

Figure 26A:
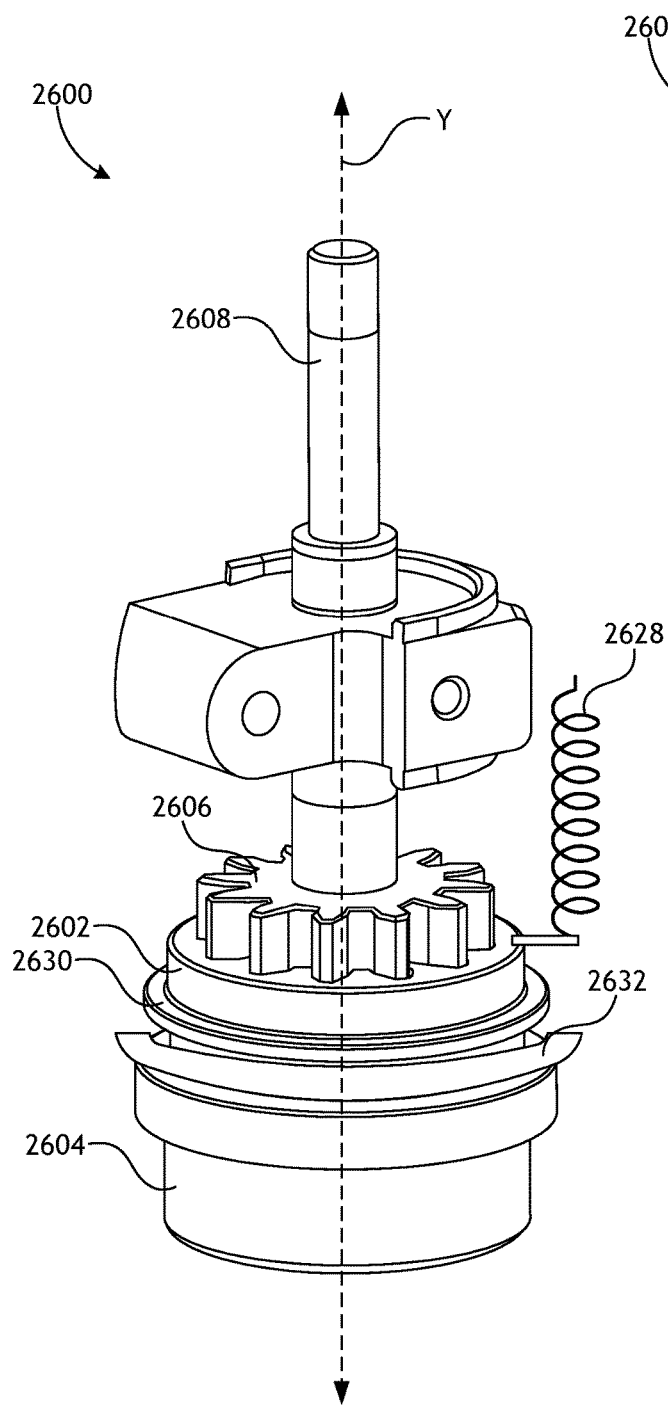
FIG. 26A illustrates a clutching mechanism, according to one or more embodiments.

FIG. 26A illustrates an example clutching mechanism 2600, according to one or more embodiments of the present disclosure. In the illustrated embodiment, the clutching mechanism 2600 includes a clutch 2602, a drive input 2604, and a spline driver 2606. The drive input 2604 may be the same as or similar to any of the drive inputs 1636*a-d* of FIGS. 18A-18B. The spline driver 2606 is fixed on a spline 2608 such that rotation of the spline 2608 correspondingly rotates the spline driver 2606 in the same angular direction. The spline 2608 may be the same as or similar to the splines 1624*a-c* of FIG. 16. The clutch 2602 is designed to selectively couple the spline driver 2606 to the drive input 2604 such that the drive input 2604 is able to rotate the spline 2608 when the clutch 2602 is properly mated with the drive input 2604. As described in more detail below, the clutch 2602 may be selectively movable axially along an axis Y of the spline 2608 to couple (mate) and uncouple (unmate) the clutch 2602 from the drive input 2604. When the clutch 2602 is uncoupled from the drive input 2604, the spline 2608 may be able to rotate independent of the drive input 2604, thus allowing manual bailout using the spline 2608. In FIG. 26A, the clutch 2602 is depicted in a first or "coupled" (engaged) position, where the spline 2608 is operatively coupled to the drive input 2604 via the clutch 2602 such that rotation of the drive input 2604 will correspondingly rotate the spline 2608.

Figure 26B:
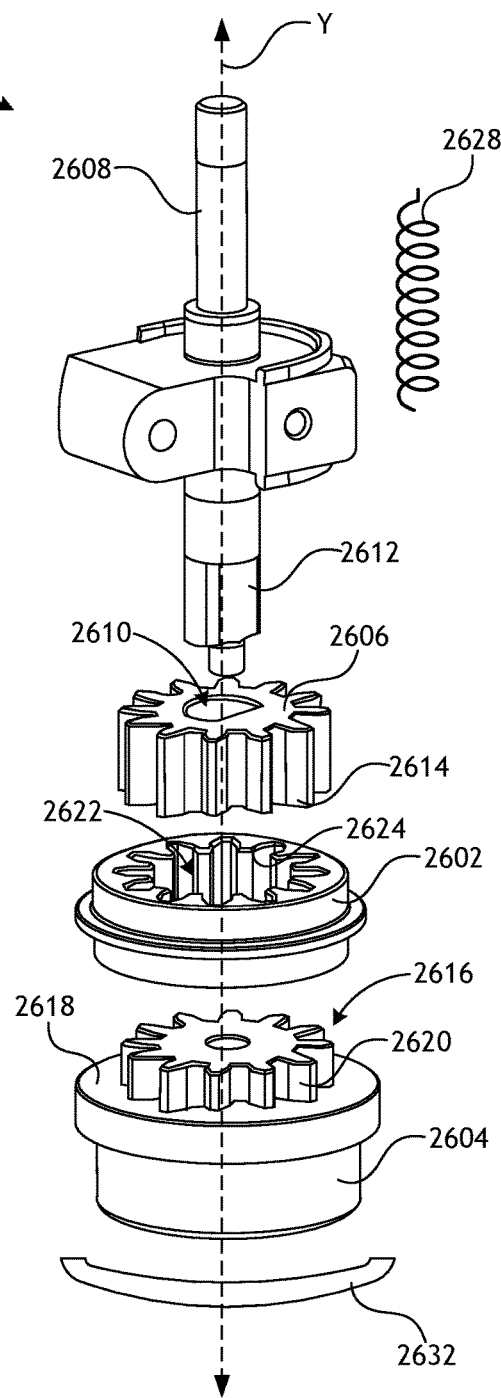
FIG. 26B illustrates an exploded view of the clutching mechanism of FIG. 26A.

FIG. 26B illustrates an exploded view of the clutching mechanism 2600. In particular, FIG. 26B illustrates the spline 2608, the spline driver 2606, the clutch 2602, and the drive input 2604 disassembled from each other along the axis Y. In the illustrated embodiment, the spline driver 2606 defines an opening 2610 arranged to receive a shaft 2612 of the spline 2608. Here, the opening 2610 and the shaft 2612 are keyed with corresponding flat surfaces, such that rotation is imparted from the spline driver 2606 to the spline 2608 and vice versa. However, the opening 2610 the shaft 2612 may be differently fixed together such that they rotate together, without departing from the present disclosure. For example, a key and corresponding key way may be provided on the opening 2610 and the shaft 2612.

The spline driver 2606 is configured as a pinion gear having a plurality of external gear teeth 2614. In addition, the drive input 2604 includes a boss 2616 protruding from a flat surface 2618 of the drive input 2604, and the boss 2616 is also configured as a pinion gear having a plurality of external gear teeth 2620. Thus, the spline driver 2606 and the boss 2616 may be referred to as the spline driver pinion gear 2606 and the bossed input pinion gear 2616, respectively.

Figure 26D:
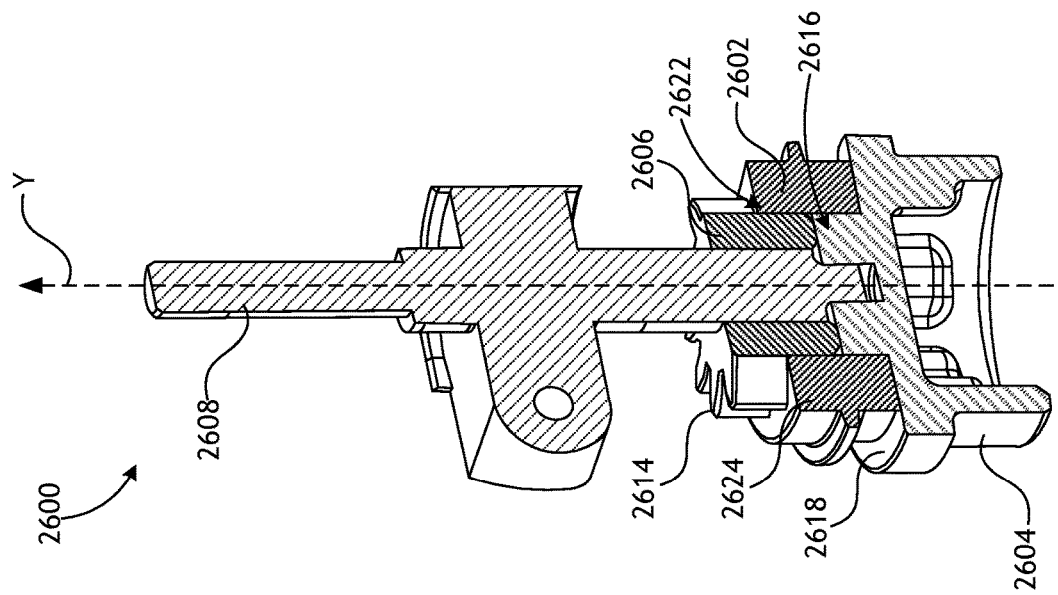
FIG. 26D illustrates a cross-sectional view of the clutching mechanism of FIG. 26A.
Figure 26C:
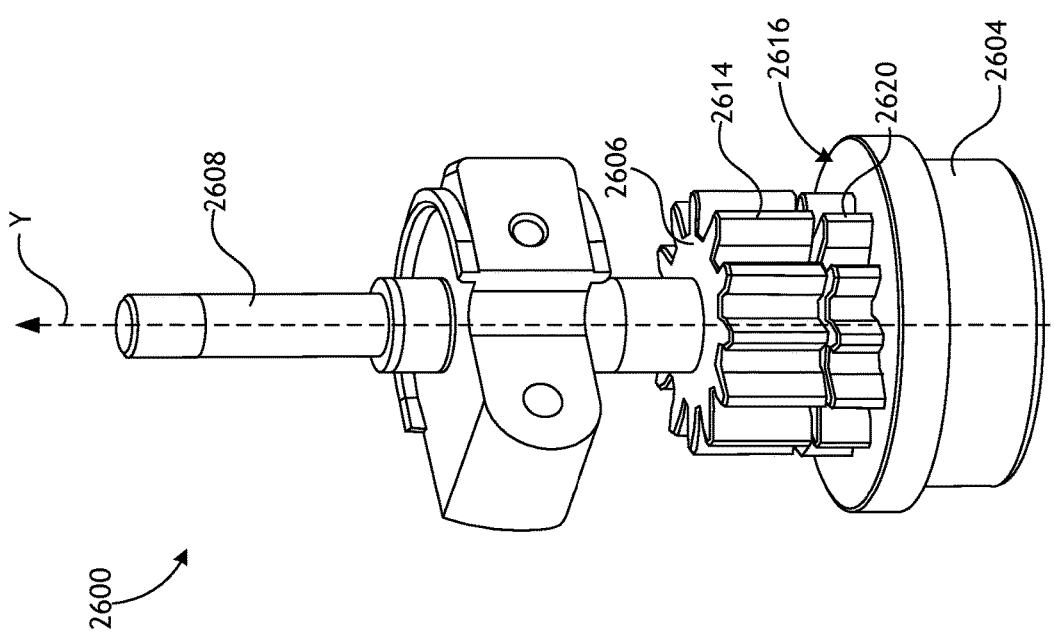
FIG. 26C illustrates a partially disassembled view of the clutching mechanism of FIG. 26A, wherein the clutch has been removed to illustrate a pinion gear of the spline driver relative to a pinion gear boss of the drive input.

FIG. 26C illustrates a partially disassembled view of the clutching mechanism 2600 of FIG. 26A. In particular, FIG. 26C illustrates the clutching mechanism 2600 with the clutch 2602 having been removed, so as to better illustrate the external gear teeth 2614 of the spline driver 2606 and the external gear 2620 of the boss 2616 relative to each other. As shown, the external gear teeth 2614, 2620 are similar in design and dimension such that they may be driven simultaneously and in unison via a single gear. Thus, as described below, the clutch 2602 may engage (mesh) with both the spline driver 2606 and the boss 2616 simultaneously. In one non-illustrated embodiment, the clutch 2602 and the spline driver 2606 form an integral, monolithic component that, while being rotationally fixed on the spline 2608, may translate axially (up and down) along the spline 2608, to couple (engage) and uncouple (disengage) the drive input 2604 with the spline 2608.

Returning to FIG. 26B, the clutch 2602 defines an internal gear 2622 having a plurality of internal gear teeth 2624. The internal gear 2622 defines an opening in the clutch 2602 within which both the boss 2616 (of the drive input 2604) and the spline driver 2606 may be received. In this manner, the internal gear teeth 2624 of the internal gear 2622 may mesh with both the external gear teeth 2614 of the spline driver 2606 and the external gear 2620 of the boss 2616.

FIG. 26D is a cross-section of the clutching mechanism 2600 and illustrates the internal gear 2622 operatively engaged with both the boss 2616 and the spline driver 2606. When the clutch 2602 is in the first (engaged) position, as illustrated in FIGS. 26A and 26D, both the boss 2616 and the spline driver 2606 are positioned within the opening defined by the internal gear 2622 of the clutch 2602 and the internal gear teeth 2624 of the internal gear 2622 are engaged (meshed) with both the external gear teeth 2614 of the spline driver 2606 and the external gear 2620 of the boss 2616, such that torque provided by the drive input 2604 may be transferred to the spline driver 2606 and the spline 2608 through the clutch 2602. Accordingly, the internal gear 2622 is designed and dimensioned such that the internal gear teeth 2624 thereof are meshable (engageable) with both sets of the external gear teeth 2614, 2620 at the same time.

In addition, the internal gear 2622 of the clutch 2602 is provided such that it may translate axially along the axis Y, from the first (engaged) position where the drive input 2604 and the spline driver 2606 are coupled together via the clutch 2602, to a second or "uncoupled" (disengaged) position where the clutch 2602 is no longer engaged (meshed) with the boss 2616 of the drive input 2604. When the clutch 2602 is disengaged, the spline 2608 and the spline driver 2606 are able to rotate independent of (and relative to) the drive input 2604.

In some embodiments, the clutch 2602 is biased into the first (engaged) position, such that the engaged position is the natural or default state of the clutching mechanism 2600. Thus, a biasing element 2628 may be provided to apply a biasing force on the clutch 2602 and thereby urge the internal gear 2622 thereof into a meshed and engaged relationship with both the boss 2616 and the spline driver 2606. In some examples, the biasing element 2828 is a spring, however other types of biasing devices may be utilized. In this manner, no user intervention is needed for the instrument driver 1800 (FIG. 18B) to drive the splines 1624*a-c* and/or the lead screw 1622 (FIG. 16), but the user may utilize the clutching mechanism 2600 to disengage the splines 1624a-c and/or the lead screw 1622 from the drive inputs 1636a-d such that one or more functions of the surgical tool 1600 may be manually activated without having to overcome any resistance that may otherwise exist due to the presence of a non-backdrivable motor within the instrument driver 1800 (FIG. 18B).

In such embodiments, however, the biasing force applied on the clutch 2602 by the biasing element 2828 will need to be overcome to move the clutch 2602 into the second (disengaged) position. In the illustrated embodiment, the clutch 2602 includes a ring 2630 (FIG. 26A) extending around a periphery of the clutch 2602, and a bailout armature 2632 may be used to engage the ring 2630 and thereby transition the clutch 2602 along the axis Y to the second (disengaged) position. Here, the bailout armature 2632 is illustrated as a U-shaped or ring shaped structure surrounding the clutch 2602 to engage the ring 2630 thereof. However, the bailout armature 2632 may be differently configured without departing from the present disclosure. For example, the bailout armature 2632 may comprise a pair of parallel plates between which the ring 2630 of the clutch 2602 sandwiched.

FIGS. 27A-27D illustrate example operation of the clutching mechanism 2600, according to one or more embodiments. In particular, FIGS. 27A and 27B illustrate isometric and cross-sectional views, respectively, of the clutching mechanism 2600 when the clutch 2602 is in the first (engaged) position, and FIGS. 27C and 27D illustrate respective isometric and cross-sectional views of the clutching mechanism 2600 when the clutch 2602 is shifted into the second (disengaged) position.

In FIG. 27A, the biasing element (not shown) applies a biasing force on the clutch 2602 to thereby urge the clutch 2602 towards the drive input 2604, as shown by arrow $B_1$, such that the internal gear 2622 of the clutch 2602 engages (meshes with) the bossed input pinion gear 2616 (FIG. 27B). Accordingly, when the clutch 2602 is shifted into position where it engages both the bossed input pinion gear 2616 (of the drive input 2604) and the spline driver 2606, the spline 2608 is engaged with one or more of the drive outputs 1824a-f (FIG. 18B) of the instrument driver 1800 (FIG. 18B), such that the activating mechanisms 1638a-c (FIG. 16) are actuatable by the instrument driver 1800 (FIG. 18B). However, the user may disengage the spline 2608 from the instrument driver 1800 (FIG. 18B) by moving or shifting the clutch 2602 into the second (disengaged) position as shown in FIGS. 27C and 27D. For example, the user may activate the armature 2632 (FIG. 26A) to engage the ring 2630, with force sufficient to overcome the biasing force exerted by the biasing element (not shown), and thereby translate (or lift) the clutch 2602 along the axis Y in a direction opposite $B_1$, as shown by arrow $B_2$. Accordingly, when the clutch 2602 is shifted out of engagement with the bossed input pinion gear 2616, the spline 2608 is similarly disengaged from the instrument driver 1800 (FIG. 18B), such that the activating mechanisms 1638a-c (FIG. 16) may be manually operated, as described above.

Figure 28:
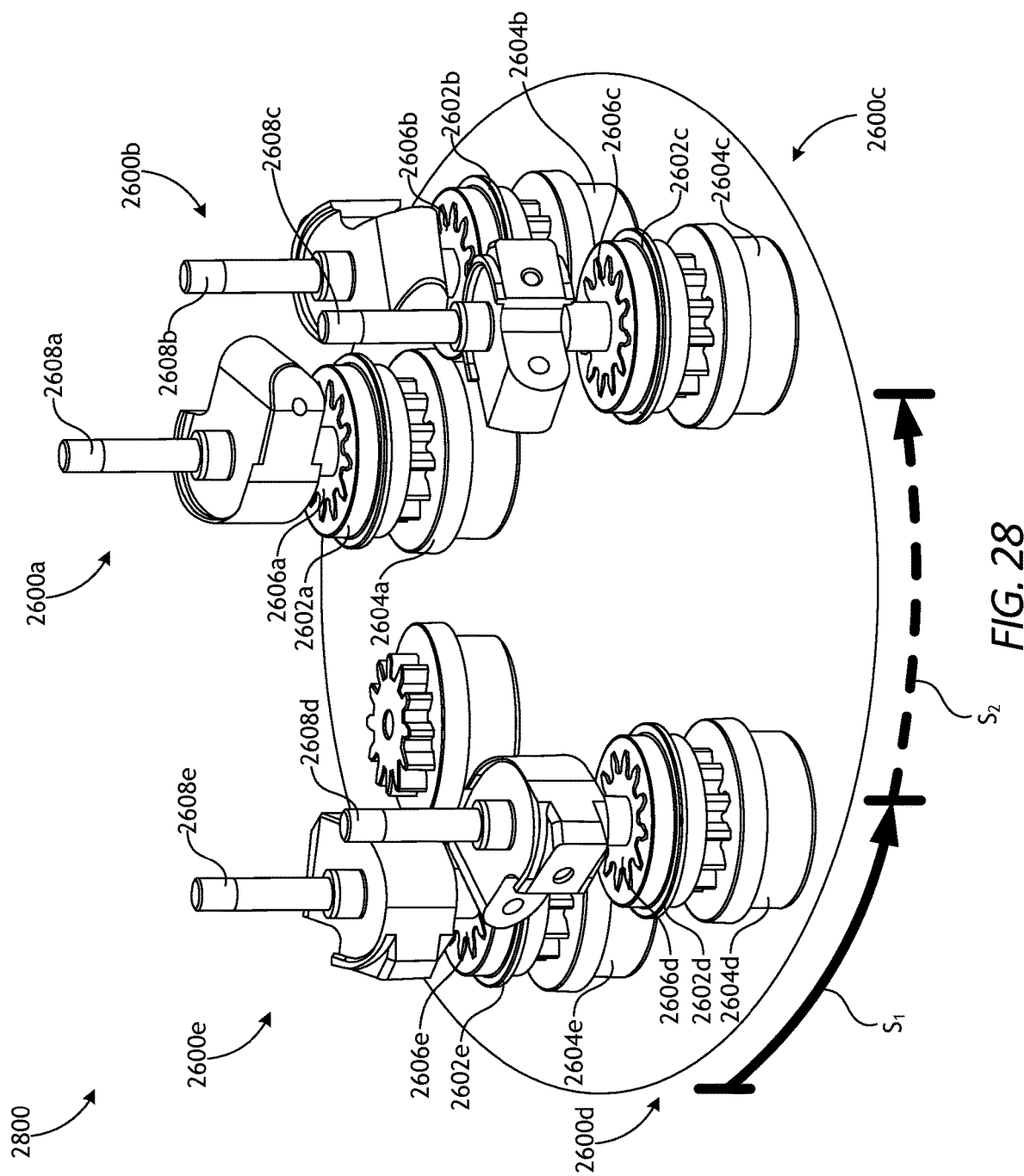
FIG. 28 illustrates a multi-clutching assembly utilizable to disengage two or more of the clutching mechanisms of FIG. 26A, according to one or more embodiments of the present disclosure.

With regard to FIGS. 26A-26D and FIGS. 27A-27D, the clutching mechanism 2600 is illustrated and described with reference to a single drive input 2604. However, the clutching mechanism 2600 may be provided on more than one drive input 2604. For example, each of the drive inputs 1636a-d (FIG. 18B) may be associated with an individual clutching mechanism 2600. FIG. 28 illustrates a multi-clutching assembly 2800 that can be utilized to disengage two or more of the clutching mechanisms 2600, according to one or more embodiments of the present disclosure. In the illustrated embodiment, a plurality of clutching mechanisms 2600a-e are provided similar to the clutching mechanism 2600 described above. Accordingly, each of the clutching mechanisms 2600a-e includes a respective clutch 2602a-e, a respective drive input 2604a-e, and a respective spline driver 2606a-e arranged on a respective spline 2608a-d. Also, one or more biasing elements (not illustrated) are provided to bias and urge the clutches 2602a-e into engagement with their respective drive input 2604a-e.

In the illustrated embodiment, the multi-clutching assembly 2800 also includes one or more bailout armatures (not illustrated). The one or more bailout armatures is/are movable to shift or move the corresponding clutches 2602a-e out of engagement with the respective drive inputs 2604a-e, such that each of the respective splines 2608a-d is uncoupled from the respective drive input 2604a-e, thus allowing manual actuation of the splines 2608a-e. In some examples, the bailout armature is a plate positioned in engagement with each of the clutches 2602a-e to couple or decouple the associated drive inputs 2604a-e. In some examples, the one or more bailout armatures comprises an outer ring arranged at (least partially about) the first end 1618a (FIG. 18B) having one or more inwardly extending wedge features (ledges) positioned and oriented to engage the rings 2630 (FIG. 26A) of the clutches 2602a-e upon rotation of the outer ring. A cam profile may be provided on the inwardly extending wedge feature(s) to decouple based upon a certain amount of rotation of the outer ring and/or to stage decoupling based on incremental rotation of the outer ring such that one or more of the drive inputs 2604a-e are decoupled in series with as the outer ring is incrementally rotated. Accordingly, a user may activate the multi-clutching assembly 2800 to actuate the bailout armature(s) and thereby decouple the spline(s) 2608a-e from the instrument driver 1800 (FIG. 18B).

In some embodiments, rotating the multi-clutching assembly 2800 along a first arcuate length $S_1$ may be configured to actuate the bailout armature(s) to decouple the spline(s) 2608a-e from the instrument driver 1800 (FIG. 18B). In such embodiments, the surgical tool 1600 (FIG. 18B) may remain coupled to the instrument driver 1800 (FIG. 18B) as the multi-clutching assembly 2800 is rotated along the first arcuate length $S_1$.

In some embodiments, the multi-clutching assembly 2800 may also be incorporated into the action of decoupling the surgical tool 1600 (FIG. 18B) from the instrument driver 1800 (FIG. 18B), such that actuation of the bailout armature may also result in decoupling of the surgical tool 1600 (FIG. 18B) from the instrument driver 1800 (FIG. 18B). In the illustrated embodiment, the multi-clutching assembly 2800 may be rotated further along a second arcuate length $S_2$ past the first arcuate length $S_1$ and thereby decouple the surgical tool 1600 (FIG. 18B) from the instrument driver 1800 (FIG. 18B). Thus, in such embodiments, the first arcuate length $S_1$ of user input on the multi-clutching assembly 2800 may actuate the bailout armature to disengage the splines 2608a-d from the instrument driver 1800 (FIG. 18B), and further activation of the multi-clutching assembly 2800 via the second arcuate length $S_2$ of user input decouples the surgical tool 1600 (FIG. 18B) from the instrument driver 1800 (FIG. 18B). As mentioned above, the bailout armature may comprise an outer ring arranged about the first end 1618a (FIG. 18B) and having one or more inwardly extending wedge features (ledges) with cam profiles that engage the rings 2630 (FIG. 26A) of the clutches 2602a-e upon rotation of the outer ring. In this example, rotation of the outer ring the first arcuate length $S_1$ causes the bailout armature to engage the clutches 2602a-e to thereby uncouple one or more of the splines 2608a-d from the respective drive input 2604a-e, and further rotation of the outer ring the second arcuate length $S_2$ may cause the inwardly extending wedge features of the outer ring to drive one or more ejection legs against the instrument driver 1800 (FIG. 18B) to thereby press the surgical tool 1600 (FIG. 18B) off of the instrument driver 1800.

In some embodiments, one or more of the clutching mechanisms 2600a-e may be designed to permanently disable one or more functions of the surgical tool 1600 (FIG. 18B) when activated by the user. For example, the clutching mechanism 2600 (FIGS. 26A-26D) may be provided with a catch to retain the clutch 2602 (FIGS. 26A-26D) once shifted into the first (engaged) position. Here, by inhibiting the clutch 2602 (FIGS. 26A-26D) from shifting back into engagement with the bossed input pinion gear 2616 (FIGS. 26A-26D), the associated drive input 2604 (FIGS. 26A-26D) remains disengaged and uncoupled from the associated spline 2608 (FIGS. 26A-26D). As described above, the bailout armature 2632 may be plate like structures or horseshoe shaped structures. In some examples, the bailout armature 2632 is an outer ring arranged about the first end 1618a (FIG. 18B) and having one or more inwardly oriented cam profiles that engage the ring 2630, which may be contoured to follow the camp profile, such that clockwise rotation of the outer ring drives the clutch 2602 apart from the drive input 2604 and counter-clockwise rotation of the outer ring drives the clutch 2602 into engagement with the drive input 2604. Here, a biasing element (e.g., a compression spring) may be provided to bias the outer ring towards an engaged position (e.g., biased in the counter-clockwise direction). In another example, a biasing element (e.g., a compression spring) may be provided for constantly biasing the clutch 2602 toward engagement. The catch may comprise various mechanisms arranged to retain the clutch 2602 such that it is "not resettable." For example, the catch may include a leaf spring feature that engages the clutch 2602 sideways, or the catch may comprise a side sprung bump/indent that slides into a corresponding detent/indent; and such catch mechanisms may be configured to be permanently or temporarily inhibit resetting. As used herein, the term "armature" may refer to a power generating component in an electrical system that carries electrical current to thereby create torque or force that may be imparted on one or more additional components, such as the clutch 2602, to thereby cause movement of such one or more additional components. Also or instead, the term "armature" may refer to an intermediate component of a mechanical system that, when acted on by a first component, directly or indirectly transfer torque or force to one or more additional components, such as the clutch 2602, to thereby cause movement in such one or more additional components.

Figure 29:
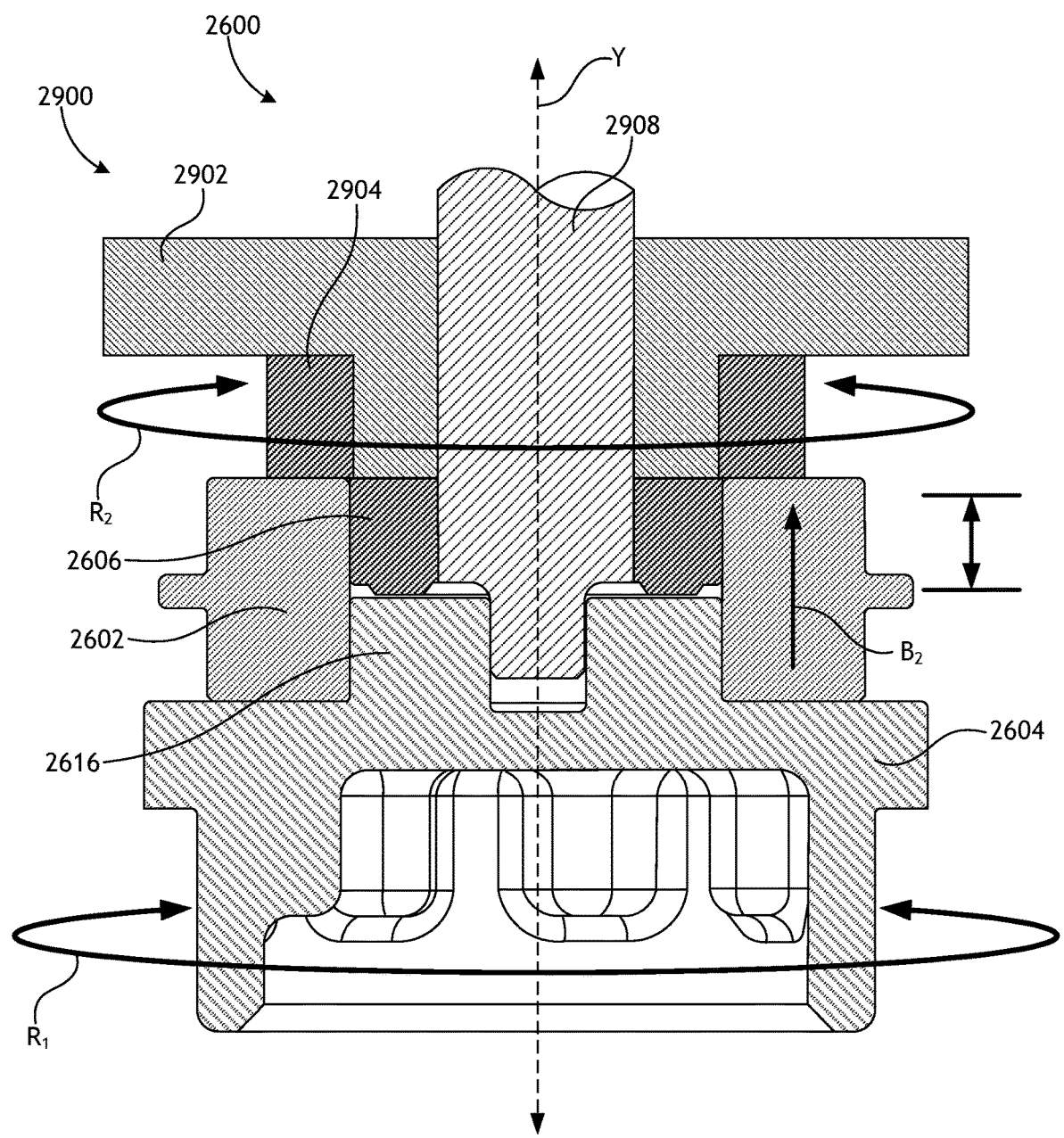
FIG. 29 illustrates the clutching mechanism of FIG. 26A incorporating a manual override feature, according to one or more embodiments.

FIG. 29 is a cross-sectional side view of the clutching mechanism 2600 of FIG. 26A incorporating an example manual override feature 2900, according to one or more embodiments. In the illustrated embodiment, the manual override feature 2900 includes a manual driver 2902 having a plurality of external gear teeth 2904. Accordingly, the manual driver 2902 and the external gear teeth 2904 thereof may collectively be referred to as a "manual driver gear." When the clutch 2602 is translated or shifted along the axis Y towards the manual driver 2902, as shown by arrow $B_2$, and out of engagement with the bossed input pinion gear 2616 (of the drive input 2604), the internal gear 2622 (FIG. 26B) of the clutch 2602 will engage both the external gear teeth 2614 (FIG. 26B) of the spline driver 2606 and the external gear teeth 2904 of the manual driver 2902. In this manner, the clutch 2602 is movable, from the first position where the clutch 2602 couples the spline driver 2606 to the drive input 2604 such that the spline 2608 is engageable by the instrument driver 1800 (FIG. 18B), to the second position where the spline driver 2606 is decoupled from the drive input 2604 and where the clutch 2602 instead couples the spline driver 2606 to the manual driver 2902 such that the spline 2608 is engageable by the manual driver 2902. Thus, the manual override feature 2900 may be directly enabled or disabled by actuation of the clutch 2602, such that the clutch 2602 is shiftable between the first position, where the instrument driver 1800 (FIG. 18B) engages and is utilizable to drive the spline 2608 as indicated by robotic rotational input arrow $R_1$, to the second position, where the manual driver 2902 engages and is utilizable to drive the spline 2608 as indicated by human rotational input arrow $R_2$. Thus, while FIG. 29 illustrates the clutch 2602 in the first position where it couples the spline 2608 to the drive input 2604, the clutch 2602 is movable in direction $B_2$ to couple the spline 2608 to the manual driver 2902.

Figure 30:
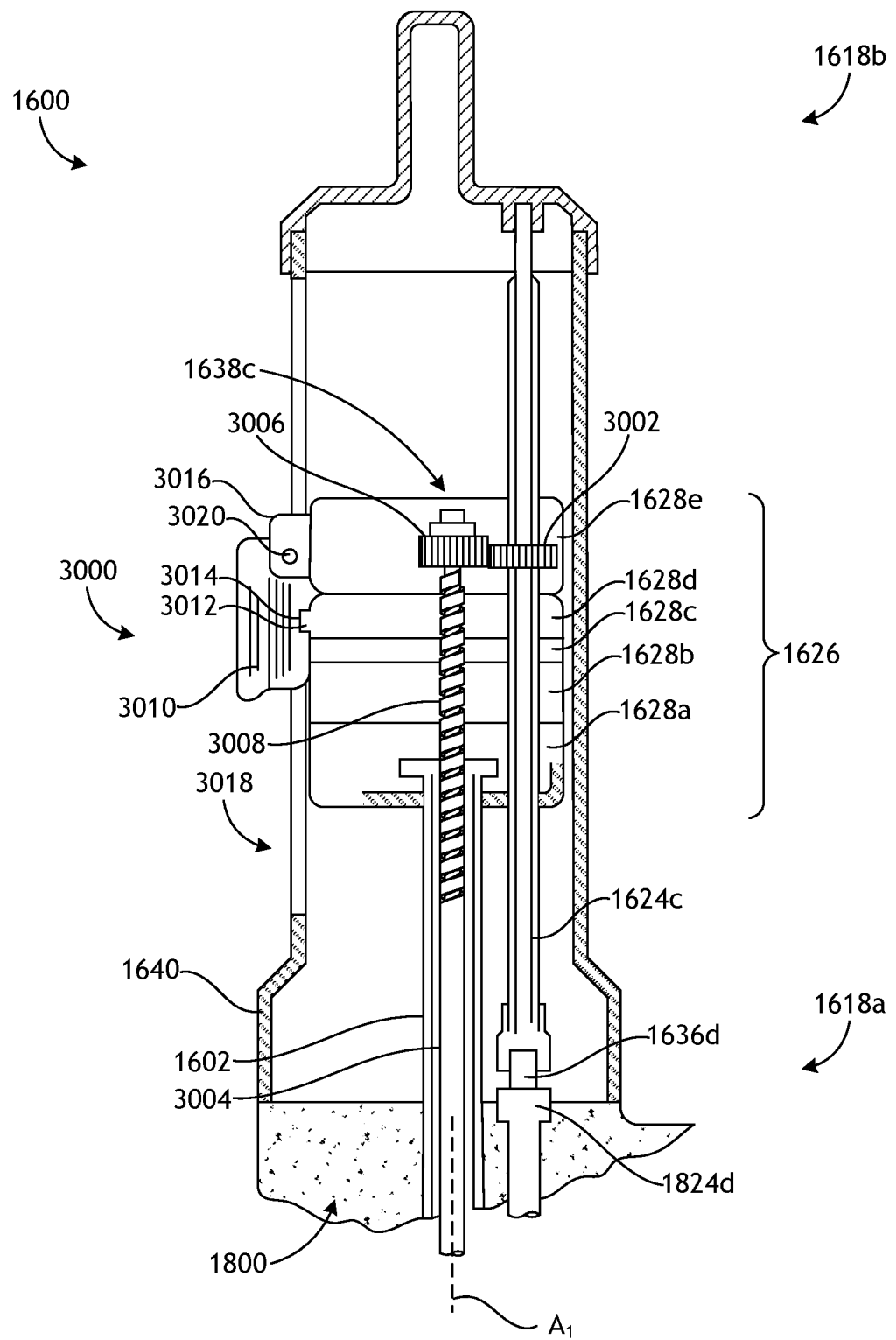
FIG. 30 illustrates a bailout mechanism, according to one or more embodiments.

FIG. 30 illustrates an example bailout mechanism 3000, according to one or more alternate embodiments of the present disclosure. In the illustrated embodiment, a drive gear 3002 is provided on the third spline 1624c to engage and thereby activate the third activating mechanism 1638c upon rotation of the third spline 1624c. As described above, activation of the third activating mechanism 1638c causes the cutting element at the end effector 1604 (FIG. 16) to advance or retract. As illustrated, the third activating mechanism 1638c is arranged in and otherwise associated with the fifth layer 1628e of the carriage 1626, and the drive gear 3002 is rotatably mounted within the fifth layer 1628e. In addition, the drive gear 3002 is slidingly provided on the third spline 1624c such that the drive gear 3002 may slide along the third spline 1624c with the fifth layer 1628e while rotating in unison with the third spline 1624c and relative to the fifth layer 1628e.

The third activating mechanism 1638c includes a drive or firing rod 3004 and a pinion gear 3006 that meshes with the drive gear 3002 such that rotation of the drive gear 3002 rotates the pinion gear 3006. The pinion gear 3006 may define internal threads that mesh with an externally threaded portion 3008 of the firing rod 3004 such that rotation of the pinion gear 3006 axially translates the firing rod 3004 along the longitudinal axis $A_1$. The cutting element (e.g., knife) is attached at a distal end (not shown) of the firing rod 3004 and may thus be advanced or retracted as the firing rod 3004 translates distally or proximally, respectively, upon rotation of the pinion gear 3006 via the drive gear 3002. Accordingly, the third activating mechanism 1638c fires the cutting element on the firing rod 3004 upon rotation of the third spline 1624.

According to embodiments of the present disclosure, the fifth layer 1628e may be separable from the remaining layers 1628a-d of the carriage 1626. In the illustrated embodiment, the fifth layer 1628e is the proximal-most layer of the carriage 1626 and may be separated from the distal layers (i.e., layers 1628a-d) of the carriage 1626 via operation of the bailout mechanism 3000, as hereinafter described. In other embodiments, however, one or more layers may be provided on a proximal side of the fifth layer 1628e and removing the fifth layer 1628e will correspondingly remove such additional layers from the carriage 1626.

In the illustrated embodiment, the bailout mechanism 3000 includes a latch 3010 operatively coupled to the fifth layer 1628e and a locking feature 3012 provided on one or more of the layers distal to the fifth layer 1628e. In the illustrated embodiment, the locking feature 3012 is provided on the fourth layer 1628d, but could alternatively be provided on any of the other distal layers (i.e., layers 1628a-c) in addition to or instead of the fourth layer 1628d. Here, the locking feature 3012 is a keeper or strike protruding radially outward from the fourth layer 1628d, and the latch 3010 includes a corresponding recess 3014 dimensioned in size to receive and retain the locking feature 3012 when the latch 3010 is in a locked position as shown in FIG. 30.

Figure 31:
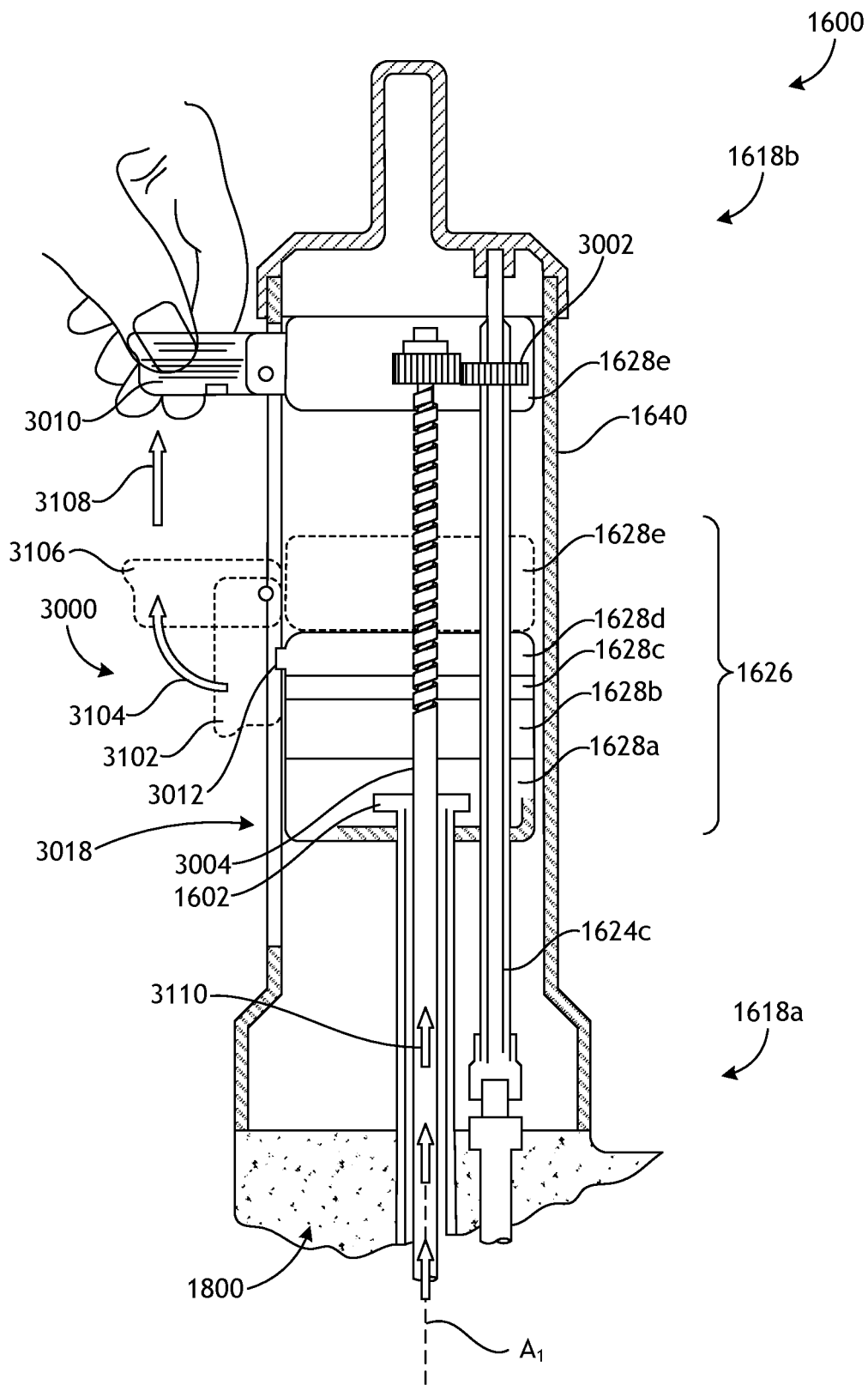
FIG. 31 illustrates example operation of the bailout mechanism, according to one or more alternate embodiments of the present disclosure.

The latch 3010 is rotatably or pivotally mounted to the fifth layer 1628e such that it may rotate or pivot between a locked position, as shown in FIG. 30, where the latch 3010 catches and retains (engages) the locking feature 3012, and an unlocked position, as shown in FIG. 31, where the latch 3010 is disengaged from the locking feature 3012. In the illustrated embodiment, a fin 3016 is provided on the fifth layer 1628e and, as shown, the fin 3016 laterally or radially extends from the fifth layer 1628e outward through a window 3018 defined in the shroud 1640. The latch 3010 is pivotally or rotatably mounted to the fin 3016 such that the latch 3010 is accessible from an exterior of the surgical tool 1600 to move the latch 3010 between the locked and unlocked positions. As shown in FIG. 30, a pin 3020 may couple the latch 3010 to the fin 3016, whereby the pin 3020 defines an axis of rotation and hinge about which the latch 3010 is movable (pivotable) between the locked and unlocked positions. However, the latch 3010 may be differently mounted on the fifth layer 1628e to permit pivoting of the latch 3010 between the locked and unlocked positions without departing from the present disclosure.

FIG. 31 illustrates example operation of the bailout mechanism 3000, according to one or more alternate embodiments of the present disclosure. In the illustrated embodiment, the bailout mechanism 3000 is initially provided in the locked or engaged position, as shown with phantom lines 3102, where the latch 3010 is engaged with the locking feature 3012 to thereby couple the fifth layer 1628e to the remaining layers (i.e., layers 1628a-c) of the carriage 1626. The latch 3010 may be pivoted or rotated out of the locked or engaged position 3102, as shown by the arrow 3104, and to the unlocked or unengaged position 3106 to thereby decouple the fifth layer 1628e from the remaining layers (i.e., layers 1628a-c) of the carriage 1626. Once the fifth layer 1628e is detached, the latch 3010 may be manually pulled proximally (or upward) towards the second end 1618b, as shown by arrow 3108, to separate the fifth layer 1628e from the remaining layers of the carriage 1626. Pulling the latch 3010 proximally 3108 will correspondingly pull the firing rod 3004 and the cutting element operatively coupled to the distal end of the firing rod 3004 in the proximal direction 3110.

In one embodiment, the latch 3010 is able to be pulled proximally 3108 up to sixty (60) millimeters, however, it may be pulled to different lengths/distances, without departing from the present disclosure. Moreover, as the fifth layer 1628e is pulled proximally toward the second end 1618b, the drive gear 3002 slides along the third spline 1624c as the fifth layer 1628e carries it in the proximal direction.

Accordingly, the bailout mechanism 3000 is utilizable to manually retract the cutting element of the end effector 1604 (FIG. 16) by uncoupling the associated layer (i.e., the fifth layer 1628e) from the other distal layers (i.e., layers 1628a-c) of the carriage 1626 and then moving (pulling) the latch 3010 proximally towards the second end 1618b. In these embodiments, the step of uncoupling includes pivoting the latch 3010 from a locked position into an unlocked position, and the step of moving (or pulling) the latch 3010 proximally includes retracting the firing rod 3004 within the elongate shaft 1602 to thereby pull and retract the cutting element in the proximal direction.

FIG. 32 illustrates the bailout mechanism 3000 incorporating a bailout assist mechanism 3200, according to one or more embodiments of the present disclosure. The bailout mechanism 3000 and the bailout assist mechanism 3200 are utilizable in bailout scenarios where the jaws 1610, 1612 (FIG. 16) of the end effector 1604 (FIG. 16) are stuck on tissue and the robotic manipulator 1800 (FIG. 18) is unable to retract the cutting element (not shown). In FIG. 32, the bailout mechanism 3000 is depicted as engaged and holding the layers 1628a-e of the carriage 1626 together. A user may trigger the bailout mechanism 3000 to decouple the fifth layer 1628e of the carriage 1626 from the remaining layers 1628a-d, as generally described above, and then utilize the bailout assist mechanism 3200 to help move (lift) the fifth layer 1628e away from the distal layers 1628a-d and thereby retract the cutting element (not shown). Thereafter, the user could manually open the jaws 1610, 1612 as described herein.

In the illustrated embodiment, the bailout assist mechanism 3200 includes a user engagement feature 3202. Here, the user engagement feature 3202 is a screw feature designed to receive an Allen wrench, but the user engagement feature 3202 may be differently configured to receive different tools, without departing from the present disclosure. Also, the user engagement feature 3202 is accessible from outside the surgical tool 1600, such as through the window 3018 defined in the shroud 1640, such that the Allen wrench may be inserted into and through the window 3018 to access the user engagement feature 3202. However, in other embodiments, the user engagement feature 3202 may extend from and protrude through the window 3018 in the shroud 1640.

The bailout assist mechanism 3200 is provided to assist separating one or more proximal layers from the remaining distal layers of the carriage 1626. Accordingly, the bailout assist mechanism 3200 is constrained by or within the layer(s) that it is operable to separate from the remaining layers of the carriage 1626. In the illustrated embodiment, the bailout assist mechanism 3200 is provided to assist separating the fifth layer 1628e from the other layers 1628a-d distal to the fifth layer 1628e. Here, the user engagement feature 3202 is provided in a pillow block 3204 provided on an upper surface 3206 of the fifth layer 1628e. In other embodiments, however, the user engagement feature 3202 and its operating mechanism may be provided within the fifth layer 1628e. In the illustrated embodiment, the removable cap 1906 includes a raised portion 3208 provided to accommodate the pillow block 3204 when the carriage 1626 is translated towards the second end 1618b, for example, into its proximal most position. Here, the removable cap 1906 includes a window portion 3210 that aligns with the window 3018 of the shroud 1640, such that they together define a continuous window through which the user engagement feature 3202 is accessible, even when the carriage 1626 is translated into its proximal most position at the second end 1618b. In this manner, the carriage 1626 may be fully translated proximally without interference between the pillow block 3204 and the removable cap 1906 such that the pillow block 3204 does not inhibit or decrease functionality provided by translation of the carriage 1626.

FIG. 33A-33B illustrate example operation of the bailout assist mechanism 3200 in separating one or more proximal layers of the carriage 1626 from the remaining distal layers, according to one or more embodiments of the present disclosure. The user engagement feature 3202 includes or otherwise forms part of a jack (or lift or spacer) 3302 having an extendible leg 3304 that is axially translatable upon rotation (actuation) of the user engagement feature 3202. In the illustrated example, the user engagement feature 3202 is matable with an Allen wrench 3306 to activate the jack 3302 and thereby advance the extendible leg 3304 from a fully retracted position, as shown in FIG. 33A, toward an extended position, as shown in FIG. 33B. In other examples, the user engagement feature 3202 may be activated using another type of tool besides the Allen wrench 3306, without departing from the present disclosure. In other examples, the user engagement feature 3202 may comprise a ratcheting mechanism, whereby a user applies successive upward and downward motions (rather than rotational input) to incrementally advance the extendible leg 3304 with each such downward (or upward) motion.

With reference to FIG. 33A, the latch 3010 is in the locked or engaged position, such that the fifth layer 1628e is coupled to the remaining layers 1628a-d of the carriage 1626. Here, the jack 3302 is in a nonextended (retracted) condition because the carriage 1626 layers are locked together. Also, FIG. 33A illustrates a condition where the activating mechanism 1638c has advanced the drive rod 3004 distally and into the most distal end-of-stroke position. In the event the firing rod 3004 needs to be retracted to correspondingly retract the cutting element (not shown) operatively coupled to the distal end of the driving rod 3304, the user may manually open the latch 3010 to unlock the fifth layer 1628e from the remainder of the carriage 1626, and then insert the Allen wrench 3306 into the user engagement feature 3202 to manually crank the user engagement feature 3202. As the user engagement feature 3202 is being actuated, the leg 3304 will extend distally to urge the fifth layer 1628e to separate from the remainder of the carriage 1626 and thereby retract the driving rod 3304 and the cutting element.

In FIG. 33B, the latch 3010 is shown after having been pivoted or rotated 3104 into an unlocked position such that the jack 3302 may be activated to separate the fifth layer 1628e. Here, the wrench 3306 is rotated or cranked as shown by arrow $W_1$, and rotating or cranking $W_1$ the wrench 3306 advances the extendible leg 3304 from the jack 3302, as shown by arrow $W_2$, to thereby separate the fifth layer 1628e from the remaining distal layers of the carriage 1626. By separating the fifth layer 1628e from the distal layers 1628a-d, the jack 3202 may push the fifth layer 1628e proximally, towards the second end 1618b. The cutting element (not shown) is operatively coupled to the distal end of the firing rod 3004, which is operatively connected to the fifth layer 1628e. Thus, the firing rod 3004 and the cutting element move with the fifth layer 1628e proximally towards the second end 1618b as the jack 3202 expands the extendible leg 3304 to push against distal layers (e.g., the fourth layer 1628d). In this manner, the bailout assist mechanism 3200 may be provided for manually retracting (i.e., bailing out) the cutting element by a distance $W_3$, for example, sixty (60) millimeters.

FIGS. 34A and 34B illustrate a bailout mechanism 3400 for a backdrivable motor, according to one or more additional embodiments of the present disclosure. In the illustrated embodiment, the bailout mechanism 3400 includes a lever 3402 operatively coupled to the third spline 1624c, which is responsible for actuating the third activating mechanism 1638c and thereby driving the firing rod 3004 and advancing or retracting the cutting element (not shown) operatively coupled to a distal end thereof. As hereinafter described, the lever 3402 is coupled to the third spline 1624c in a manner that allows the third spline 1624c to rotate relative to the lever 3402 when the lever 3402 is in a non-engaged position as depicted in FIG. 34A.

As illustrated, a drive gear 3404 is provided on and rotates with the third spline 1624c. The drive gear 3404 is arranged to mesh with the pinion gear 3006 of the third activating mechanism 1638c such that rotation of the drive gear 3404 drives the pinion gear 3006 and thereby activates the third activating mechanism 1628c. As mentioned above, internal threads of the pinion gear 3006 mesh with the threaded portion 3008 of the firing rod 3004 such that rotation of the pinion gear 3006 axially translates the firing rod 3004 along the longitudinal axis $A_1$. The cutting element (e.g., knife) operatively coupled to the distal end of the firing rod 3004 may thus be advanced or retracted as the firing rod 3004 translates distally or proximally, respectively, upon rotation of the pinion gear 3006 via the drive gear 3404.

The bailout mechanism 3400 may further include a manual drive gear 3406 provided on a proximal end of the third spline 1624c. The manual drive gear 3406 rotates with the third spline 1624c and is matable with the lever 3402 such that rotation of the lever 3402 causes rotation of the third spline 1624c and the drive gear 3404 to thereby manually activate the third activating mechanism 1628c. In addition, the lever 3402 provides mechanical advantage for manually actuating the third spline 1624c and manually back-driving the motor.

Also in the illustrated embodiment, a removable cover 3408 is provided on or otherwise forms part of the removable cap 1906. When assembled on the removable cap 1906 as shown in FIG. 34A, the removable cover 3408 encloses the lever 3402 to inhibit unintentional manipulation of the lever 3402. The removable cover 3408 includes a gripping location 3410 engageable by the user to remove the removable cover 3408 from the removable cap 1906. The removable cover 3408 defines an interior volume 3412 within which the lever 3402 is disposed when the removable cover 3408 is installed on the removable cap 1906. Also, a spacer bar or "spacer" 3414 is integrated into the removable cover 3408. The spacer bar 3414 extends radially into the interior volume 3412 of the removable cover 3408 and, when the removable cover 3408 is installed on the removable cap 1906, the spacer bar 3414 rests under the lever 3402 to retain and support the lever 3402 in a non-engaged position, as depicted in FIG. 34A, where the lever 3402 does not engage the manual drive gear 3406 of the third spline 1624c. By removing the removable cover 3408, the spacer bar 3414 is withdrawn from underneath the lever 3402, such that the lever 3402 is no longer supported and retained in the non-engaged position, and then the user may move the lever 3402 into an engaged position, as depicted with reference to FIG. 34B, where the lever 3402 does engage the manual drive gear 3406 of the third spline 1624c.

The manual drive gear 3406 is rotatable relative to (independent of) the lever 3402 when the lever 3402 is positioned in the non-engaged position as exemplified in FIG. 34A. In some embodiments, to accommodate this relative movement between the manual drive gear 3406 and the lever 3402, a bore 3416 is provided in the lever 3402 for receiving the manual drive gear 3406 and the third spline 1624c. The bore 3416 and the manual drive gear 3406 may include corresponding keyed surfaces for coupling the manual drive gear 3406 to the lever 3402 when the lever 3402 is in the non-engaged position. For example, at least one gear tooth or key 3418 may be provided in the bore 3416 of the lever 3402 for mating with a corresponding one or more gear tooth or keyway 3420 (FIG. 34B) provided in the manual drive gear 3406 of the third spline 1624c when the lever 3402 is in the non-engaged position. As shown, the key 3418 is provided in a proximal segment or portion of the bore 3416, such that the key 3418 only engages the corresponding keyway 3420 (FIG. 34B) of the manual drive gear 3406 after the spacer bar 3414 has been removed from beneath the lever 3402 upon opening of the removable cover 3408 so that the user may axially displace the lever 3402 relative to the manual drive gear 3406, as shown by arrow 3422, to position the key 3418 within the corresponding keyway 3420. In addition, the bore 3416 includes a distal portion within which the manual drive gear 3406 resides when the lever 3402 is in the non-engaged position, before opening the removable cover 3408, withdrawing the spacer bar 3414 from beneath the lever 3402 and then pressing the lever 3402 in direction 3422 into the engaged position as shown in FIG. 34B. Accordingly, the lever 3402 is axially movable (slidable) in direction 3422 over the manual drive gear 3406 and the third spline 1624c, such that the manual drive gear 3405 is positionable between the distal portion of the bore 3416, where it is freely rotatable, and the proximal portion of the bore 3416, where it is rotatably fixed relative to the lever 3402. In the illustrated example, a keyed joint is provided for coupling the lever 3402 to the manual drive gear 3406 when the lever 3402 is translated distally relative to the manual drive gear 3406 to thereby position the manual drive gear 3406 within the proximal portion of bore 3416, such that rotation of the lever 3402 correspondingly rotates the manual drive gear 3406 and the third spline 1624c.

When the lever 3402 is positioned such that the manual drive gear 3406 is in the distal portion of the bore 3416, as shown in FIG. 34A, the manual drive gear 3406 may freely rotate (e.g., with the spline 1624c) without interfering or engaging with the key 3418 of the lever 3402. Accordingly, opening the removable cover 3408 and thereby removing the spacer bar 3414 from beneath the lever 3402 causes the lever 3402 to be unsupported and movable into engagement with the manual drive gear 3406, such that the lever 3402 may then be manually rotated to actuate the third spline 1624c and the activating mechanism 1638c associated therewith to control firing and retraction of the cutting element (not shown). In some embodiments, the removable cover 3408 may be connected to the removable cap 1906 at a hinge joint.

In the illustrated embodiment, the drive input 1636d of the surgical tool 1600 remains engaged with the drive output 1824d of the instrument driver 1800. Here, the instrument driver 1800 includes a backdrivable motor which may be overcome by rotation of the lever 3402, which may include one or more extendable or foldable portions to further increase mechanical advantage to overcome the motor. Thus, in the illustrated embodiment, the third spline 1624c and the manual drive gear 3406 need not translate axially upon removal of the removable cover 3408 and/or pressing the lever 3402. Rather, as mentioned above, the lever 3402 is movable relative to the third spline 1624c and the manual drive gear 3406 from a first (upper) position, where the drive input 1636d of the surgical tool 1600 is engaged with the drive output 1824d of the instrument driver 1800 and the lever 3402 of the bailout mechanism 3400 is disengaged from the manual drive gear 3406, to a second (lower) position, where the drive input 1636d of the surgical tool 1600 is remains engaged with the drive output 1824d of the instrument driver 1800 but where the lever 3402 is engaged with the manual drive gear 3406, such that a user may manually actuate the activating mechanism 1638c by manipulating the lever 3402 to control movement of the cutting element (not shown). FIG. 34A illustrate the lever 3402 in the first (upper) position, and FIG. 34B illustrates the lever 3402 in the second (lowered) position after removing the removable cover 3408 and the spacer bar 3414. In some embodiments, the drive gear 3404 is dimensioned and sized to be larger than the pinion gear 3006 such that it remains engaged and meshed with the pinion gear 3006 even if the manual drive gear 3406 and the third spline 1624c experience at least some axial translation when the lever 3402 is pressed in direction 3422.

FIG. 34B illustrates example operation of the bailout mechanism 3400 of FIG. 34A. In the illustrated embodiment, the removable cover 3408 may be removed by lifting or pivoting the removable cover 3408 as shown with arrow 3424. The spacer bar 3414 is integral with the removable cover 3408 and thus correspondingly moves, as shown with arrow 3426, with movement of the removable cover 3408 during opening or removal. Thus, removal of the removable cover 3408 simultaneously withdraws the spacer bar 3414 from beneath the lever 3402, such that the lever 3402 is unsupported and may be pressed as shown by arrow 3422 into engagement with the manual drive gear 3406. Thereafter, the user may manually turn the lever 3402, as shown by arrow 3428, to manually turn the third spline 1624c and thereby actuate the third activating mechanism 1638c to advance or retract the cutting element.

Accordingly, FIG. 34B also illustrates an exemplary method of using the bailout mechanism 3400. The method may include removing (or opening) the removable cover 3408, engaging the lever 3402, and then manually turning the lever 3402 to thereby manually activate a function of the surgical tool 1600 independent of the instrument driver 1800. Here, the action of removing (or opening) the removable cover 3408 causes the spacer bar 3414 to be withdrawn from beneath the lever 3402, such that the lever 3402 is not supported in the non-engaged position, and then engaging the lever 3402 by moving (pressing) it over the manual drive gear 3406 (as indicated by arrow 3422) until the manual drive gear 3406 is positioned within the proximal portion of the bore 3416, where the key 3418 of the lever 3402 engages the keyway 3420 of the manual drive gear 3406 such that the manual drive gear 3406 and the third spline 1624c are rotationally locked with the lever 3402. Thereafter, the user may manually retract or advance the cutting element (not shown) by turning the lever 3402.

FIGS. 35A and 35B illustrate an alternate bailout mechanism 3500 for a non-backdrivable motor, according to one or more additional embodiments of the present disclosure. In the illustrated embodiment, the bailout mechanism 3500 includes a lever 3502. The lever 3502 is positionable between a disengaged (first) position, where the lever 3502 is not coupled to the third spline 1624c, and an engaged (second) position, where the lever 3502 is utilizable to manually actuate the third activating means 1638c as described above with reference to the bailout mechanism 3400 of FIGS. 34A and 34B. However, whereas the bailout mechanism 3400 of FIGS. 34A and 34B maintains engagement between the third spline 1624c and the instrument driver 1800 as the lever 3402 thereof is moved into engagement with the manual drive gear 3406 and then actuated to manually drive the third activating mechanism 1638c, the bailout mechanism 3500 disengages (decouples) the third spline 1624c from the instrument driver 1800 as the lever 3502 thereof is moved into engagement with the manual drive gear 3406 such that the lever 3502 may be utilized to manually drive the third activating mechanism 1638c and thereby drive the firing rod 3004 to advance or retract the cutting element (not shown) operatively coupled to a distal end thereof without having to overcome the motor of the instrument driver 1800. Thus, the lever 3502 is coupled to the third spline 1624c in a manner that allows the third spline 1624c to rotate relative to the lever 3502 when the lever 3502 is in a non-engaged position, as depicted in FIG. 35A, and to rotate with the lever 3402 when the lever 3402 is in the engaged position, as depicted in FIG. 35B. Also, while FIGS. 34A and 34B illustrate the lever 3402 thereof moving in the distal direction 3422, from the disengaged (first) and into the engaged (second) position, the lever 3502 of the bailout mechanism 3500 moves proximally (in a proximal direction), from the disengaged (first) and into the engaged (second) position.

In the illustrated embodiment, the manual drive gear 3504 is provided within a bore 3504 of the lever 3502. The bore 3504 includes a first section 3506 and a second section 3508, and the lever 3502 is movable relative to the third spline 1624c and the manual drive gear 3406 to position the manual drive gear 3406 in either the first section 3506 or the second section 3508 of the bore 3504. The manual drive gear 3406 is free rotatable when oriented within the first section 3506 of the bore 3504. One or more gear teeth 3510 are provided in the second section 3508 of the bore 3504, and the one or more gear teeth 3510 are arranged to engage the manual drive gear 3406 when the manual drive gear 3406 is oriented in the second section 3508 of the bore 3504. Thus, the lever 3502 is rotationally fixed (locked) with the manual drive gear 3406, and thus the third spline 1624c, when the manual drive gear 3406 is oriented within the second section 3508 of the bore 3504. In this manner, the lever 3502 may be manually rotated to actuate the third activating means 1638c when the lever 3502 is shifted into the engaged position where the manual drive gear 3406 is positioned within the second section 3508 of the bore 3504.

The bailout mechanism 3500 further includes a biasing element 3512 and a retention pin or retaining pin 3514. In the illustrated embodiment, the biasing element 3512 is provided between the lever 3402 and the removable cap 1906, and the retaining pin 3514 is provided on the removable cover 3408 so as to extend distally therefrom within the cavity 3412 towards the lever 3502. Here, the biasing element 3512 is a compression spring that is arranged around a proximal portion of the third spline 1624c and that applies a proximally directed force on the lever 3502, thereby urging the lever 3502 away from the removable cap 1906. However, the biasing element 3512 may comprise other types of devices and/or materials instead of a compression spring and need not be arranged about the third spline 1624c as illustrated. Also, the retaining pin 3514 includes a base portion 3516 and a tip portion 3518 extending from the base portion 3516. The base portion 3516 of the retaining pin 3514 is provided on an interior surface of the removable cover 3408 such that, when the removable cover 3408 is installed on the removable cap 1906, the base portion 3516 abuts (contacts) the lever 3502 and thereby counteracts the oppositely directed spring force applied on the lever 3502 via the biasing element 3512. In addition, tip portion 3518 is provided on a distal surface of the base portion 3516 such that, when the removable cover 3408 is installed on the removable cap 1906, the tip portion 3518 abuts (contacts) the manual driver gear 3406 to thereby inhibit or limit any axial translation of the third spline 1624c and thus maintain the fourth drive input 1636d thereof engaged (coupled) with the fourth drive output 1824d of the instrument driver 1800.

In the illustrated embodiment, the base portion 3516 of the retaining pin 3514 pushes the lever 3502 distally towards the removable cap 1906, thereby compressing the biasing element 3512 when the removable cover 3408 is installed on the removable cap 1906. In this manner, the retaining pin 3514 holds or maintains the lever 3502 in the disengaged position, where the manual drive gear 3406 is freely rotatable within the first section 3506 of the bore 3504 independent of the lever 3502, and where the lever 3502 is compressing the biasing element 3512. Upon removal of the removable cover 3408 from the removable cap 1906, the biasing element 3512 pushes the lever 3502 relative to the manual drive gear 3506, as shown by directional arrow 3520 in FIG. 35B, into the engaged position where the one or more gear teeth 3510 in the second section 3508 of the bore 3504 engage (intermesh) the manual drive gear 3406.

In addition, the lever 3502 includes a ledge 3522 proximate to the second section 3508 of the bore 3504. The ledge 3522 at least partially constrains the manual drive gear 3406 within the second section 3508 and in engagement with the one or more gear teeth 3510 after the removable cap 3408 and the retaining pin 3514 thereof have been removed to thereby allow the biasing element 3512 to shift the lever 3502 proximally into the engaged position. As the biasing element 3512 pushes (translates) the lever 3502 in the proximal direction 3520, the ledge 3522 will eventually abut (contact) a distal face (side) of the manual drive gear 3406 and, as the biasing element 3512 continues to further push (translate) the lever 3502 in the proximal direction 3520, the ledges 3522 will pull the manual drive gear 3406 in the proximal direction 3520. Because the third spline 1624c is connected to the manual drive gear 3406, the third spline 1624c will axially translate in the proximal direction 3520 with the manual drive gear 3406 as the biasing element 3512 pushes the lever 3502 towards the engaged position and, as the third spline 1624c continues to axially translate in the proximal direction 3520, the fourth drive input 1636d thereof will disengaged (uncouple) from the fourth drive output 1824d of the instrument driver 1800. Here, the drive gear 3404 is dimensioned and sized to be larger than the pinion gear 3006 such that it remains engaged and meshed with the pinion gear 3006 as it moves proximally when the biasing element 3512 shifts the lever 3502 into the engaged position. In this manner, the biasing element 3512 is operable to shift the lever 3502 into engagement with the manual drive gear 3406 (i.e., the engaged position), where the lever 3502 is operable to manually actuate the third activating mechanism 1638c, and operable to decouple the third activating means 1638c from the instrument driver 1800, such that the lever 3502 may be utilized without having to overcome the motor of the instrument driver 1800.

Accordingly, FIG. 35B also illustrates an exemplary method of using the bailout mechanism 3500. The method may include removing (or opening) the removable cover 3408 and then manually turning the lever 3502 to thereby manually activate a function of the surgical tool 1600 independent of the instrument driver 1800. When the removable cover 3408 is installed on the removable cap 1906, the retaining pin 3514 abutting the lever 3502 acts against the biasing force applied on the lever 3502 by the biasing element 3512 to maintain or hold the lever 3502 in the disengaged position, where the manual drive gear 3406 is in the first section 3506 of the bore 3504 and freely rotatable relative to the lever 3502. Thus, the action of removing (or opening) the removable cover 3408 allows the biasing element 3512 to move the lever 3502 into engagement with the manual drive gear 3406 and decouple the third spline 1624c from the motor of the instrument driver 1800. In particular, this opening action of the removable cover 3408 causes the biasing element 3512 to move (shift) the lever 3502, proximally over the manual drive gear 3406 as shown by arrow 3520, such that the manual drive gear 3406 is oriented in the second section 3508 of the bore 3504 where the manual drive gear 3406 engages (intermeshes) the one or more gear teeth 3510 of the lever 3502 to thereby rotationally fix the lever 3502 to the manual drive gear 3406. Also, moving the lever 3502 into the engaged position brings the ledge 3522 into contact with the manual drive gear 3506, such that the lever 3502 may carry the manual drive gear 3406 and the third spline 1624c proximally as the biasing element 3512 further moves (shifts) the lever 3502 in the proximal direction 3520, thereby decoupling the drive input 1636d from the drive output 1824d of the instrument driver 1800 while maintaining meshed engagement between the drive gear 3404 and the pinion gear 3006 while the drive gear 3404 moves proximally. Thereafter, the user may manually turn the lever 3502, as shown by arrow 3428, to manually turn the third spline 1624c and thereby actuate the third activating mechanism 1638c to advance or retract the cutting element (not shown).

The bailout mechanisms 3400, 3500 may be integrated within the robotic system's computer-based control system. Thus, the surgical tool 1600 may communicate data and information regarding the bailout mechanisms 3400, 3500 to the robotic system's computer-based control system. In some embodiments, the bailout mechanisms 3400, 3500 may include switched transducers (and/or various other types of sensors and actuators) that could provide status indication of the bailout mechanisms 3400, 3500. For example, when the surgical tool 1600 is installed on the instrument driver 1800 (FIG. 18B), the controller 1400 (FIG. 14) may be programmed to automatically detect when the operator manually engages the bailout mechanisms 3400, 3500 (i.e., a "bail out" scenario). In these examples, the controller 1400 may be further programmed to provide instructions to the operator on how to perform the bailout, such as visible, onscreen instructions and/or audible instructions, etc. In some examples, upon installation of the surgical tool 1600 on the instrument driver 1800, the controller 1400 may be programmed to detect whether the surgical tool 1600 has previously been subjected to a "bail out" scenario and, if so, provide a user indication of the same (and possibly suggest maintenance of the surgical tool 1600) and/or control (or limit) certain functionality of the surgical tool 1600 that has previously been "bailed out". Furthermore, information and data regarding operation of the bailout mechanisms 3400, 3500 may be communicated and relayed in real-time to a help center that may provide assistance and/or verify the steps of operating the bailout mechanisms 3400, 3500. Moreover, information and data regarding operation of the bailout mechanisms 3400, 3500 may be communicated and relayed in real-time to obtain emergency medical assistance from additional physicians and/or support staff, as may be needed in the event the surgical tool 1600 experiences a bail out scenario.

FIG. 36 illustrates the surgical tool 1600 incorporating a user interface 3600, according to one or more additional embodiments. The user interface 3600 may be operated to manually translate the elongate shaft 1602 of the surgical tool 1600. In some embodiments, the user interface 3600 includes a fin 3602 that can be grasped and manipulated by the user to manually translate the elongate shaft 1602. The fin 3602 may be operatively coupled (either directly or indirectly) to the carriage 1626 such that the user is able to manually advance or retract the carriage 1626 to thereby effect a corresponding translation of the elongate shaft 1602. In the illustrated embodiment, the fin 3602 is connected to the carriage 1626 and radially protrudes outward therefrom through the window 3018 in the shroud 1640. Here, the fin 3602 is connected to the fifth layer 1628e. However, the fin 3602 may instead be connected to one or more other layers 1628a-d in addition to, or instead of, the fifth layer 1628e.

In some embodiments, as illustrated, the fin 3602 may include an overhanging portion 3604 (alternately referred to as a "distal extension") positionable within the window 3018 in the shroud 1640 to extend over or cover one or more of the distal layers (i.e., the layers 1628a-d) of the carriage 1626 when the fifth layer 1628e is releasably secured to the distal layers (i.e., the layers 1628a-d). Here, the overhanging portion 3604 is positioned radially outward from and covers at least the fourth layer 1628d of the carriage 1626 when the fifth layer 1628e is connected to the fourth layer 1628d. While, the overhanging portion 3604 is illustrated as extending distally to a location proximate the fourth layer 1628d, in other embodiments the overhanging portion 3604 may extend distally to a different extent (i.e., to cover one or more of the remaining layers 1628a-c), without departing from the present disclosure. Moreover, while the fin 3602 is illustrated as a tab protruding through the window 3018 in the shroud 1640, in other embodiments the fin 3602 may be provided with different geometries that allow a user to grasp thereto. For example, the fin 3602 may include a ring 3603 or structure that at least partially surrounds (extends around) an exterior surface of the shroud 1640.

As mentioned above, the user interface 3600 can be used to manually advance or retract the elongate shaft 1602 and the end effector 1604 (FIG. 16) in embodiments where the instrument driver 1800 (FIG. 18B) is provided with back drivable motors. For purposes of this disclosure, a back drivable motor is a motor having sufficiently low back driving torque that may be overcome by a user's manually applied torque when such user is attempting to perform a user-driven movement, and a motor's "back drivability" may be tuned by design and selection of a gear box positioned between the motor and its corresponding drive output 1824a-d. In these embodiments, the lead screw 1622 (FIG. 16) and the carriage nut 1634 (FIG. 16) may have corresponding thread pitches suitable for transforming a translation of the carriage nut 1634 along the lead screw 1622 into a rotation of the lead screw 1622 as the carriage 1626 is externally acted upon by a user. Also in these embodiments, the corresponding thread pitches of the lead screw 1622 and the carriage nut 1634 suitable for supporting the carriage nut 1634 and the carriage 1626 attached thereto at a particular position within the drive housing 1614 when the user is not applying an external load to the carriage 1626. For example, when a user applies a distally directed load on the fin 3602, the interaction between the threads of the carriage nut 1634 and the threads of the lead screw 1622 cause the lead screw 1622 to rotate and backdrive the drive output 1824a (FIG. 18B) and associated motor operatively coupled to the lead screw 1622 to drive the lead screw 1622. As the lead screw 1622 rotates, the carriage 1626 is able to traverse the lead screw 1622 in the distal direction.

In some embodiments, the fifth layer 1628e may be unlocked (detached) from the distal layers 1628a-d of the carriage 1626 and, together with the end effector 1604 (FIG. 16) and the shaft 1602 operatively coupled thereto, may be removed from the drive housing 1614. In embodiments where the surgical tool 1600 is a surgical stapler having a staple cartridge included with the end effector 1604 (FIG. 16), this may prove advantageous in allowing a user to detach the fifth layer 1628e and remove the end effector 1604 to change the end effector or replace (replenish) the staple cartridge. As will be appreciated, staple cartridges often need to be replaced or reloaded multiple times during a surgical procedure.

However, after replacing the staple cartridge and then remounting the surgical stapler in the drive housing 1614, the operator (e.g., a surgeon) may not be able to view (via an endoscope) where the end effector 1604 (FIG. 16) is located relative to the surgical site because the elongate shaft 1602 and the end effector 1604 might be located within the cannula (or trocar). To enable viewing of the end effector 1604, a user (e.g., a nurse or surgical assistant) may be able to carefully advance the elongate shaft 1602 into the patient cavity until the end effector 1604 comes into the surgeon's field of view. In this manner, the fin 3602 may be utilized to manually advance or move the elongate shaft 1602 and the end effector 1604 in a safe and efficient manner into the surgeon's field of view and/or back to a last known position.

Manual advancement and retraction of the shaft 1602 via the fin 3602 of the user interface 3600 may also provide the user with real-time tactile feedback when reinserting the elongate shaft 1602. Such real-time tactile feedback is beneficial as the user may be able to stop advancement of the end effector 1604 if an anatomical object (e.g., an organ) is felt (sensed) impeding advancement or insertion. This may be especially crucial in view of the fact that objects within the surgical environment often change or reposition upon withdrawal of a surgical tool and because robotic surgical systems may be unable to "feel" if the end effector 1604 engages an organ or tissue and instead advances through and thereby damages the organ or tissue. Accordingly, the user interface 3600 may be utilized by a user to manually advance the carriage 1626 and manually back-drive the lead screw 1622 until the end effector 1604 reaches the surgeon's field of view (or some other known location).

It should be noted that the design and function of the user interface 3600 and the associated fin 3602 are not limited to that shown in FIG. 36. Rather, the user interface 3600 may include any other design of the fin 3602 that might allow a user to grasp onto the fin 3602 and manually urge the carriage 1626 and the coupled shaft 1602 to move along the z-axis. In some embodiments, for example, the user interface 3600 and/or the fin 3602 may be substantially similar to the lever 2402 of FIG. 24. In other embodiments, the user interface 3600 and/or the fin 3602 may be substantially similar to the latch 3010 of FIGS. 30 and 32, without departing from the scope of the disclosure.

In some embodiments, upon removal of the surgical tool 1600, the instrument driver 1800 (FIG. 18B), and/or the controller 1400 (FIG. 14) of the instrument driver 1800 may be programmed to remember the last known position of the end effector (FIG. 16) and the elongate shaft 1602. Upon re-introduction of the surgical tool 1600, one or both of the instrument driver 1800 and the controller 1400 may facilitate re-positioning the end effector 1604 and the elongate shaft 1602 back into that last known position. For example, a position recognition system may be provided that remembers the last known position of the end effector 1604 and the elongate shaft 1602 and, when the fifth layer 1628e associated therewith is removed from and then re-installed on the distal layers 3704 (FIG. 37), the position recognition system recognizes when the same tool component has been reinstalled and will allow the user to manually translate the elongate shaft 1602 and the end effector 1604 back into the last known position.

However, if the fifth layer 1628e of a different surgical tool component is installed on the distal layers 3704 (FIG. 37), the position recognition system will recognize that a different tool component has been installed and will at least partially inhibit the user from manually translating the elongate shaft 1602 and the end effector 1604 at least some distance. In some embodiments, the position recognition system will recognize if the new tool component being installed on the distal layers 3704 is of the same type of component that was previously removed such that the new tool component may be manually advanced to the last known position of the previously removed tool component to the extent that they are of the same type. For example, if a robotic stapler becomes inoperable or its supply of staples is exhausted during a surgical procedure, a new surgical stapler may be installed on the distal layers 3704 and then manually advanced to the last known position. Thus, not only may the position recognition system remember and recognize the last known position of the end effector 1604 and the elongate shaft 1602, but the position recognition system may also ascertain whether a particular tool being installed on the distal layers 3704 is the same tool that was just removed therefrom or a new tool and, with regard to the latter, whether the new tool includes the same type of end effector from what was previously installed on the distal layers 3704 (i.e., the same tool type) or whether the new tool includes a different type of end effector (i.e., a different tool type).

Various technologies may be utilized for recognizing whether the same tool or a new tool is being mounted on the distal layers 3704 (FIG. 37) and/or whether the new tool is of the same or different tool type. For example, the distal layers 3704 may include a radio-frequency identification (RFID) reader device positioned to read an RFID tag of the fifth layer 1628e (or its connected components) and thereby identify the particular fifth layer and components being installed on the distal layers 3704. In some examples, physical electrical contacts, such as "pogo pin" connectors, may be utilized.

As mentioned, the position recognition system may facilitate manual advancement of the end effector 1604 (FIG. 16) and the elongate shaft 1602 back to the last known position. In some embodiments, the surgical tool 1600 may provide haptic feedback to the user when the end effector 1604 and elongate shaft 1602 have been manually advanced to the last known position. However, other types of user feedback may be provided in addition or instead, for example, various types of audible and/or visual feedback. In some embodiments, the position recognition system allows manual advancement of the end effector 1604 and elongate shaft 1602 back into the last known position but inhibits any further manual advancement beyond the last known position.

FIG. 36 also illustrates the user interface 3600 configured as a bailout mechanism, according to one or more additional embodiments. In the illustrated embodiment, a release button or pin 3606 is provided on the overhanging portion 3604 of the fin 3602 and operable to unlock the fifth layer 1628e from the layers 1628a-d distal thereof. In other examples, such as those discussed above with reference to FIGS. 24, 30, and 32, a lever or other type of locking mechanism may be utilized in lieu of the release pin 3606. In addition, a user engagement portion 3608 may be provided on the fin 3602 and/or on the overhang portion 3604 thereof. Here, the user engagement portion 3608 includes a textured surface that is more easily manipulated or handled by the user when bailing out and retracting the fifth layer 1628e and the components connected thereto from the shroud 1640 after unlocking the releasable pin 3606. In FIG. 36, the release pin 3606 is shown in an engaged or locked position, where the release pin 3606 is engaged to thereby lock the fifth layer 1628e to the fourth layer 1628d (and the underlying layers 1628a-c).

FIG. 37 illustrates example operation of the user interface 3600 of FIG. 36. As shown, the release pin 3606 may be grasped by a user and pulled outward, as shown by arrow 3702, to thereby unlock the fifth or "proximal" layer 1628e from the underlying or "distal" layers 3704. Once the release pin 3606 is released, the fifth layer 1628e may be separated and removed from the distal layers 3704.

FIG. 38 illustrates an enlarged cross-sectional view of the release pin 3606 provided on the overhang portion 3604 of the interface 3602. As depicted, the release pin 3606 is in the engaged position to secure the fifth layer 1628e to the fourth layer 1628d. In some embodiments, the releasable pin 3606 may be attachable within a locking feature 3802 in one or more of the distal layers 3704 (FIG. 37). In the illustrated embodiment, the locking feature 3802 is provided in the fourth layer 1628d, and a user may be able to pull the release pin 3606 outward 3702 to decouple (unlock) the fifth layer 1628e from the distal layers 3704. Accordingly, FIG. 38 illustrates the release pin 3606 in the locked position, where it is attached to the locking feature 3802 provided within a proximal most layer (e.g., the fourth layer 1628d) of the one or more distal layers 3704 (FIG. 37) within which the carriage nut 1634 (FIG. 16) is constrained.

Referring again to FIG. 37, once the release pin 3606 is shifted outward 3702, the fifth layer 1628e (alternately referred to as a "proximal" layer) may then be lifted proximally within the shroud 1640, as shown by arrow 3706, while the distal layers 3704 remain stationary. As the fifth layer 1628e is pulled proximally 3706, the elongate shaft 1602 correspondingly moves proximally, as shown by arrow 3708. Then, after removing the cap 1906 from the second end 1618b, as shown by arrow 3710, the fifth layer 1628e, together with the elongate shaft 1602 and the end effector 1604 (FIG. 16) coupled thereto, may be removed from the shroud 1640. Thereafter, the fifth layer 1628e and the components operatively connected thereto may be reinserted within the shroud 1640 and reinstalled on the distal layers 3704, for example, after replacing a staple cartridge in the end effector 1604, or a new fifth layer and connected components may be reinserted within the shroud 1640 and reinstalled on the distal layers 3704.

4. Implementing Systems and Terminology

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The invention claimed is:

1. A surgical tool, comprising:
  a drive housing having opposing first and second ends and a drive input rotatably mounted to the drive housing at the first end;

a carriage mounted entirely within the drive housing and movable between the first and second ends via actuation of the drive input;

a lead screw extending between and rotatably mounted to the first and second ends, the lead screw being rotatably coupled at the drive input;

a carriage nut provided within the carriage and mounted to the lead screw such that rotation of the drive input correspondingly rotates the lead screw and thereby translates the carriage along the lead screw and between the first and second ends;

an instrument driver matable with the drive housing at the first end and including a drive output matable with the drive input such that rotation of the drive output correspondingly rotates the drive input to thereby translate the carriage within the drive housing;

an elongate shaft coupled to and extending distally from the carriage and penetrating the first end and the instrument driver; and a fin connected to the carriage and accessible by a user at an exterior of the drive housing, the fin being manually translatable along the exterior of the drive housing between the first and second ends to thereby translate the carriage along the lead screw, translate the carriage nut along the lead screw, rotate the lead screw, and advance or retract the elongate shaft.

2. The surgical tool of claim 1, wherein the drive housing includes a shroud extending between the first and second end and the fin protrudes radially outward through a window defined in the shroud and extending between the first and second ends.

3. The surgical tool of claim 1, wherein the carriage comprises one or more distal layers and one or more proximal layers attachable to the one or more distal layers, and the surgical tool further comprises:

a bailout mechanism operable to unlock the one or more proximal layers from the one or more distal layers of the carriage such that the one or more proximal layers may be withdrawn from the drive housing.

4. The surgical tool of claim 3, wherein the bailout mechanism includes a releasable pin movable between a locked position, where the one or more proximal layers are secured to the one or more distal layers, and an unlocked position, where the one or more proximal layers are unsecured from and movable relative to the one or more distal layers.

5. The surgical tool of claim 4, wherein, when in the locked position, the releasable pin is attached to a locking feature provided within a proximal most layer of the one or more distal layers and the drive input is operatively coupled to the one or more distal layers.

6. The surgical tool of claim 3, wherein the fin provides an overhanging portion positioned radially outward from the drive housing and extending distally from the fin to cover at least a portion of the one or more distal layers.

7. The surgical tool of claim 1, wherein the carriage comprises one or more distal layers and one or more proximal layers removably secured to the one or more distal layers, the surgical tool further comprising:

a position recognition system programmed to remember a last known position of the end effector when the one or more proximal layers are removed from the one or more distal layers.

8. A surgical tool, comprising:

a drive housing having opposing first and second ends and a rotatable driver;

a carriage positioned within the drive housing and movable between the first and second ends;

a lead screw rotatable based on rotation of the rotatable driver;

a carriage nut threadably coupled to the lead screw, wherein the carriage nut is to drive the carriage toward the first or second end based on rotation of the lead screw;

an elongate shaft extending from the carriage and penetrating the first end and an instrument driver matable with the drive housing at the first end; and a fin coupled to the carriage and accessible by a user at an exterior of the drive housing, the fin being manually translatable toward the first or second end to thereby translate the carriage along the lead screw, translate the carriage nut along the lead screw, rotate the lead screw, and translate the elongate shaft.

9. The surgical tool of claim 8, wherein the carriage comprises one or more distal layers and one or more proximal layers attachable to the one or more distal layers, and the surgical tool further comprises:

a bailout mechanism operable to unlock the one or more proximal layers from the one or more distal layers of the carriage such that the one or more proximal layers may be withdrawn from the drive housing.

10. The surgical tool of claim 9, wherein the bailout mechanism includes a releasable pin movable between a locked position, where the one or more proximal layers are secured to the one or more distal layers, and an unlocked position, where the one or more proximal layers are unsecured from and movable relative to the one or more distal layers.

11. The surgical tool of claim 10, wherein, when in the locked position, the releasable pin is attached to a locking feature provided within a proximal most layer of the one or more distal layers and the rotatable driver is operatively coupled to the one or more distal layers.

12. The surgical tool of claim 9, wherein the fin provides an overhanging portion positioned radially outward from the drive housing and extending distally from the fin to cover at least a portion of the one or more distal layers.

\* \* \* \* \*